US008846703B2

(12) United States Patent
Ueda et al.

(10) Patent No.: US 8,846,703 B2
(45) Date of Patent: *Sep. 30, 2014

(54) CRYSTAL OF A FREE TRICYCLIC PYRAZOLOPYRIMIDINE DERIVATIVE

(71) Applicant: Daiichi Sankyo Company, Limited, Tokyo (JP)

(72) Inventors: Yasusi Ueda, Tokyo (JP); Nobuyuki Suzuki, Kanagawa (JP); Hitoshi Ohki, Tokyo (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/773,419

(22) Filed: Feb. 21, 2013

(65) Prior Publication Data

US 2013/0211084 A1    Aug. 15, 2013

Related U.S. Application Data

(63) Continuation of application No. PCT/JP2011/068889, filed on Aug. 22, 2011.

(30) Foreign Application Priority Data

Aug. 23, 2010 (JP) .................................. 2010-186459

(51) Int. Cl.
*A61K 31/55*         (2006.01)
*C07D 417/06*      (2006.01)
*C07D 495/16*      (2006.01)

(52) U.S. Cl.
CPC ............ *C07D 495/16* (2013.01); *C07D 417/06* (2013.01); *A61K 31/55* (2013.01)
USPC .......................................... 514/267; 544/251

(58) Field of Classification Search
CPC .............................. A61K 31/55; C07D 417/06
USPC .......................................... 544/251; 514/267
See application file for complete search history.

(56) References Cited

U.S. PATENT DOCUMENTS

| 8,236,813 | B2 * | 8/2012 | Ohki et al. ..................... 514/267 |
| 8,362,055 | B2 | 1/2013 | Ying |
| 8,742,133 | B2 | 6/2014 | Ying |

FOREIGN PATENT DOCUMENTS

| CN | 101072759 A | 11/2007 |
| CN | 101801983 A | 8/2010 |
| EP | 2 065 388 B1 | 9/2011 |
| JP | 2009-256323 A | 11/2009 |
| WO | 98/43991 A1 | 10/1998 |
| WO | 2004/047755 A2 | 6/2004 |
| WO | 2005/021568 A2 | 3/2005 |
| WO | 2005/028434 A2 | 3/2005 |
| WO | 2006/015263 A2 | 2/2006 |
| WO | 2008/035629 A1 | 3/2008 |
| WO | 2008/093075 A2 | 8/2008 |
| WO | 2008/100447 A2 | 8/2008 |
| WO | 2010/098344 A1 | 9/2010 |
| WO | WO 2010/098344 | * 9/2010 ........... C07D 495/16 |
| WO | WO 2010098344 | * 9/2010 ........... C07D 495/16 |

OTHER PUBLICATIONS

International Search Report mailed Sep. 13, 2011, issued in corresponding International Application No. PCT/JP2011/068889, filed Aug. 22, 2011, 1 page.
Blagg, B.S.J., and T.D. Kerr, "Hsp90 Inhibitors: Small Molecules That Transform the Hsp90 Protein Folding Machinery Into a Catalyst for Protein Degradation," Medical Research Reviews 26(3):310-338, May 2006.
Calderwood, S.K., et al., "Heat Shock Proteins in Cancer: Chaperones of Tumorigenesis," Trends in Biochemical Sciences 31(3):164-172, Mar. 2006.
Dymock, B.W., et al., "Novel, Potent Small-Molecule Inhibitors of the Molecular Chaperone Hsp90 Discovered Through Structure-Based Design," Journal of Medicinal Chemistry 48(13):4212-4215, Jun. 2005.
Hammond, D.M., et al., "The Syntheses of Tricyclic Analogues of $O^6$-Methylguanine," Organic & Biomolecular Chemistry 1(23):4166-4172, Dec. 2003.
He, H., et al., "Identification of Potent Water Soluble Purine-Scaffold Inhibitors of the Heat Shock Protein 90," Journal of Medicinal Chemistry 49(1):381-390, Jan. 2006.
Hornillo-Araujo, A.R., et al., "The Syntheses and Properties of Tricyclic Pyrrolo[2,3-d]pyrimidine Analogues of $S^6$-Methylthioguanine and $O^6$-Methylguanine," Organic & Biomolecular Chemistry 4(9):1723-1729, May 2006.
International Preliminary Report on Patentability and Written Opinion mailed Sep. 13, 2011, issued in related International Application No. PCT/JP2011/068890, filed Aug. 22, 2011, 6 pages.
Kamal, A., et al., "Therapeutic and Diagnostic Implications of Hsp90 Activation," Trends in Molecular Medicine, 10(8):283-290, Jun. 2004.

(Continued)

*Primary Examiner* — Erich A Leeser
(74) *Attorney, Agent, or Firm* — Christensen O'Connor Johnson Kindness PLLC

(57) ABSTRACT

To provide a crystal of a tricyclic pyrazolopyrimidine compound inhibiting the effect of HSP90. The present invention provides a crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide which inhibits the ATPase activity of HSP90 and which has antitumor activity, a medicament comprising the same, an anticancer agent comprising the same, and the like.

3 Claims, 22 Drawing Sheets

(56) References Cited

OTHER PUBLICATIONS

Söti, C. et al., "Heat Shock Proteins as Emerging Therapeutic Targets," British Journal of Pharmacology 146(6):769-780, Nov. 2005.
International Preliminary Report on Patentability and Written Opinion mailed Mar. 19, 2013, issued in corresponding International Application PCT/JP2011/068889, filed Aug. 22, 2011, 6 pages.
Caira, M.R., "Crystalline Polymorphism of Organic Compounds," Design of Organic Solids, Topics in Current Chemistry, Springer 198:163-208, Jan. 1998.
Extended European Search Report mailed Dec. 5, 2013, issued in corresponding European Application No. 11819896.9, filed Aug. 22, 2011, 7 pages.
Chinese Search Report mailed May 7, 2014, issued in corresponding Chinese Application No. 2011800509641, filed Aug. 22, 2011, 2 pages.

* cited by examiner

CRYSTAL OF A FREE TRICYCLIC PYRAZOLOPYRIMIDINE DERIVATIVE

TECHNICAL FIELD

The present invention relates to a compound having a tricyclic pyrazolopyrimidine skeleton which inhibits the effect of heat shock protein 90 (HSP90).

BACKGROUND ART

HSP90 is a major intracellular chaperone protein. Chaperone proteins are proteins that bind to various proteins to assist in folding of the bound proteins. A group of proteins whose folding requires HSP90 are generally called HSP90 client proteins.

It is assumed that HSP90 as well as multiple proteins such as cochaperones, partner proteins and immunophilins are involved in the mechanism of folding of client proteins by HSP90 and that they collaboratively assist in folding of HSP90 client proteins (Non Patent Document 1); however, the details of the mechanism are still not sufficiently clear.

It is assumed that HSP90 client proteins form a complex with HSP90, cochaperones and the like and are then conformationally changed to mature proteins and that the proteins are ubiquitinated and degraded by proteasomes when they are not folded normally by HSP90 and the like (Non Patent Documents 1 to 4).

In recent years, HSP90 inhibitors have been expected as candidates for therapeutic agents for various diseases (for example, cancer, neurodegenerative diseases such as Alzheimer's disease, cardiovascular diseases, infections, autoimmune diseases, and diseases associated with apoptotic cell injury) (Non Patent Document 2).

In particular, since many cancer-associated proteins including molecular targets for anticancer agents are HSP90 client proteins, HSP90 inhibitors have been expected as candidates for anticancer agents. For example, multiple proteins involved in the occurrence and development of cancer such as Her2, Raf, Akt and telomerase are known as HSP90 client proteins (Non Patent Document 1). It is assumed that these cancer-associated proteins are changed from immature proteins to mature proteins and act to cause malignant transformation of cells, respectively, by use of HSP90 as a chaperone protein. HSP90 is a protein that exists not only in cancer cells but also in normal cells, and it is reported that the affinity with a client protein and the ATPase activity necessary for its chaperone activity are higher in cancer cells than in normal cells (Non Patent Documents 1 to 3). Therefore, HSP90 inhibitors are assumed to be capable of inactivating multiple cancer-associated proteins simultaneously in a cancer cell-specific manner, and have been expected as candidates for anticancer agents that are potent and have a broad antitumor spectrum.

Geldanamycin, herbimycin, 17-allylaminogeldanamycin (17-AAG) and the like are conventionally known as HSP90 inhibitors (Non Patent Documents 1 to 4). These compounds bind to the ATP binding pocket at the N-terminal of HSP90 and inhibit binding of HSP90 to ATP in order to inhibit the function of HSP90 as a chaperone protein. Various compounds inhibiting HSP90 are reported in addition to the above compounds (Patent Document 1, Patent Document 2, Patent Document 3, Non Patent Document 5 and Non Patent Document 6) and a tricyclic pyrazolopyrimidine derivative is also reported (Patent Document 4).

Moreover, several publications have reported the intended uses of tricyclic pyrazolopyrimidine derivatives and compounds having a condensed ring structure, which also have three constituent heterocyclic rings, for anticancer purposes (Patent Documents 5 to 9, and Non Patent Documents 7 and 8).

CITATION LIST

Patent Documents

Patent Document 1: WO 2005/28434
Patent Document 2: WO 2008/049105
Patent Document 3: WO 2008/093075
Patent Document 4: WO 2008/035629
Patent Document 5: WO 2004/047755
Patent Document 6: WO 2006/015263
Patent Document 7: WO 2005/021568
Patent Document 8: WO 1998/043991
Patent Document 9: WO 2008/100447

Non Patent Documents

Non Patent Document 1: Medicinal Research Reviews (2006) Vol. 26, No. 3, 310-338
Non Patent Document 2: TRENDS in Molecular Medicine (2004) Vol. 10, No. 6, 283-290
Non Patent Document 3: British Journal of Pharmacology (2005) 146, 769-780
Non Patent Document 4: TRENDS in Biochemical Sciences (2006) March, 31 (3), 164-172
Non Patent Document 5: Journal of Medicinal Chemistry (2005) Vol. 48, No. 13, 4212-4215
Non Patent Document 6: Journal of Medicinal Chemistry (2006) Vol. 49, No. 1, 381-390
Non Patent Document 7: Organic & Biomolecular Chemistry (2003) Vol. 1, No. 23, 4166-4172
Non Patent Document 8: Organic & Biomolecular Chemistry (2006) Vol. 4, No. 9, 1723-1729

SUMMARY OF INVENTION

Problem to be Solved by the Invention

A tricyclic pyrazolopyrimidine derivative exhibits excellent HSP90 inhibitory activity and is expected to be used as a medicament, and in particular, as an anticancer agent. Moreover, it is industrially significant to find a crystal of such a derivative.

Means for Solving the Problem

In order to enhance the usefulness of a tricyclic pyrazolopyrimidine derivative which inhibits the ATPase activity of HSP90 and which has antitumor activity, for medical purposes, the present inventors have conducted extensive studies. As a result, the inventors have found a crystal of the tricyclic pyrazolopyrimidine derivative shown in the following formula (1).

More specifically, the present invention relates to the following [1] to [34]:

[1] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by the following formula (1):

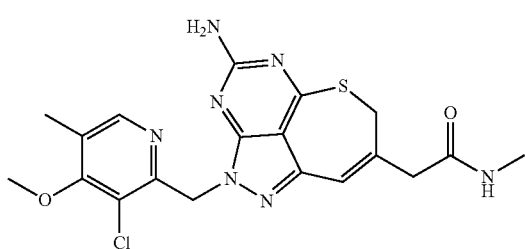

(1)

wherein the crystal has the X-ray diffraction pattern shown in FIG. 1, in an X-ray powder diffraction pattern obtained by irradiation with copper Kα radiation (wavelength λ=1.54 angstroms).

[2] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which shows principal peaks at angles of diffraction 2θ of 3.10, 4.02, 6.22, 8.54, 9.62, 11.58, 11.84, 12.16, 12.56, 14.46, 15.02, 15.26, 17.86, 22.14, 22.96, 23.10, 23.82, 24.26 and 26.82, in an X-ray powder diffraction pattern obtained by irradiation with copper Kα radiation (wavelength λ=1.54 angstroms).

[3] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which has the diffraction pattern shown in FIG. 2, in an X-ray powder diffraction pattern obtained by irradiation with copper Kα radiation (wavelength λ=1.54 angstroms).

[4] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which shows principal peaks at angles of diffraction 2θ of 5.04, 6.78, 7.72, 10.14, 11.16, 13.24, 13.66, 15.32, 18.50, 20.40, 22.36, 22.90, 25.16, 26.66, 27.92, 30.92 and 31.78, in an X-ray powder diffraction pattern obtained by irradiation with copper Kα radiation (wavelength λ=1.54 angstroms).

[5] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which has the diffraction pattern shown in FIG. 3, in an X-ray powder diffraction pattern obtained by irradiation with copper Kα radiation (wavelength λ=1.54 angstroms).

[6] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which shows principal peaks at angles of diffraction 2θ of 6.36, 6.80, 10.78, 11.30, 11.56, 12.76, 13.66, 14.68, 16.58, 17.44, 17.96, 20.58, 21.30, 23.70, 26.34, 27.58, 28.12, 29.14 and 34.68, in an X-ray powder diffraction pattern obtained by irradiation with copper Kα radiation (wavelength λ=1.54 angstroms).

[7] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which has the diffraction pattern shown in FIG. 4, in an X-ray powder diffraction pattern obtained by irradiation with copper Kα radiation (wavelength λ=1.54 angstroms).

[8] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which shows principal peaks at angles of diffraction 2θ of 6.08, 6.72, 8.42, 10.16, 10.72, 11.32, 12.22, 13.50, 14.44, 15.68, 16.96, 17.68, 20.36, 22.92, 25.58, 27.26, 27.76, 34.30 and 35.88, in an X-ray powder diffraction pattern obtained by irradiation with copper Kα radiation (wavelength λ=1.54 angstroms).

[9] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which has the diffraction pattern shown in FIG. 5, in an X-ray powder diffraction pattern obtained by irradiation with copper Kα radiation (wavelength λ=1.54 angstroms).

[10] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which shows principal peaks at angles of diffraction 2θ of 6.24, 6.84, 8.30, 11.80, 12.58, 13.74, 14.62, 19.36, 19.94, 20.74, 23.86, 24.26, 25.38, 26.00, 27.40, 27.78, 29.38, 29.54 and 30.66, in an X-ray powder diffraction pattern obtained by irradiation with copper Kα radiation (wavelength λ=1.54 angstroms).

[11] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which has the diffraction pattern shown in FIG. 6, in an X-ray powder diffraction pattern obtained by irradiation with copper Kα radiation (wavelength λ=1.54 angstroms).

[12] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which shows principal peaks at angles of diffraction 2θ of 3.26, 4.64, 5.30, 6.06, 6.54, 9.82, 11.48, 13.14, 13.98, 14.54, 15.04, 18.30, 20.62, 22.46, 23.24, 23.60, 24.48, 25.34, 26.82 and 28.12, in an X-ray powder diffraction pattern obtained by irradiation with copper Kα radiation (wavelength λ=1.54 angstroms).

[13] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which has the diffraction pattern shown in FIG. 7, in an X-ray powder diffraction pattern obtained by irradiation with copper Kα radiation (wavelength λ=1.54 angstroms).

[14] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which shows principal peaks at angles of diffraction 2θ of 4.72, 5.52, 6.18, 9.46, 10.44, 12.38, 14.22, 15.22, 15.90, 19.48, 19.74, 20.62, 21.00, 22.00, 22.28, 25.24, 26.22 and 27.34, in an X-ray powder diffraction pattern obtained by irradiation with copper Kα radiation (wavelength λ=1.54 angstroms).

[15] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which has the diffraction pattern shown in FIG. 8, in an X-ray powder diffraction pattern obtained by irradiation with copper Kα radiation (wavelength λ=1.54 angstroms).

[16] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which shows principal peaks at angles of diffraction 2θ of 7.92, 10.10, 12.50, 13.94, 14.84, 15.36, 15.50, 17.70, 18.56, 18.84, 21.26, 22.02, 22.70, 23.56, 23.88, 24.80, 25.40, 28.14 and 28.58, in an X-ray powder diffraction pattern obtained by irradiation with copper Kα radiation (wavelength λ=1.54 angstroms).

[17] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which has the diffraction pattern shown in FIG. 9, in an X-ray powder diffraction pattern obtained by irradiation with copper Kα radiation (wavelength λ=1.54 angstroms).

[18] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which shows principal peaks at angles of diffraction 2θ of 5.00, 6.70, 7.70, 10.08, 10.72, 14.42, 15.60, 18.96, 20.44, 22.34, 23.16, 23.30, 25.10, 25.48 and 28.12, in an X-ray powder diffraction pattern obtained by irradiation with copper Kα radiation (wavelength λ=1.54 angstroms).

[19] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which has the diffraction pattern shown in FIG. 10, in an X-ray powder diffraction pattern obtained by irradiation with copper Kα radiation (wavelength λ=1.54 angstroms).

[20] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which shows principal peaks at angles of diffraction 2θ of 4.70, 5.50, 9.38, 10.40, 12.36, 14.18, 15.22, 15.92, 19.78, 20.60, 21.00, 24.30, 25.56, 26.24, 26.80 and 27.30, in an X-ray powder diffraction pattern obtained by irradiation with copper Kα radiation (wavelength λ=1.54 angstroms).

[21] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which has the diffraction pattern shown in FIG. 11, in an X-ray powder diffraction pattern obtained by irradiation with copper Kα radiation (wavelength λ=1.54 angstroms).

[22] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which shows principal peaks at angles of diffraction 2θ of 6.88, 10.04, 13.84, 15.40, 15.58, 18.50, 19.60, 20.16, 20.80, 21.58, 21.94, 22.36, 22.68, 23.22, 23.42, 24.84, 25.34, 26.20, 27.16, 27.42, 28.04 and 31.80, in an X-ray powder diffraction pattern obtained by irradiation with copper Kα radiation (wavelength λ=1.54 angstroms).

[23] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which has the diffraction pattern shown in FIG. 12, in an X-ray powder diffraction pattern obtained by irradiation with copper Kα radiation (wavelength λ=1.54 angstroms).

[24] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which shows principal peaks at angles of diffraction 2θ of 7.46, 10.18, 12.68, 14.30, 14.96, 15.10, 16.34, 20.26, 21.94, 22.52, 22.70, 24.28, 24.48, 24.78 and 25.48, in an X-ray powder diffraction pattern obtained by irradiation with copper Kα radiation (wavelength λ=1.54 angstroms).

[25] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which has the diffraction pattern shown in FIG. 13, in an X-ray powder diffraction pattern obtained by irradiation with copper Kα radiation (wavelength λ=1.54 angstroms).

[26] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which shows principal peaks at angles of diffraction 2θ of 8.12, 9.78, 10.86, 13.60, 13.94, 15.86, 16.32, 17.10, 18.48, 19.54, 20.04, 20.36, 20.62, 23.10, 24.26, 24.60, 24.96, 25.32, 25.64 and 26.76, in an X-ray powder diffraction pattern obtained by irradiation with copper Kα radiation (wavelength λ=1.54 angstroms).

[27] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which has the diffraction pattern shown in FIG. 14, in an X-ray powder diffraction pattern obtained by irradiation with copper Kα radiation (wavelength λ=1.54 angstroms).

[28] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which shows principal peaks at angles of diffraction 2θ of 3.10, 4.00, 6.24, 8.54, 9.62, 11.50, 11.82, 12.14, 13.56, 14.44, 14.98, 15.22, 17.18, 17.60, 17.82, 20.72, 22.12 and 24.18, in an X-ray powder diffraction pattern obtained by irradiation with copper Kα radiation (wavelength λ=1.54 angstroms).

[29] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which has the diffraction pattern shown in FIG. 15, in an X-ray powder diffraction pattern obtained by irradiation with copper Kα radiation (wavelength λ=1.54 angstroms).

[30] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which shows principal peaks at angles of diffraction 2θ of 5.02, 7.70, 8.22, 10.12, 14.06, 15.24, 15.50, 16.54, 17.36, 20.38, 22.36, 22.76, 23.32, 25.02, 25.60, 26.90, 27.54, 28.04 and 30.72, in an X-ray powder diffraction pattern obtained by irradiation with copper Kα radiation (wavelength λ=1.54 angstroms).

[31] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which has the diffraction pattern shown in FIG. 16, in an X-ray powder diffraction pattern obtained by irradiation with copper Kα radiation (wavelength λ=1.54 angstroms).

[32] A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by formula (1) as defined in [1] which shows principal peaks at angles of diffraction 2θ of 5.08, 6.56, 7.90, 8.72, 11.58, 13.18, 13.64, 14.64, 15.86, 17.34, 18.20, 19.94, 20.72, 22.24, 23.32, 24.78, 25.76, 26.48, 27.64 and 28.34, in an X-ray powder diffraction pattern obtained by irradiation with copper Kα radiation (wavelength λ=1.54 angstroms).

[33] A pharmaceutical composition comprising a crystal according to any one of [1] to [32].

[34] An anticancer agent comprising a crystal according to any one of [1] to [32].

Advantages of the Invention

According to the present invention, there is provided a crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide having HSP90 inhibitory activity. The crystal of the present invention has excellent stability and is useful as an anticancer agent.

DESCRIPTION OF EMBODIMENTS

The present invention relates to a crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (hereinafter also referred to as "compound (1)") represented by formula (1) shown below:

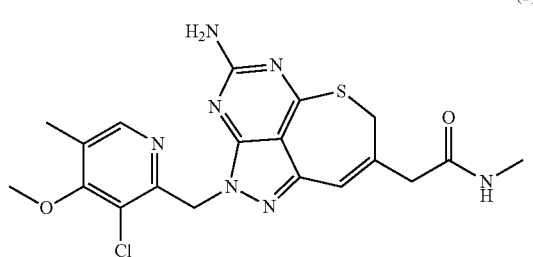

(1)

Herein, the term "crystal" means a solid whose internal structure is made up of three-dimensionally regular repeats of constituent atoms (or a group thereof). Thus, a crystal can be distinguished from an amorphous solid that does not have such a regular internal structure.

Even from a single compound, there may be a case in which a plurality of crystals (crystalline polymorphism) having different internal structures and different physicochemical properties are generated, depending on the conditions for crystallization. The crystal of the present invention may be any one of these polymorphic forms, and may also be a mixture of two or more polymorphic forms.

Moreover, the crystal of the invention of the present application, which is shown below as a preferred crystalline form, may consist only of the crystalline form, may be contained in a mixture with other crystals, or may be contained in a mixture with an amorphous substance. Hence, the situations in which the crystal of the present invention may exist are not particularly limited.

The crystal of the present invention may absorb moisture by being left in the air, and as a result, water may adhere to the surface thereof, or the crystal of the present invention may form a hydrate by being heated to a temperature of 25° C. to 150° C. under ordinary atmospheric conditions. Furthermore, in the case of the crystal of the present invention, a solvent used in crystallization may be contained in a residual solvent adhering to the surface thereof or a solvate.

In the present specification, the crystal of the present invention is identified on the basis of X-ray powder diffraction data. The measurement and/or analysis of such X-ray powder diffraction data may be carried out by means commonly used in the present technical field. For example, the X-ray powder diffraction may be carried out by the methods described in Examples. In general, the lattice constant of a hydrate or a dehydration product changes due to the attachment or removal of crystal water and, as a result, it may change the angle of diffraction (2θ) in the X-ray powder diffraction. In addition, the peak intensity may change depending on the difference in the growth face of the crystal (crystal habit), etc. Accordingly, when the crystal of the present invention is identified on the basis of X-ray powder diffraction data, not only crystals having the same peak angle of diffraction and the same X-ray diffraction pattern in the X-ray powder diffraction, but also hydrates and dehydration products obtained from the aforementioned crystals, are included in the scope of the present invention.

Figure 1:
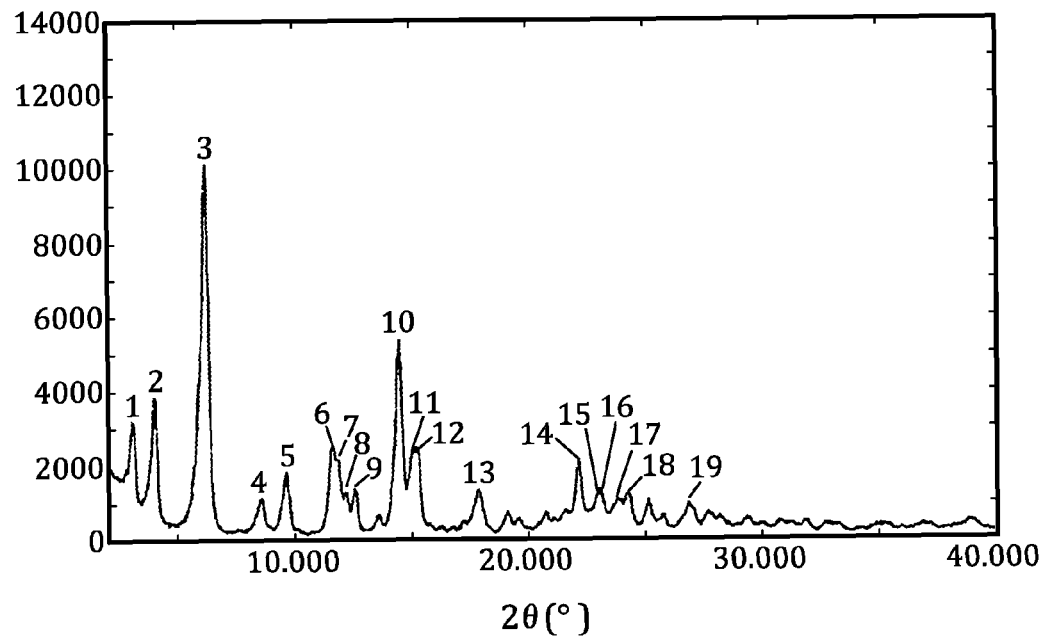
FIG. 1 shows an X-ray powder diffraction pattern of the crystal obtained in Example 1 (crystal A). The longitudinal axis of the pattern shows diffraction intensity as a count/sec (cps) unit, and the horizontal axis shows the value of the angle of diffraction 2θ.

One preferred form of the crystal of the present invention is a crystal (crystal A) having the X-ray diffraction pattern shown in FIG. 1, in an X-ray powder diffraction pattern obtained by irradiation with copper Kα radiation (wavelength λ=1.54 angstroms). In addition, crystal A has principal peaks at angles of diffraction 2θ of 3.10, 4.02, 6.22, 8.54, 9.62, 11.58, 11.84, 12.16, 12.56, 14.46, 15.02, 15.26, 17.86, 22.14, 22.96, 23.10, 23.82, 24.26 and 26.82 in an X-ray powder diffraction pattern obtained by irradiation with copper Kα radiation (wavelength λ=1.54 angstroms). The term "principal peak" is used herein to mean a peak with a relative intensity of 10 or greater, when the maximum peak intensity is set at 100 in the X-ray powder diffraction pattern.

Figure 2:
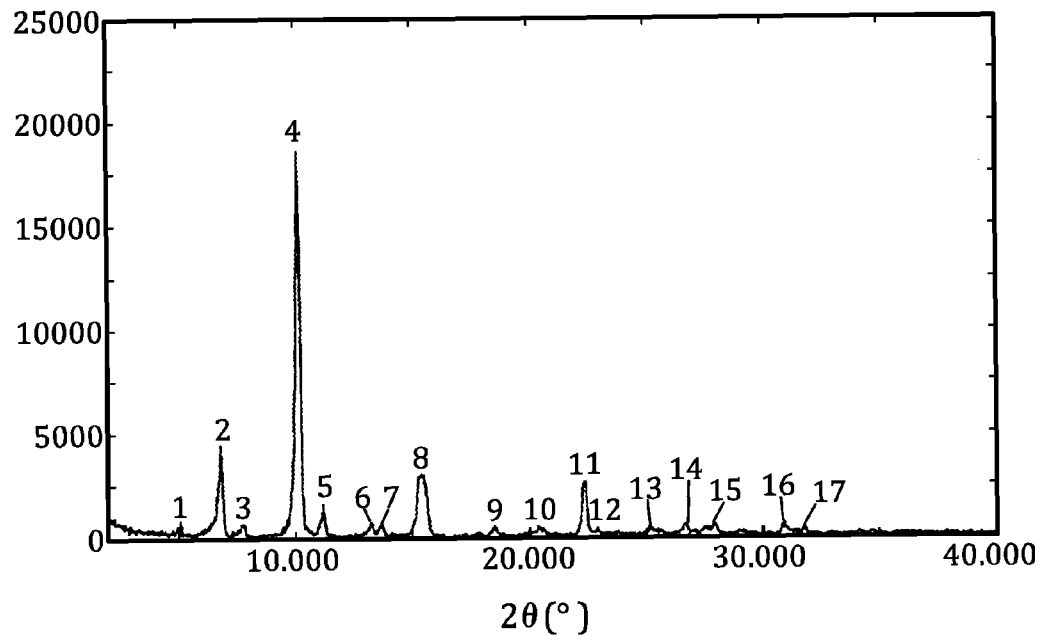
FIG. 2 shows an X-ray powder diffraction pattern of the crystal obtained in Example 2 (crystal B). The longitudinal axis of the pattern shows diffraction intensity as a count/sec (cps) unit, and the horizontal axis shows the value of the angle of diffraction 2θ.

Another preferred form of the crystal of the present invention is a crystal (crystal B) having the X-ray diffraction pattern shown in FIG. 2, in an X-ray powder diffraction pattern obtained by irradiation with copper Kα radiation (wavelength λ=1.54 angstroms). In addition, crystal B in the present form is also a crystal that shows principal peaks at angles of diffraction 2θ of 5.04, 6.78, 7.72, 10.14, 11.16, 13.24, 13.66, 15.32, 18.50, 20.40, 22.36, 22.90, 25.16, 26.66, 27.92, 30.92 and 31.78 in an X-ray powder diffraction pattern obtained by irradiation with copper Kα radiation (wavelength λ=1.54 angstroms). The term "principal peak" is used herein to mean a peak with a relative intensity of 3 or greater, when the maximum peak intensity is set at 100 in the X-ray powder diffraction pattern.

Figure 3:
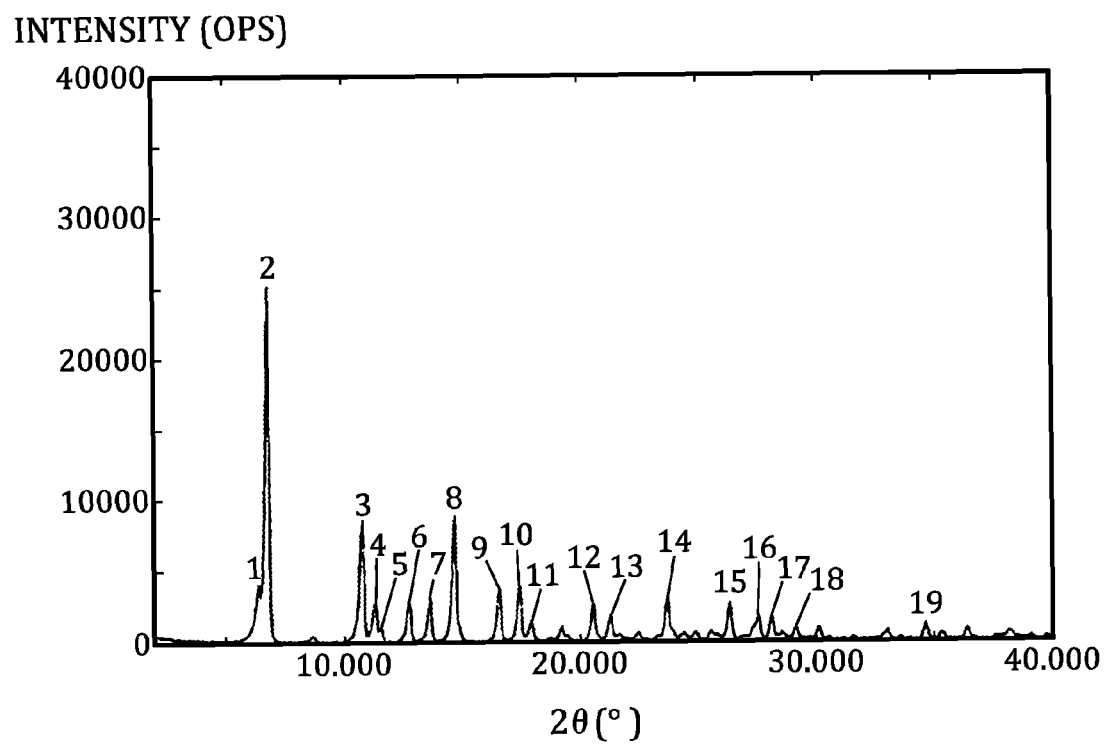
FIG. 3 shows an X-ray powder diffraction pattern of the crystal obtained in Example 3 (crystal C). The longitudinal axis of the pattern shows diffraction intensity as a count/sec (cps) unit, and the horizontal axis shows the value of the angle of diffraction 2θ.

Another preferred form of the crystal of the present invention is a crystal (crystal C) having the X-ray powder diffraction pattern shown in FIG. 3, in an X-ray powder diffraction pattern obtained by irradiation with copper Kα radiation (wavelength λ=1.54 angstroms). In addition, crystal C is also a crystal that shows principal peaks at angles of diffraction 2θ of 6.36, 6.80, 10.78, 11.30, 11.56, 12.76, 13.66, 14.68, 16.58, 17.44, 17.96, 20.58, 21.30, 23.70, 26.34, 27.58, 28.12, 29.14 and 34.68 in an X-ray powder diffraction pattern obtained by irradiation with copper Kα radiation (wavelength λ=1.54 angstroms). The term "principal peak" is used herein to mean a peak with a relative intensity of 5 or greater, when the maximum peak intensity is set at 100 in the X-ray powder diffraction pattern.

Figure 4:
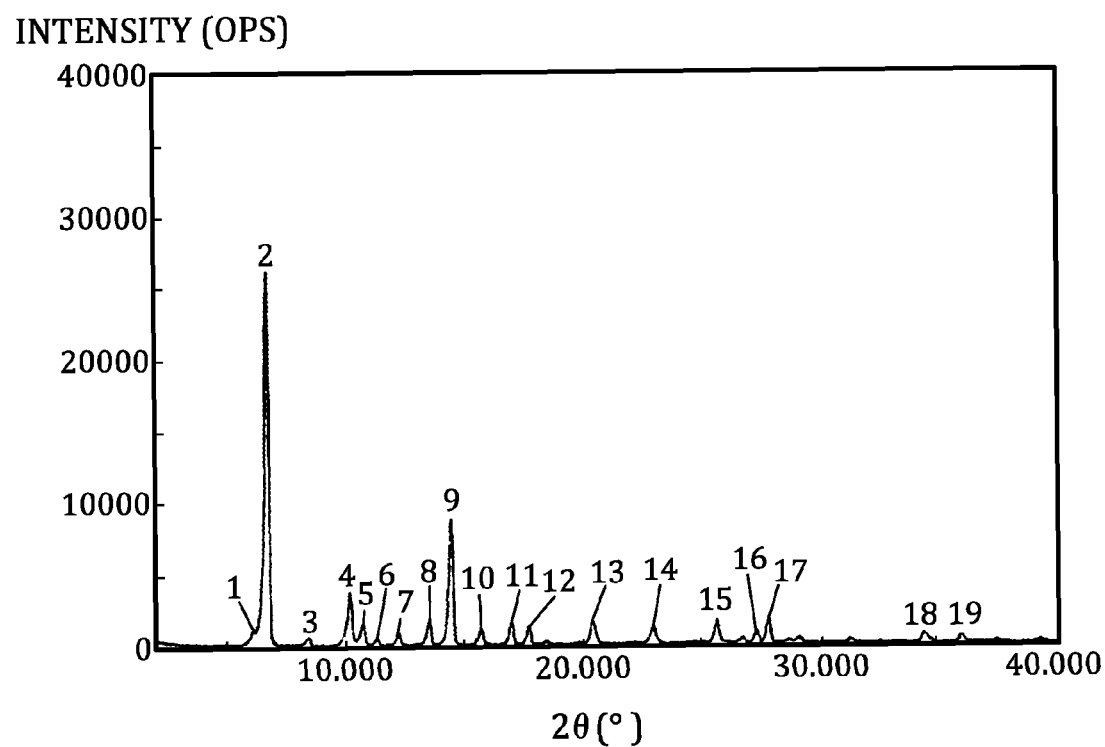
FIG. 4 shows an X-ray powder diffraction pattern of the crystal obtained in Example 4 (crystal D). The longitudinal axis of the pattern shows diffraction intensity as a count/sec (cps) unit, and the horizontal axis shows the value of the angle of diffraction 2θ.

Another preferred form of the crystal of the present invention is a crystal (crystal D) having the X-ray diffraction pattern shown in FIG. 4, in an X-ray powder diffraction pattern obtained by irradiation with copper Kα radiation (wavelength λ=1.54 angstroms). In addition, crystal D is also a crystal that shows principal peaks at angles of diffraction 2θ of 6.08, 6.72, 8.42, 10.16, 10.72, 11.32, 12.22, 13.50, 14.44, 15.68, 16.96, 17.68, 20.36, 22.92, 25.58, 27.26, 27.76, 34.30 and 35.88 in an X-ray powder diffraction pattern obtained by irradiation with copper Kα radiation (wavelength λ=1.54 angstroms). The term "principal peak" is used herein to mean a peak with a relative intensity of 3 or greater, when the maximum peak intensity is set at 100 in the X-ray powder diffraction pattern.

Figure 5:
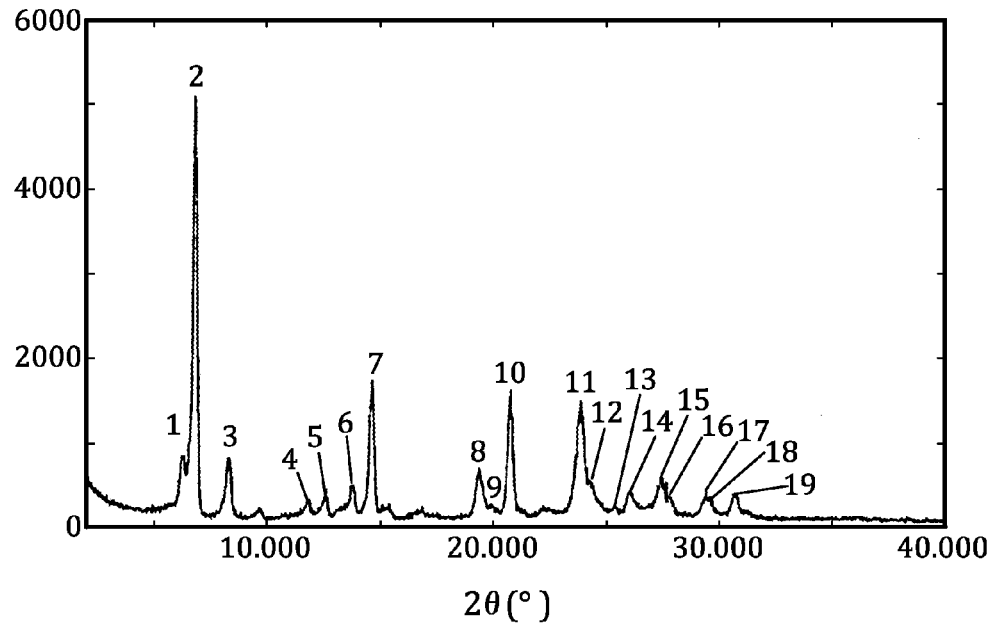
FIG. 5 shows an X-ray powder diffraction pattern of the crystal obtained in Example 5 (crystal E). The longitudinal axis of the pattern shows diffraction intensity as a count/sec (cps) unit, and the horizontal axis shows the value of the angle of diffraction 2θ.

Another preferred form of the crystal of the present invention is a crystal (crystal E) having the X-ray diffraction pattern shown in FIG. 5, in an X-ray powder diffraction pattern obtained by irradiation with copper Kα radiation (wavelength λ=1.54 angstroms). In addition, crystal E is also a crystal that shows principal peaks at angles of diffraction 2θ of 6.24, 6.84, 8.30, 11.80, 12.58, 13.74, 14.62, 19.36, 19.94, 20.74, 23.86, 24.26, 25.38, 26.00, 27.40, 27.78, 29.38, 29.54 and 30.66 in an X-ray powder diffraction pattern obtained by irradiation with copper Kα radiation (wavelength λ=1.54 angstroms). The term "principal peak" is used herein to mean a peak with a relative intensity of 5 or greater, when the maximum peak intensity is set at 100 in the X-ray powder diffraction pattern.

Figure 6:
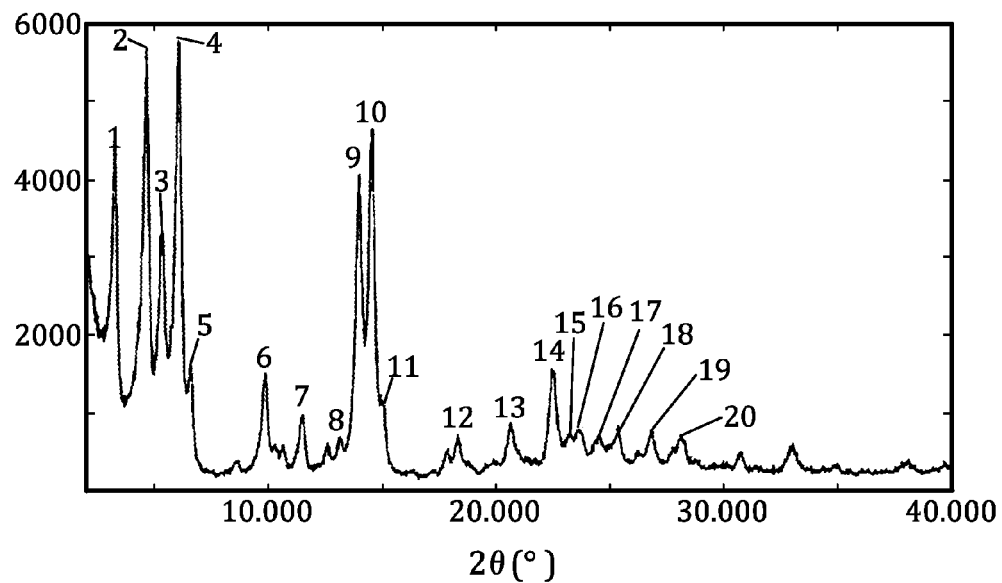
FIG. 6 shows an X-ray powder diffraction pattern of the crystal obtained in Example 6 (crystal F). The longitudinal axis of the pattern shows diffraction intensity as a count/sec (cps) unit, and the horizontal axis shows the value of the angle of diffraction 2θ.

Another preferred form of the crystal of the present invention is a crystal (crystal F) having the X-ray diffraction pattern shown in FIG. 6, in an X-ray powder diffraction pattern obtained by irradiation with copper Kα radiation (wavelength λ=1.54 angstroms). In addition, crystal F is also a crystal that shows principal peaks at angles of diffraction 2θ of 3.26, 4.64, 5.30, 6.06, 6.54, 9.82, 11.48, 13.14, 13.98, 14.54, 15.04, 18.30, 20.62, 22.46, 23.24, 23.60, 24.48, 25.34, 26.82 and 28.12 in an X-ray powder diffraction pattern obtained by irradiation with copper Kα radiation (wavelength λ=1.54 angstroms). The term "principal peak" is used herein to mean a peak with a relative intensity of 12 or greater, when the maximum peak intensity is set at 100 in the X-ray powder diffraction pattern.

Figure 7:
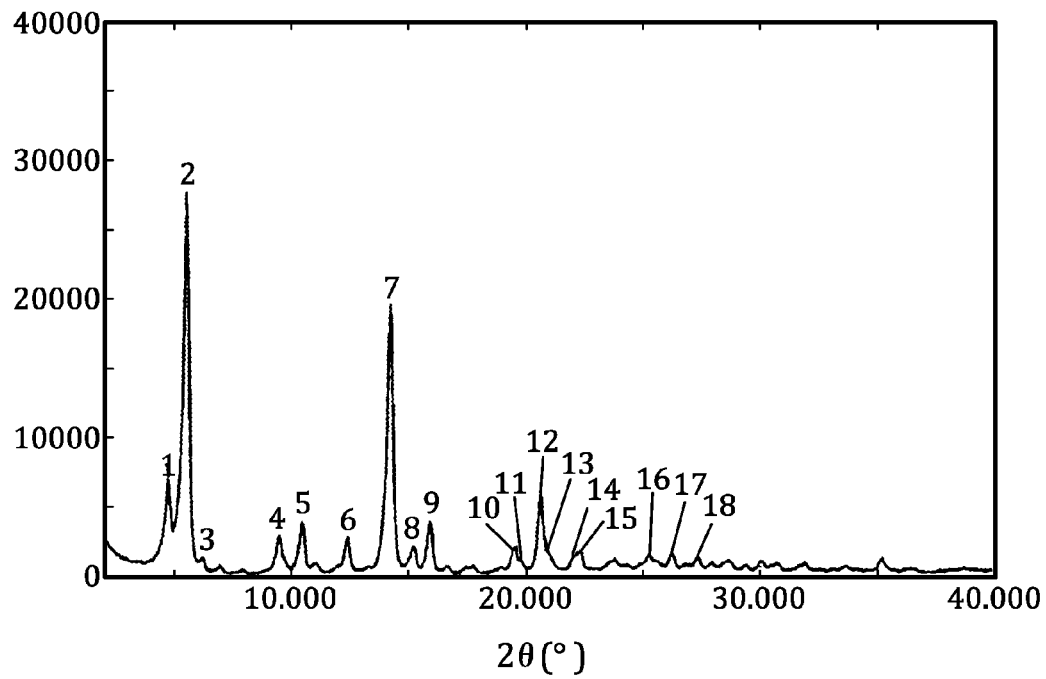
FIG. 7 shows an X-ray powder diffraction pattern of the crystal obtained in Example 7 (crystal G). The longitudinal axis of the pattern shows diffraction intensity as a count/sec (cps) unit, and the horizontal axis shows the value of the angle of diffraction 2θ.

Another preferred form of the crystal of the present invention is a crystal (crystal G) having the X-ray diffraction pattern shown in FIG. 7, in an X-ray powder diffraction pattern obtained by irradiation with copper Kα radiation (wavelength λ=1.54 angstroms). In addition, crystal G is also a crystal that shows principal peaks at angles of diffraction 2θ of 4.72, 5.52, 6.18, 9.46, 10.44, 12.38, 14.22, 15.22, 15.90, 19.48, 19.74, 20.62, 21.00, 22.00, 22.28, 25.24, 26.22 and 27.34 in an X-ray powder diffraction pattern obtained by irradiation with copper Kα radiation (wavelength λ=1.54 angstroms). The term "principal peak" is used herein to mean a peak with a relative intensity of 5 or greater, when the maximum peak intensity is set at 100 in the X-ray powder diffraction pattern.

Figure 8:
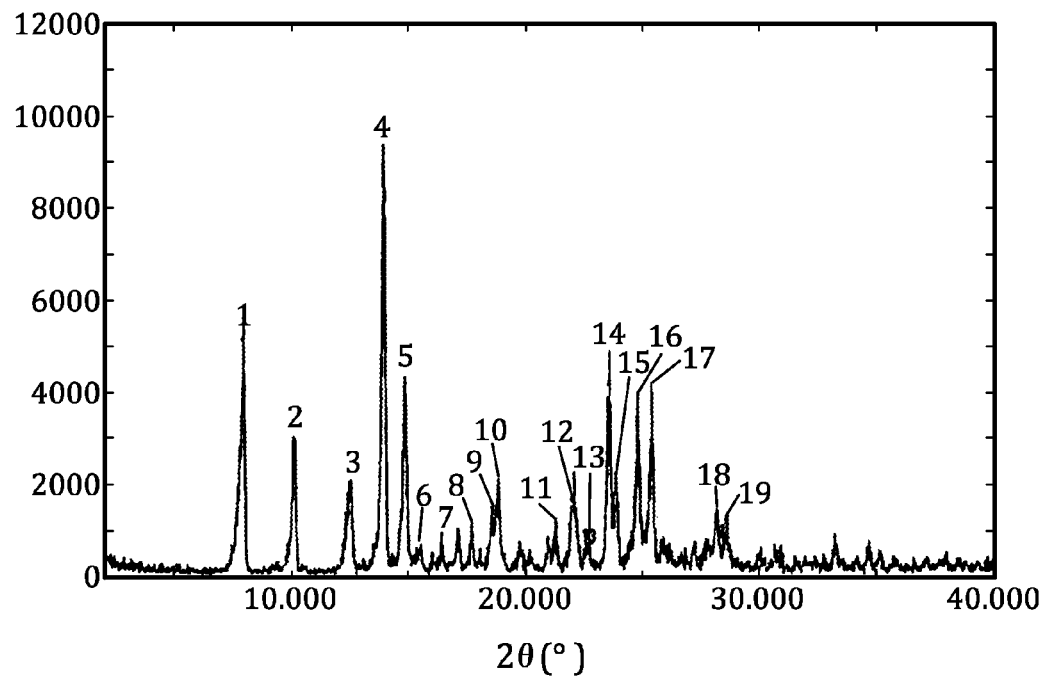
FIG. 8 shows an X-ray powder diffraction pattern of the crystal obtained in Example 8 (crystal H). The longitudinal axis of the pattern shows diffraction intensity as a count/sec (cps) unit, and the horizontal axis shows the value of the angle of diffraction 2θ.

Another preferred form of the crystal of the present invention is a crystal (crystal H) having the X-ray diffraction pattern shown in FIG. 8, in an X-ray powder diffraction pattern obtained by irradiation with copper Kα radiation (wavelength λ=1.54 angstroms). In addition, crystal H is also a crystal that shows principal peaks at angles of diffraction 2θ of 7.92, 10.10, 12.50, 13.94, 14.84, 15.36, 15.50, 17.70, 18.56, 18.84, 21.26, 22.02, 22.70, 23.56, 23.88, 24.80, 25.40, 28.14 and 28.58 in an X-ray powder diffraction pattern obtained by irradiation with copper Kα radiation (wavelength λ=1.54 angstroms). The term "principal peak" is used herein to mean a peak with a relative intensity of 8 or greater, when the maximum peak intensity is set at 100 in the X-ray powder diffraction pattern.

Figure 9:
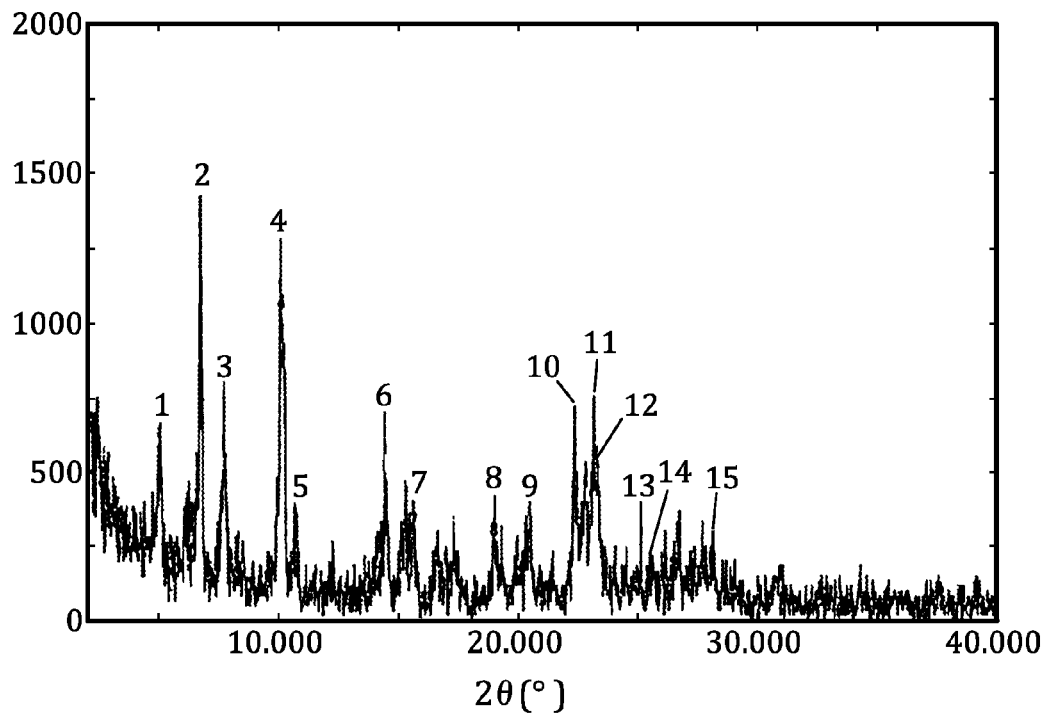
FIG. 9 shows an X-ray powder diffraction pattern of the crystal obtained in Example 9 (crystal I). The longitudinal axis of the pattern shows diffraction intensity as a count/sec (cps) unit, and the horizontal axis shows the value of the angle of diffraction 2θ.

Another preferred form of the crystal of the present invention is a crystal (crystal I) having the X-ray diffraction pattern shown in FIG. 9, in an X-ray powder diffraction pattern obtained by irradiation with copper Kα radiation (wavelength λ=1.54 angstroms). In addition, crystal I is also a crystal that shows principal peaks at angles of diffraction 2θ of 5.00, 6.70, 7.70, 10.08, 10.72, 14.42, 15.60, 18.96, 20.44, 22.34, 23.16, 23.30, 25.10, 25.48 and 28.12 in an X-ray powder diffraction pattern obtained by irradiation with copper Kα radiation (wavelength λ=1.54 angstroms). The term "principal peak" is used herein to mean a peak with a relative intensity of 17 or greater, when the maximum peak intensity is set at 100 in the X-ray powder diffraction pattern.

Figure 10:
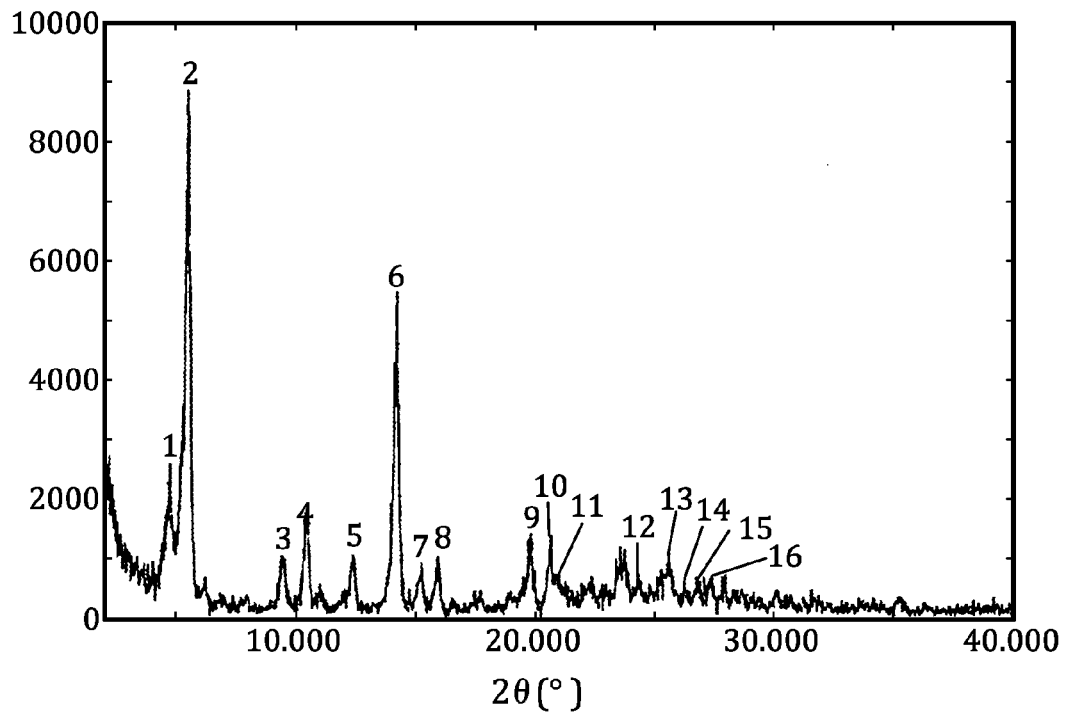
FIG. 10 shows an X-ray powder diffraction pattern of the crystal obtained in Example 10 (crystal J). The longitudinal axis of the pattern shows diffraction intensity as a count/sec (cps) unit, and the horizontal axis shows the value of the angle of diffraction 2θ.

Another preferred form of the crystal of the present invention is a crystal (crystal J) having the X-ray diffraction pattern shown in FIG. 10, in an X-ray powder diffraction pattern obtained by irradiation with copper Kα radiation (wavelength λ=1.54 angstroms). In addition, crystal J is also a crystal that shows principal peaks at angles of diffraction 2θ of 4.70, 5.50, 9.38, 10.40, 12.36, 14.18, 15.22, 15.92, 19.78, 20.60, 21.00, 24.30, 25.56, 26.24, 26.80 and 27.30 in an X-ray powder diffraction pattern obtained by irradiation with copper Kα radiation (wavelength λ=1.54 angstroms). The term "principal peak" is used herein to mean a peak with a relative intensity of 7 or greater, when the maximum peak intensity is set at 100 in the X-ray powder diffraction pattern.

Figure 11:
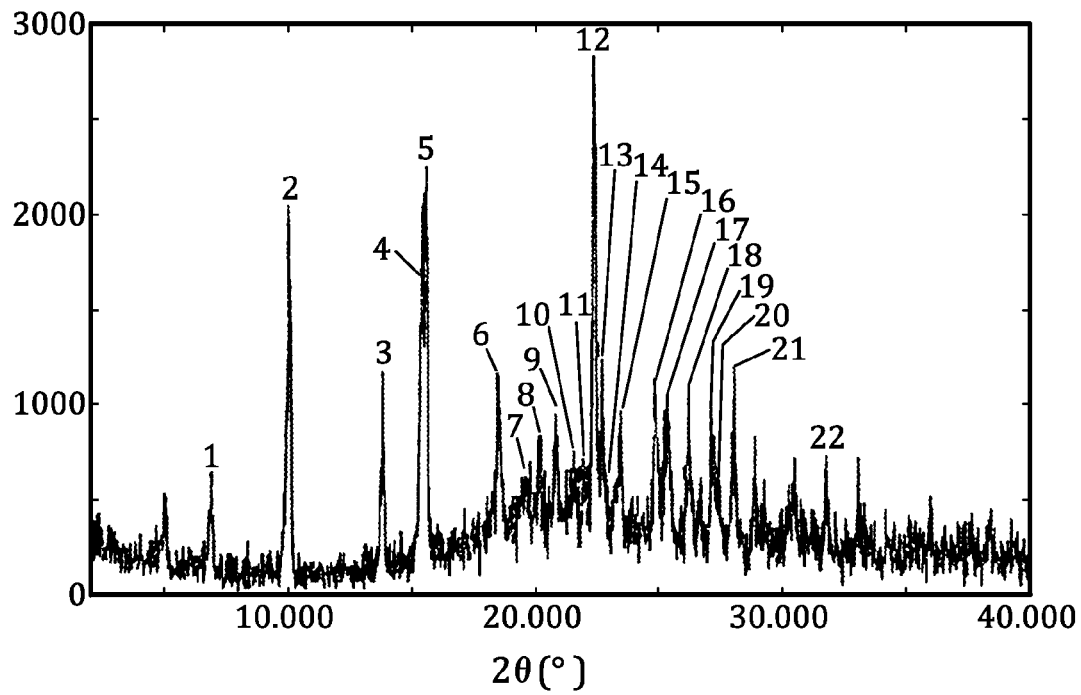
FIG. 11 shows an X-ray powder diffraction pattern of the crystal obtained in Example 11 (crystal K). The longitudinal axis of the pattern shows diffraction intensity as a count/sec (cps) unit, and the horizontal axis shows the value of the angle of diffraction 2θ.

Another preferred form of the crystal of the present invention is a crystal (crystal K) having the X-ray diffraction pattern shown in FIG. 11, in an X-ray powder diffraction pattern obtained by irradiation with copper Kα radiation (wavelength λ=1.54 angstroms). In addition, crystal K is also a crystal that shows principal peaks at angles of diffraction 2θ of 6.88, 10.04, 13.84, 15.40, 15.58, 18.50, 19.60, 20.16, 20.80, 21.58, 21.94, 22.36, 22.68, 23.22, 23.42, 24.84, 25.34, 26.20, 27.16, 27.42, 28.04 and 31.80 in an X-ray powder diffraction pattern obtained by irradiation with copper Kα radiation (wavelength λ=1.54 angstroms). The term "principal peak" is used herein to mean a peak with a relative intensity of 21 or greater, when the maximum peak intensity is set at 100 in the X-ray powder diffraction pattern.

Figure 12:
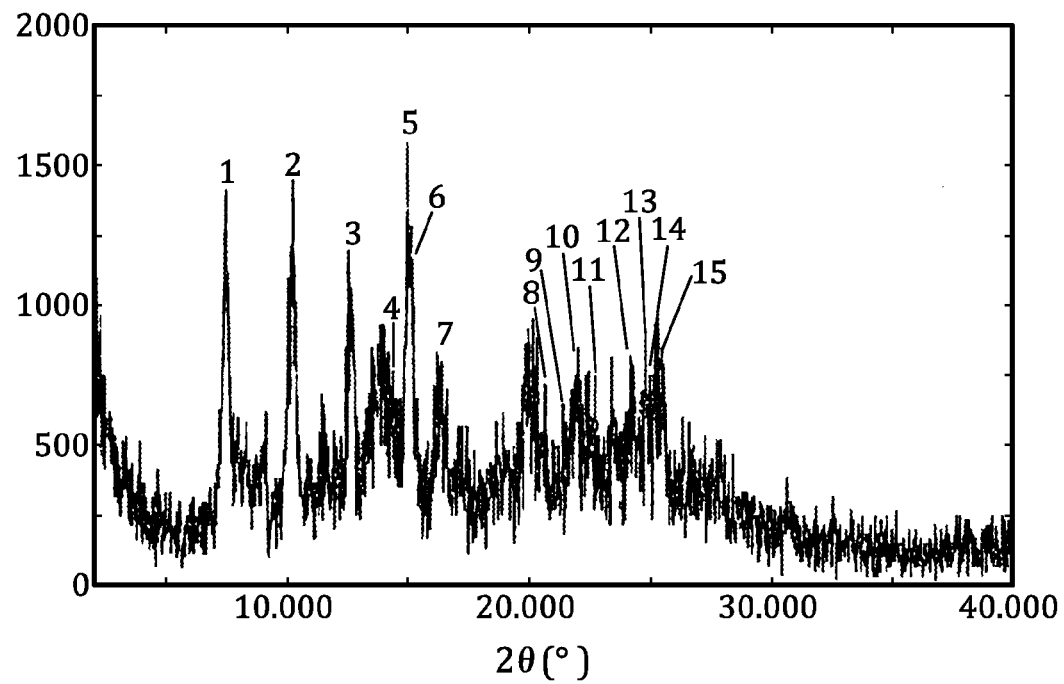
FIG. 12 shows an X-ray powder diffraction pattern of the crystal obtained in Example 12 (crystal L). The longitudinal axis of the pattern shows diffraction intensity as a count/sec (cps) unit, and the horizontal axis shows the value of the angle of diffraction 2θ.

Another preferred form of the crystal of the present invention is a crystal (crystal L) having the X-ray diffraction pattern shown in FIG. 12, in an X-ray powder diffraction pattern obtained by irradiation with copper Kα radiation (wavelength λ=1.54 angstroms). In addition, crystal L is also a crystal that shows principal peaks at angles of diffraction 2θ of 7.46, 10.18, 12.68, 14.30, 14.96, 15.10, 16.34, 20.26, 21.94, 22.52, 22.70, 24.28, 24.48, 24.78 and 25.48 in an X-ray powder diffraction pattern obtained by irradiation with copper Kα radiation (wavelength λ=1.54 angstroms). The term "principal peak" is used herein to mean a peak with a relative intensity of 38 or greater, when the maximum peak intensity is set at 100 in the X-ray powder diffraction pattern.

Figure 13:
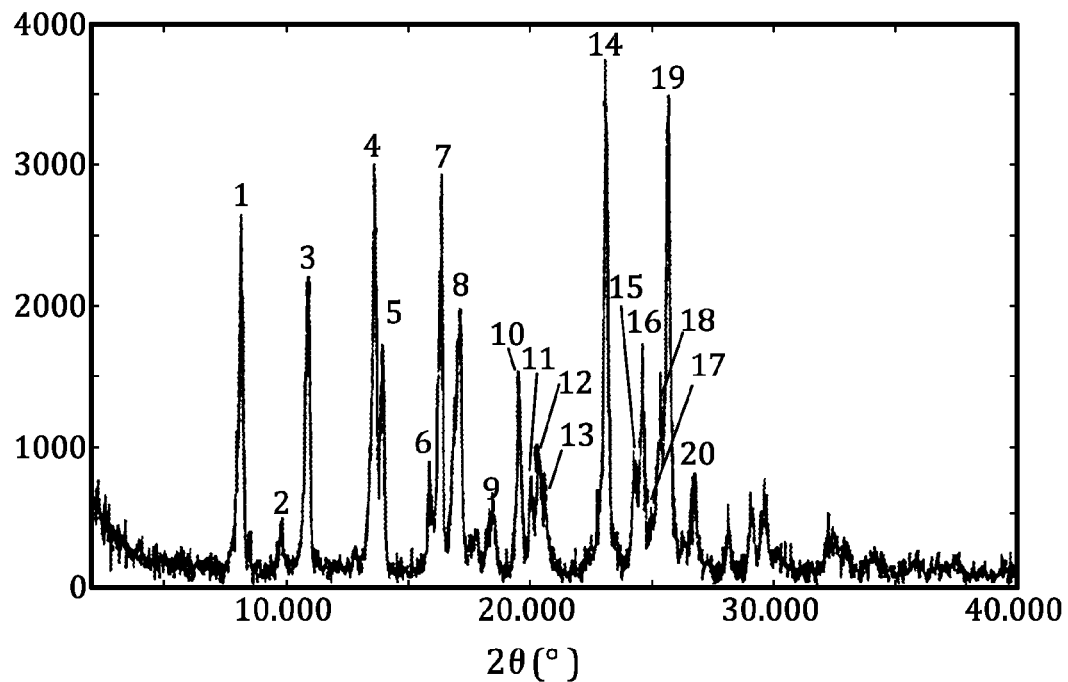
FIG. 13 shows an X-ray powder diffraction pattern of the crystal obtained in Example 13 (crystal M). The longitudinal axis of the pattern shows diffraction intensity as a count/sec (cps) unit, and the horizontal axis shows the value of the angle of diffraction 2θ.

Another preferred form of the crystal of the present invention is a crystal (crystal M) having the X-ray diffraction pattern shown in FIG. 13, in an X-ray powder diffraction pattern obtained by irradiation with copper Kα radiation (wavelength λ=1.54 angstroms). In addition, crystal M is also a crystal that shows principal peaks at angles of diffraction 2θ of 8.12, 9.78, 10.86, 13.60, 13.94, 15.86, 16.32, 17.10, 18.48, 19.54, 20.04, 20.36, 20.62, 23.10, 24.26, 24.60, 24.96, 25.32, 25.64 and 26.76 in an X-ray powder diffraction pattern obtained by irradiation with copper Kα radiation (wavelength λ=1.54 angstroms). The term "principal peak" is used herein to mean a peak with a relative intensity of 15 or greater, when the maximum peak intensity is set at 100 in the X-ray powder diffraction pattern.

Figure 14:
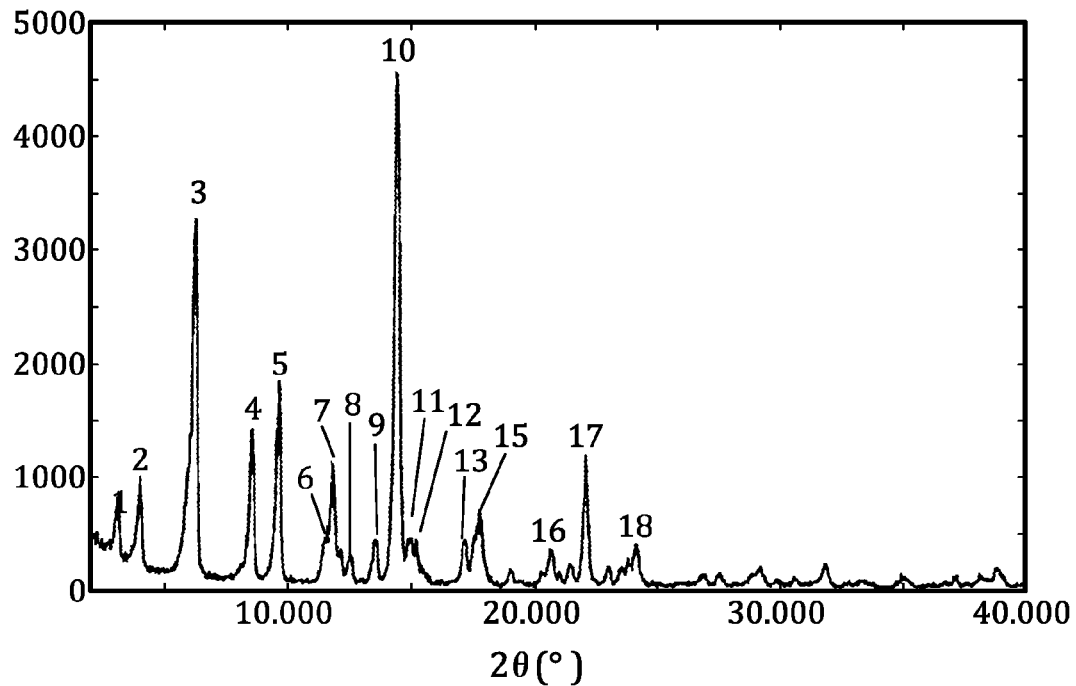
FIG. 14 shows an X-ray powder diffraction pattern of the crystal obtained in Example 14 (crystal N). The longitudinal axis of the pattern shows diffraction intensity as a count/sec (cps) unit, and the horizontal axis shows the value of the angle of diffraction 2θ.

Another preferred form of the crystal of the present invention is a crystal (crystal N) having the X-ray diffraction pattern shown in FIG. 14, in an X-ray powder diffraction pattern obtained by irradiation with copper Kα radiation (wavelength λ=1.54 angstroms). In addition, crystal N is also a crystal that shows principal peaks at angles of diffraction 2θ of 3.10, 4.00, 6.24, 8.54, 9.62, 11.50, 11.82, 12.14, 13.56, 14.44, 14.98, 15.22, 17.18, 17.60, 17.82, 20.72, 22.12 and 24.18 in an X-ray powder diffraction pattern obtained by irradiation with copper Kα radiation (wavelength λ=1.54 angstroms). The term "principal peak" is used herein to mean a peak with a relative intensity of 8 or greater, when the maximum peak intensity is set at 100 in the X-ray powder diffraction pattern.

Figure 15:
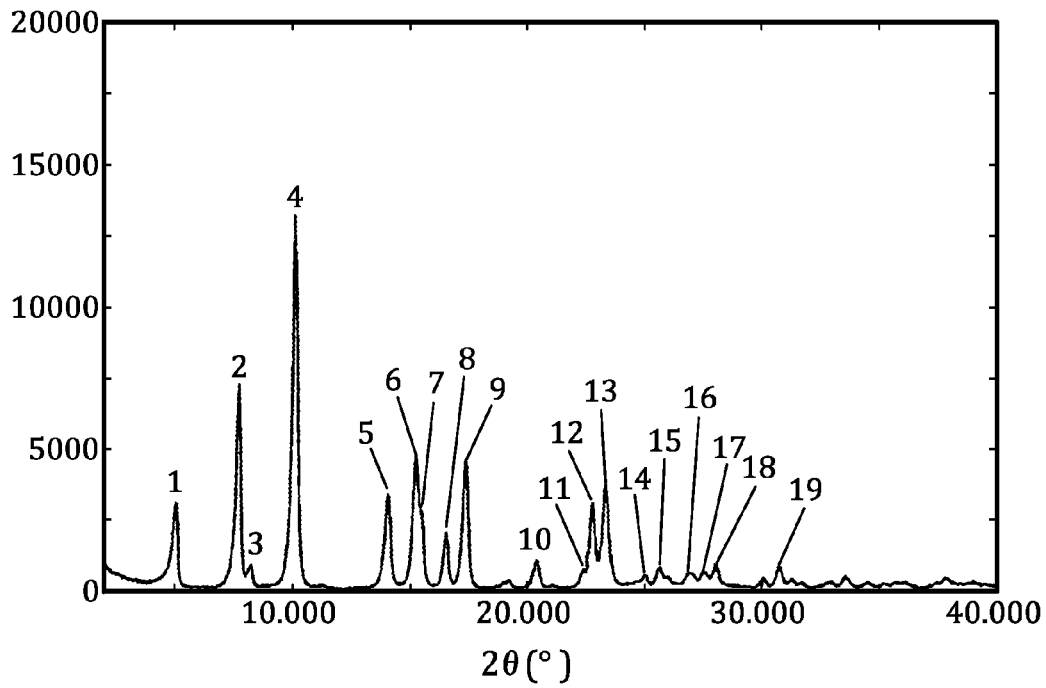
FIG. 15 shows an X-ray powder diffraction pattern of the crystal obtained in Example 15 (crystal O). The longitudinal axis of the pattern shows diffraction intensity as a count/sec (cps) unit, and the horizontal axis shows the value of the angle of diffraction 2θ.

Another preferred form of the crystal of the present invention is a crystal (crystal O) having the X-ray diffraction pattern shown in FIG. 15, in an X-ray powder diffraction pattern obtained by irradiation with copper Kα radiation (wavelength λ=1.54 angstroms). In addition, crystal O is also a crystal that shows principal peaks at angles of diffraction 2θ of 5.02, 7.70, 8.22, 10.12, 14.06, 15.24, 15.50, 16.54, 17.36, 20.38, 22.36, 22.76, 23.32, 25.02, 25.60, 26.90, 27.54, 28.04 and 30.72 in an X-ray powder diffraction pattern obtained by irradiation with copper Kα radiation (wavelength λ=1.54 angstroms). The term "principal peak" is used herein to mean a peak with a relative intensity of 5 or greater, when the maximum peak intensity is set at 100 in the X-ray powder diffraction pattern.

Figure 16:
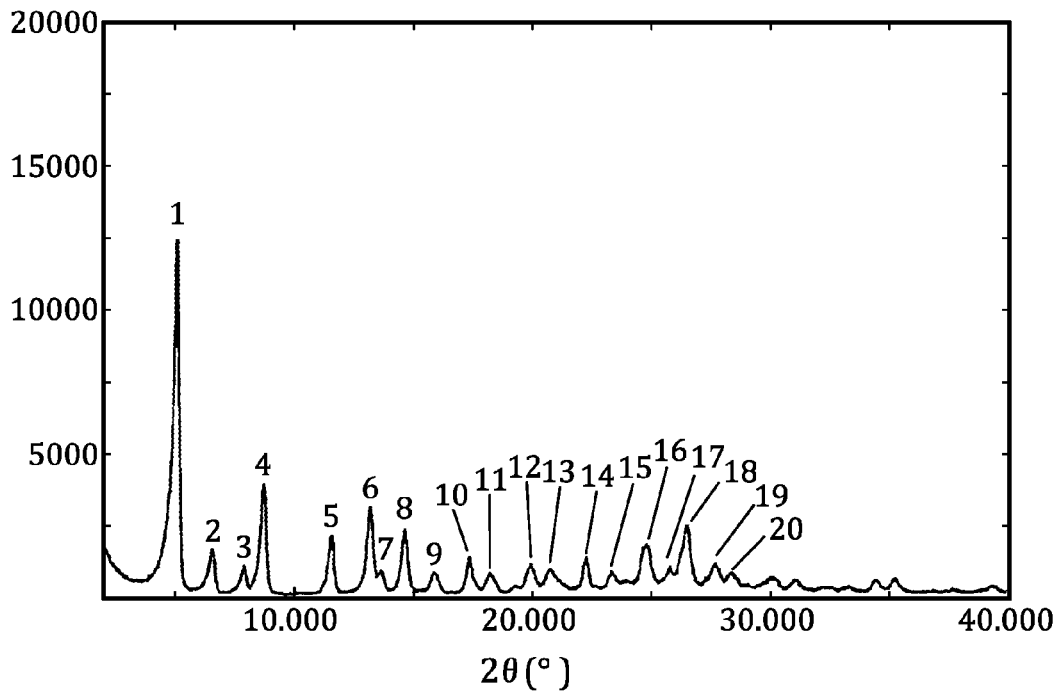
FIG. 16 shows an X-ray powder diffraction pattern of the crystal obtained in Example 16 (crystal P). The longitudinal axis of the pattern shows diffraction intensity as a count/sec (cps) unit, and the horizontal axis shows the value of the angle of diffraction 2θ.

Another preferred form of the crystal of the present invention is a crystal (crystal P) having the X-ray diffraction pattern shown in FIG. 16, in an X-ray powder diffraction pattern obtained by irradiation with copper Kα radiation (wavelength λ=1.54 angstroms). In addition, crystal P is also a crystal that shows principal peaks at angles of diffraction 2θ of 5.08, 6.56, 7.90, 8.72, 11.58, 13.18, 13.64, 14.64, 15.86, 17.34, 18.20, 19.94, 20.72, 22.24, 23.32, 24.78, 25.76, 26.48, 27.64 and 28.34 in an X-ray powder diffraction pattern obtained by irradiation with copper Kα radiation (wavelength λ=1.54 angstroms). The term "principal peak" is used herein to mean a peak with a relative intensity of 7 or greater, when the maximum peak intensity is set at 100 in the X-ray powder diffraction pattern.

Among the above described principal peaks of crystals A to P of the present invention, the peaks shown in the following table are considered to be peaks characteristic of their crystalline polymorphism. Accordingly, the crystals A to P of the present invention can be individually identified by the peaks shown in the following table.

TABLE 1

| Crystalline form | Characteristic X-ray diffraction (XRD) peak |
| --- | --- |
| Crystal A | 3.10, 4.02 |
| Crystal B | 11.16 |
| Crystal C | 16.58, 17.44 |
| Crystal D | 16.96, 20.36 |
| Crystal E | 19.36 |
| Crystal F | 6.06 |
| Crystal G | 15.90, 20.62 |
| Crystal H | 24.80, 25.40 |
| Crystal I | 22.34, 23.16 |
| Crystal J | 15.92, 20.60 |
| Crystal K | 18.50 |
| Crystal L | 7.46, 12.68 |
| Crystal M | 16.32, 23.10 |
| Crystal N | 3.10, 4.00 |
| Crystal O | 17.36, 23.32 |
| Crystal P | 13.18 |

The crystal of the present invention is also useful as an intermediate for the production of various types of salts of the compound (I).

Other embodiments of the present invention are a medicament comprising a crystal of the present invention as an active ingredient, and an antitumor agent comprising a crystal of the present invention. Another embodiment of the present invention also relates to a pharmaceutical composition comprising a crystal of the present invention.

The medicament comprising a crystal of the present invention as an active ingredient is preferably provided in the form of a pharmaceutical composition comprising a crystal of a present invention and one or two or more pharmaceutically acceptable carriers. The dosage form of the medicament of the present invention is not particularly limited, and the present medicament can be administered orally or parenterally. It is preferably administered orally.

The pharmaceutical composition of the present invention comprises at least a portion of a crystal of the present invention as a compound (I). The present pharmaceutical composition may also include a crystalline form other than a crystal of the invention of the present application as a compound (I). The ratio of a crystal of the invention of the present application in the present pharmaceutical composition may be in the range from 0.01% by weight to 99.9% by weight, for example, 0.01% by weight or more, 0.05% by weight or more, 0.1% by weight or more, 0.5% by weight or more, 1% by weight or more, 2% by weight or more, 3% by weight or more, 4% by weight or more, 5% by weight or more, 10% by weight or more, 20% by weight or more, 30% by weight or more, 40% by weight or more, 50% by weight or more, 60% by weight or more, 70% by weight or more, 80% by weight or more, 90% by weight or more, 95% by weight or more, 96% by weight or more, 97% by weight or more, 98% by weight or more, 99% by weight or more, 99.5% by weight or more, 99.6% by weight or more, 99.7% by weight or more, 99.8% by weight or more, or 99.9% by weight or more, based on the total weight of the compound (I) in the present pharmaceutical composition. The presence or absence of a crystal of the invention of the present application in the pharmaceutical composition can be confirmed by instrumental analysis methods described in the present specification (e.g. X-ray powder diffraction, thermal analysis, infrared absorption spectrum, etc.).

The crystal of the present invention can be used as an HSP90 inhibitor, an agent for inhibiting the ATPase activity of HSP90, or an agent for inhibiting the binding of HSP90 to ATP. Thus, it can be used as a medicament comprising the crystal of the present invention, and particularly preferably as an anticancer agent.

The ATPase activity of HSP90 can be examined by an ATPase assay commonly used by a person skilled in the art. For example, the ATPase activity of HSP90 can be detected using a recombinant HSP90 protein and ATP in the presence or absence of the test compound. Alternatively, in an ATPase assay, the method described in Analytical Biochemistry 327, 176-183 (2004) or Nature 425, 407-410 (2003) may be suitably performed, for example.

Inhibition of the expression of HSP90 can be examined by Northern blotting, Western blotting, ELISA or the like commonly used by a person skilled in the art. For example, mRNA is collected from cells cultured in the presence or absence of the test compound to perform Northern blotting. When the amount of HSP90 mRNA in mRNA collected from the cells cultured in the presence of the test compound is reduced from that in mRNA collected from the cells cultured in the absence of the test compound, the test compound is identified as a compound inhibiting the expression of HSP90. Alternatively, the amount of HSP90 protein may be suitably examined by performing Western blotting using the method described in Cancer. Res. 65, 6401-6408 (2005), for example.

Inhibition of binding of HSP90 to a client protein can be examined by immunoprecipitation and Western blotting commonly used by a person skilled in the art, for example. In immunoprecipitation and Western blotting, the method described in J. Biol. Chem. 277, 10346-10353 (2002) may be suitably performed, for example.

The compound inhibiting binding of HSP90 to co-chaperones or immunophilins can be examined by immunoprecipitation and Western blotting commonly used by a person skilled in the art, for example. Binding of HSP90 to co-chaperones or immunophilins may be suitably examined in the presence or absence of the test compound by performing the method described in Nature 425, 407-410 (2003), for example.

Inhibition of binding of HSP90 to ATP can be examined by a test for binding of labeled ATP to HSP90, for example. Binding of HSP90 to labeled ATP may be suitably examined in the presence or absence of the test compound by performing the method described in J. Biol. Chem. 272, 18608-18613 (1997), for example.

Inhibition of the conformational change of HSP90 can be examined by a conformational assay using bis-ANS (1,1'-bis (4-anilino-5-naphthalenesulfonic acid)), for example. In the conformational assay, the method described in J. Med. Chem. 47, 3865-3873 (2004) may be suitably performed, for example.

Cell growth inhibitory activity can be examined using a growth inhibition test method that is commonly used by a person skilled in the art. The cell growth inhibition activity can be determined by, for example, comparing the levels of cellular growth (for example, tumor cells) in the presence or absence of a test compound as described in the following Test Example 2. The growth level can be examined using a test system for assaying living cells. Examples of the method for assaying living cells include a [$^3$H]-thymidine uptake test, a BrdU method and an MTT assay.

Moreover, in vivo antitumor activity can be examined using a method for testing antitumor activity commonly used by a person skilled in the art. For example, various types of tumor cells are transplanted into a mouse, a rat or the like, and after the confirmation of the survival of the transplanted cells, the compound of the present invention is administered to the animal via oral administration, intravenous administration, etc. Thereafter, several days to several weeks later, the growth of tumor in an agent non-administration group is compared with that in a compound administration group, so as to confirm the in vivo antitumor activity of the compound of the present invention.

The crystal of the present invention can be used for treatment of tumors or cancers, such as lung cancer, gastrointestinal cancer, ovarian cancer, uterine cancer, breast cancer, liver cancer, head and neck cancer, blood cancer, renal cancer, testicular neoplasm, prostate cancer, multiple myeloma, skin cancer such as malignant melanoma, sarcoma, for example.

Since the crystal of the present invention has HSP90 inhibitory action, it can be used for treatment of cancer in which HSP90 dependency is increased. Such cancers in which HSP90 dependency is increased include cancer in which an HSP90 client protein(s) is excessively expressed, cancer in which an HSP90 client protein(s) is mutated, and the like. More specific examples include cancer in which Her2, c-Met, Flt3 or the like is excessively expressed, and cancer in which c-kit, PDGFR, Raf or the like is mutated. However, examples are not limited thereto.

Furthermore, many factor groups associated with cancer (RAS-MAPK, PI3K, telomerase, etc.) are present downstream of HSP90. If HSP90 is inhibited, signalling to such factors is also inhibited. As a result, the activation of the aforementioned factors is also inhibited. Thus, from this viewpoint as well, the hydrochloride or the crystal of the present invention that is an HSP90 inhibitor can be preferably used for treatment of various types of cancers.

The pharmaceutical composition of the present invention comprises a crystal of the present invention and a pharmaceutically acceptable carrier. It can be used as various types of injections such as an intravenous injection, an intramuscular injection or a subcutaneous injection, or it can be administered by various methods such as oral administration or a percutaneous administration. The pharmaceutically acceptable carrier refers to a pharmaceutically acceptable material (for example, an excipient, a diluent, an additive, a solvent, etc.), which is associated with the transportation of the crystal of the present invention or a composition comprising the crystal of the present invention from a certain apparatus or organ to another apparatus or organ.

As a method for preparing a formulation, a suitable formulation (for example, an oral formulation or an injection) is selected, and a commonly used method for preparing various types of formulations can be applied depending on the administration method. Examples of oral formulations include tablets, powders, granules, capsules, pills, troches, solutions, syrups, elixirs, emulsions, and oily or aqueous suspensions. In the case of oral administration, the agent may be either a free form or a salt form. The aqueous formulation can be produced by forming an acid adduct with a pharmaceutically acceptable acid or forming a salt of an alkali metal such as sodium. When the formulation is an injection, a stabilizer, a preservative, a solubilizer or the like can also be used in the formulation. The injection may be provided as a formulation to be prepared before use by storing a solution which may contain such an adjuvant or the like in a container and then converting it to a solid formulation by lyophilization or the like. One dose may be stored in one container, or multiple doses may be stored in one container.

Examples of solid formulations include tablets, powders, granules, capsules, pills and troches. These solid formulations may contain a pharmaceutically acceptable additive together with the crystal of the present invention. Examples of the additive include fillers, bulking agents, binders, disintegrants, solubilizers, wetting agents and lubricants. These can be selectively mixed as necessary to provide a formulation.

Examples of liquid formulations include solutions, syrups, elixirs, emulsions and suspensions. These liquid formulations may contain a pharmaceutically acceptable additive together with the crystal of the present invention. Examples of the additive include suspending agents and emulsifiers. These can be selectively mixed as necessary to provide a formulation.

The crystal of the present invention can be used together with other antitumor agents. Examples of such other antitumor agents include an antitumor antibiotic, an antitumor plant ingredient, BRM (biological response modifier), hormone, vitamin, an antitumor antibody, a molecular-targeted agent, and other antitumor agents.

More specifically, examples of an alkylating agent include: alkylating agents such as nitrogen mustard, nitrogen mustard N-oxide, or chlorambucil; aziridine alkylating agents such as carboquone or thiotepa; epoxide alkylating agents such as dibromomannitol or dibromodulcitol; nitrosourea alkylating agents such as carmustine, lomustine, semustine, nimustine hydrochloride, streptozocin, chlorozotocin, or ranimustine; busulphan; improsulfan tosilate; and Dacarbazine.

Examples of various types of antimetabolites include: purine antimetabolites such as 6-mercaptopurine, 6-thioguanine, or thioinosine; pyrimidine antimetabolites such as fluorouracil, tegafur, tegafur-uracil, carmofur, doxifluridine, broxuridine, cytarabine, or enocitabine; and antifolics such as methotrexate or trimethotrexate.

Examples of an antitumor antibiotic include: anthracycline antibiotic antitumor agents such as mitomycin C, bleomycin, peplomycin, daunorubicin, aclarubicin, doxorubicin, pirarubicin, THP-adriamycin, 4'-epidoxorubicin, or epirubicin; chromomycin A3; and actinomycin D.

Examples of an antitumor plant ingredient include: vinca alkaloids such as vindesine, vincristine, or vinblastine; taxanes such as paclitaxel or docetaxel; and epipodophyllotoxins such as etoposide or teniposide.

Examples of a BRM include a tumor necrosis factor and indomethacin.

Examples of a hormone include hydrocortisone, dexamethasone, methylprednisolone, prednisolone, prasterone, betamethasone, triamcinolone, oxymetholone, nandrolone, methenolone, fosfestrol, ethinyl estradiol, chlormadinone, and medroxyprogesterone.

Examples of a vitamin include vitamin C and vitamin A.

Examples of an antitumor antibody and the molecular-targeted agent include trastuzumab, rituximab, cetuximab, nimotuzumab, denosumab, bevacizumab, infliximab, imatinib mesylate, gefitinib, erlotinib, sunitinib, lapatinib, and sorafenib.

Examples of other antitumor agents include cisplatin, carboplatin, oxaliplatin, tamoxifen, camptothecin, ifosfamide, cyclophosphamide, melphalan, L-asparaginase, aseclatone, schizophyllan, picibanil, procarbazine, pipobroman, neocarzinostatin, hydroxyurea, ubenimex, and krestin.

The present invention includes a method for preventing cancer and/or a method for treating cancer, which comprises the administration of a crystal of the present invention.

The dose of the pharmaceutical composition comprising a crystal of the present invention as an active ingredient is not particularly limited. It can be selected, as appropriate, depending on various conditions such as the age, body weight, and symptoms of the patient. It is desired that the active ingredient of the pharmaceutical composition is administered to an adult in a daily dose range of 1 mg to 1000 mg, preferably 5 mg to 500 mg, more preferably 5 mg to 300 mg, and even more preferably 5 mg to 100 mg, once or divided over several administrations per day, and preferably once or twice per day, depending on symptoms.

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (free form) and a salt thereof, which are raw materials for the crystal of the present invention, can be produced, for example, in accordance with reference examples as described below.

The present invention will be described in detail in the following examples.

EXAMPLES

Reference Example 1

Production of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (free form)

(1) 1-(2-Amino-4,6-dichloropyrimidin-5-yl)-3-buten-1-ol

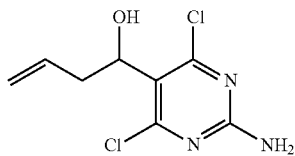

Indium powder (0.23 g) and zinc powder (1.31 g) were added to a mixture composed of commercially available 2-amino-4,6-dichloropyrimidine-5-carboaldehyde (1.92 g) and N,N-dimethylformamide (20 ml). Thereafter, sodium iodide (0.15 g) and allyl bromide (1.73 ml) were added to the mixture at room temperature. The resulting mixture was stirred for 3 hours. Thereafter, the reaction mixture was filtered through celite, and ethyl acetate was then added to the filtrate. The resulting mixture was successively washed with 1 N hydrochloric acid and a saturated saline in this order. The organic layer was dried over anhydrous sodium sulfate, and was then concentrated. Thereafter, hexane was added to the residue, and a precipitate was then collected by filtration, so as to obtain the above title compound (1.75 g) as a solid.

$^1$H-NMR (DMSO-D$_6$) δ: 2.55-2.69 (2H, m), 4.95-5.09 (3H, m), 5.37 (1H, d, J=4.1 Hz), 5.67-5.77 (1H, m), 7.42 (2H, s).

(2) 1-(2-Amino-4,6-dichloropyrimidin-5-yl)-2-(2,2-dimethyl-[1,3]dioxolan-4-yl)ethan-1-ol

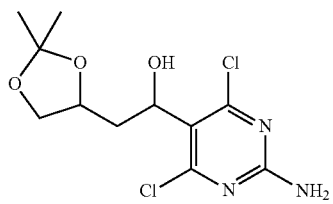 [SMILES: CC1(C)OCC(CC(O)c2c(Cl)nc(N)nc2Cl)O1]

A mixture composed of 1-(2-amino-4,6-dichloropyrimidin-5-yl)-3-buten-1-ol (57.24 g), N-methylmorpholine-N-oxide (147.6 g), tetrahydrofuran (500 ml), acetone (500 ml), water (500 ml) and osmium tetroxide (62 mg) was stirred at room temperature for 2 days. After the disappearance of the materials had been confirmed, a saturated aqueous sodium thiosulfate solution (1 L) was added to the reaction solution, and the reaction mixture was then concentrated to approximately 1.5 L under reduced pressure. The residue was saturated with sodium chloride, followed by extraction with tetrahydrofuran. The organic layer was dried over anhydrous sodium sulfate. After filtration, the filtrate was concentrated under reduced pressure, and the solvent was then distilled away. N,N-Dimethylformamide (500 ml), 2,2-dimethoxypropane (210 ml) and p-toluenesulfonic acid monohydrate (18.61 g) were added to the resulting residue. The resulting mixture was stirred at room temperature for 14 hours. A saturated sodium bicarbonate solution (1 L) and water (1 L) were added to the reaction mixture, followed by extraction with ethyl acetate. The organic layer was successively washed with water and saturated saline in this order, and it was then dried over anhydrous sodium sulfate. After filtration, the filtrate was concentrated to about 100 ml under reduced pressure. Hexane was added to the residue, and the precipitate was then collected by filtration, so as to obtain the title compound (53.88 g) as a solid.

$^1$H-NMR (DMSO-D$_6$) δ: 1.22-1.32 (6H, m), 1.72-2.23 (2H, m), 2.50 (1H, s), 3.50 (1H, td, J=14.2, 6.9 Hz), 4.22-3.92 (2H, m), 5.06-5.36 (2H, m), 7.43 (2H, d, J=12.8 Hz).

ESI-MS m/z: 308 (M+H)$^+$.

(3) 1-(2-Amino-4,6-dichloropyrimidin-5-yl)-2-(2,2-dimethyl-[1,3]dioxolan-4-yl)ethan-1-one

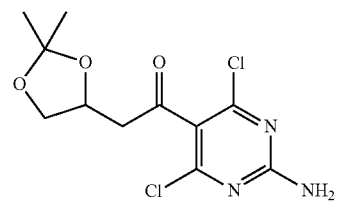 [SMILES: CC1(C)OCC(CC(=O)c2c(Cl)nc(N)nc2Cl)O1]

Acetic anhydride (149 ml) was added dropwise to a mixture composed of the above 1-(2-amino-4,6-dichloropyrimidin-5-yl)-2-(2,2-dimethyl-[1,3]dioxolan-4-yl)ethan-1-ol (74.70 g) and dimethyl sulfoxide (600 ml) at room temperature over 15 minutes under cooling in an ice bath. The reaction mixture was then stirred at the same temperature as above for 18 hours. After the disappearance of the materials had been confirmed, the reaction solution was poured into ice water. The precipitated solid was collected by filtration, so as to obtain the title compound (68.26 g).

$^1$H-NMR (CDCl$_3$) δ: 1.37 (3H, s), 1.42 (3H, s), 2.98-3.06 (1H, m), 3.32-3.40 (1H, m), 3.67-3.72 (1H, m), 4.25-4.30 (1H, m), 4.57-4.64 (1H, m), 5.72 (2H, s).

ESI-MS m/z: 306 (M+H)⁺.

(4) 4-Chloro-3-[(2,2-dimethyl-1,3-dioxolan-4-yl)methyl]-1-(4-methoxybenzyl)-1H-pyrazolo[3,4-d]pyrimidine-6-amine

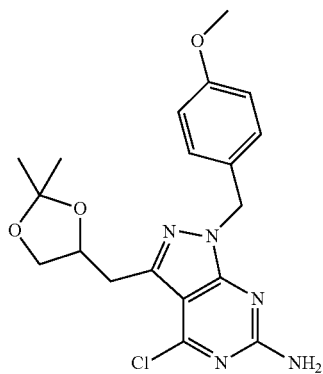 [SMILES: COc1ccc(Cn2nc(CC3COC(C)(C)O3)c3c(Cl)nc(N)nc32)cc1]

Triethylamine (83.68 ml) was added to a mixture composed of the above 1-(2-amino-4,6-dichloropyrimidin-5-yl)-2-(2,2-dimethyl-[1,3]dioxolan-4-yl)ethan-1-one (61.23 g), (4-methoxybenzyl)-hydrazine hydrochloride (41.50 g) produced by the method described in U.S. Patent No. US2003/18197, and dichloromethane (600 ml) over 30 minutes under cooling in an ice bath. Thereafter, while the temperature of the reaction solution was gradually raised, it was stirred for 17 hours. Thereafter, a 10% citric acid aqueous solution was added to the reaction mixture, followed by extraction with dichloromethane. The organic layer was dried over anhydrous sodium sulfate and was then concentrated under reduced pressure. A 5% citric acid aqueous solution was added to the resulting residue, and the precipitate was then collected by filtration. The resultant was washed with water, so as to obtain the title compound (73.84 g) as a solid.

¹H-NMR (CDCl₃) δ: 1.36 (3H, s), 1.43 (3H, s), 3.11 (1H, dd, J=14.7, 8.1 Hz), 3.43 (1H, dd, J=14.7, 5.2 Hz), 3.73-3.78 (4H, m), 4.08 (1H, dd, J=8.1, 6.0 Hz), 4.54-4.61 (1H, m), 4.77 (2H, brs), 5.22 (2H, s), 6.83 (2H, d, J=8.5 Hz), 7.24 (2H, d, J=8.5 Hz).

ESI-MS m/z: 404 (M+H)⁺.

(5) Di-tert-butyl{4-chloro-3-[(2,2-dimethyl-1,3-dioxolan-4-yl)methyl]-1-(4-methoxybenzyl)-1H-pyrazolo[3,4-d]pyrimidin-6-yl}imide dicarbonate

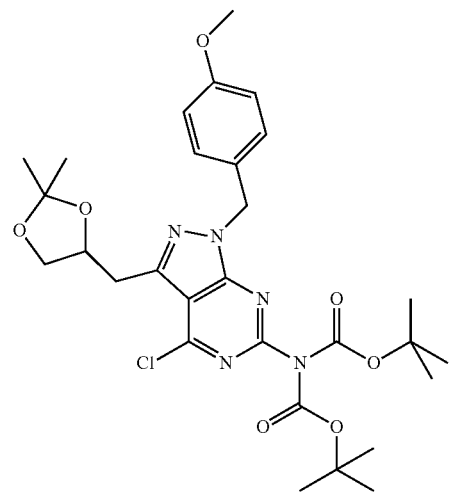 [SMILES: COc1ccc(Cn2nc(CC3COC(C)(C)O3)c3c(Cl)nc(N(C(=O)OC(C)(C)C)C(=O)OC(C)(C)C)nc32)cc1]

4-Dimethylaminopyridine (2.20 g) and di-tert-butyl dicarbonate (86.59 g) were added to a mixture composed of the above 4-chloro-3-[(2,2-dimethyl-1,3-dioxolan-4-yl)methyl]-1-(4-methoxybenzyl)-1H-pyrazolo[3,4-d]pyrimidine-6-amine (72.83 g) and tetrahydrofuran (700 ml), and the resulting mixture was then stirred at room temperature for 12 hours. Thereafter, the reaction mixture was filtered, and the filtrate was then concentrated under reduced pressure. The resulting residue was purified by silica gel column chromatography (ethyl acetate-hexane), so as to obtain the title compound (70.00 g) as an amorphous substance.

¹H-NMR (CDCl₃) δ: 1.37 (3H, s), 1.40 (3H, s), 1.44-1.46 (18H, m), 3.21-3.29 (1H, m), 3.48-3.55 (1H, m), 3.74-3.81 (4H, m), 4.09-4.15 (1H, m), 4.58-4.66 (1H, m), 5.48 (2H, dd, J=17.3, 15.1 Hz), 6.81 (2H, d, J=7.8 Hz), 7.27-7.30 (2H, m).

ESI-MS m/z: 604 (M+H)+.

(6) Di-tert-butyl[4-chloro-3-(2,3-dihydroxypropyl)-1-(4-methoxybenzyl)-1H-pyrazolo[3,4-d]pyrimidin-6-yl]imide dicarbonate

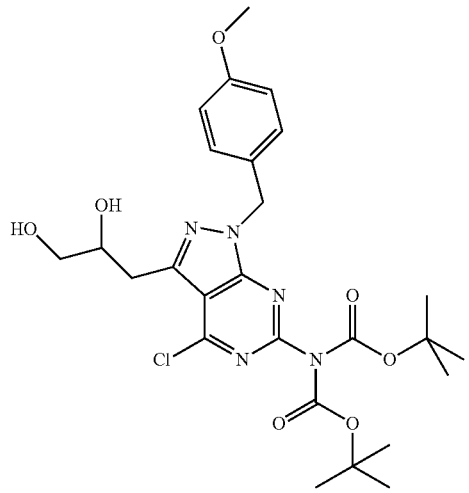 [SMILES: COc1ccc(Cn2nc(CC(O)CO)c3c(Cl)nc(N(C(=O)OC(C)(C)C)C(=O)OC(C)(C)C)nc32)cc1]

The above di-tert-butyl{4-chloro-3-[(2,2-dimethyl-1,3-dioxolan-4-yl)methyl]-1-(4-methoxybenzyl)-1H-pyrazolo[3,4-d]pyrimidin-6-yl}imide dicarbonate (53.85 g) was dissolved in acetonitrile (500 ml), and copper(II) chloride dihydrate (30.39 g) was then added to the solution. The resulting mixture was stirred at room temperature for 2 hours. Thereafter, a saturated ammonium chloride aqueous solution was added to the reaction solution, followed by extraction with ethyl acetate. The organic layer was washed with saturated saline, and it was then dried over anhydrous sodium sulfate, followed by concentration under reduced pressure. The resulting residue was purified by silica gel column chromatography (ethyl acetate-hexane), so as to obtain the title compound (37.70 g) as an amorphous substance.

$^1$H-NMR (CDCl$_3$) δ: 1.46 (18H, s), 3.15 (1H, d, J=3.7 Hz), 3.23-3.33 (2H, m), 3.62-3.82 (5H, m), 4.26-4.34 (1H, m), 5.49 (2H, t, J=15.9 Hz), 6.82 (2H, d, J=8.1 Hz), 7.25-7.30 (2H, m).

ESI-MS m/z: 564 (M+H)+.

(7) Di-tert-butyl[8-hydroxy-2-(4-methoxybenzyl)-2,7,8,9-tetrahydro-6-thia-1,2,3,5-tetraazabenzo[cd]azulen-4-yl]imide dicarbonate

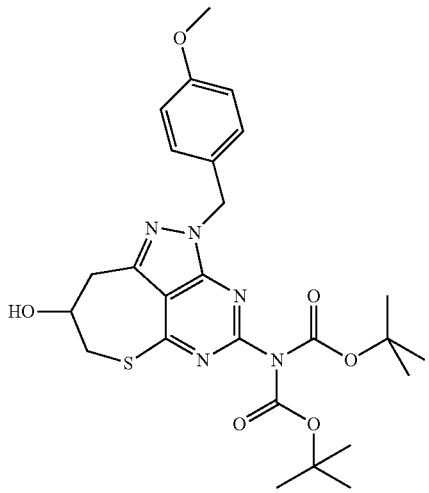 [SMILES: COc1ccc(Cn2nc3c4c(nc(N(C(=O)OC(C)(C)C)C(=O)OC(C)(C)C)nc42)SCC(O)C3)cc1]

Methanesulfonyl chloride (4.23 ml) was added dropwise to a mixture composed of the above di-tert-butyl[4-chloro-3-(2,3-dihydroxypropyl)-1-(4-methoxybenzyl)-1H-pyrazolo[3,4-d]pyrimidin-6-yl]imide dicarbonate (28.00 g), 2,4,6-collidine (16.53 ml) and anhydrous dichloromethane (400 ml) under cooling in an ice bath. The resulting mixture was then stirred at 4° C. for 15 hours. Thereafter, a 10% citric acid aqueous solution was added to the reaction mixture, followed by extraction with dichloromethane. The organic layer was dried over anhydrous sodium sulfate, and it was then concentrated under reduced pressure. The resulting residue was dissolved in N,N-dimethylformamide (300 ml), and sodium hydrogensulfide monohydrate (5.52 g) was then added to the solution under cooling in an ice bath. Thereafter, the resulting mixture was stirred at room temperature for 1.5 hours. Thereafter, potassium carbonate (10.29 mg) was added to the reaction mixture, and the resulting mixture was then heated to 50° C., followed by a further stirring operation for 5 hours. Subsequently, ethyl acetate was added to the reaction mixture, and the resultant was then successively washed with a 10% citric acid aqueous solution and then with a saturated saline. The resultant was dried over anhydrous sodium sulfate, and it was then concentrated under reduced pressure. The resulting residue was purified by silica gel column chromatography (ethyl acetate-hexane), so as to obtain the title compound (20.59 g) as a solid.

$^1$H-NMR (CDCl$_3$) δ: 1.45 (18H, s), 2.39 (1H, brs), 3.29-3.51 (4H, m), 4.58 (1H, brs), 3.76 (3H, s), 5.42-5.49 (2H, m), 6.82 (2H, d, J=8.6 Hz), 7.30 (2H, d, J=8.6 Hz).

ESI-MS m/z: 544 (M+H)+.

(8) 4-[Bis(tert-butoxycarbonyl)amino]-2-(4-methoxybenzyl)-2,7-dihydro-6-thia-1,2,3,5-tetraazabenzo[cd]azulen-8-yl acetate

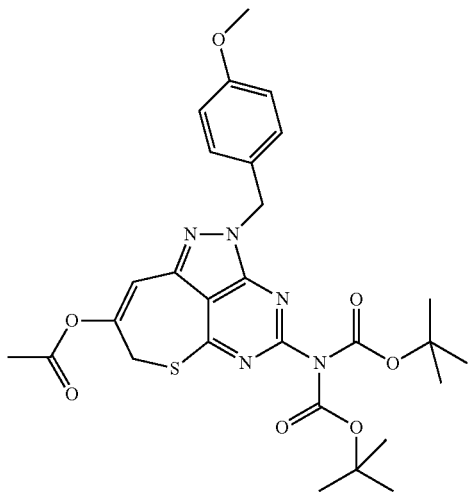 [SMILES: COc1ccc(Cn2nc3c4c(nc(N(C(=O)OC(C)(C)C)C(=O)OC(C)(C)C)nc42)SCC(OC(C)=O)=C3)cc1]

In a nitrogen atmosphere, acetic anhydride (14 ml) was added dropwise to a mixture composed of the above di-tert-butyl[8-hydroxy-2-(4-methoxybenzyl)-2,7,8,9-tetrahydro-6-thia-1,2,3,5-tetraazabenzo[cd]azulen-4-yl]imide dicarbonate (8.17 g), dimethyl sulfoxide (74 ml), and pyridine (12 ml) under cooling on ice, and the resulting mixture was then stirred for 30 minutes. Thereafter, the reaction solution was further stirred at room temperature for 15 hours. After the disappearance of the materials had been confirmed, the reaction mixture was diluted with ethyl acetate, and it was then washed with a saturated saline. The organic layer was dried over anhydrous sodium sulfate, followed by concentration under reduced pressure. The resulting residue was purified by silica gel column chromatography (ethyl acetate-hexane), so as to obtain the title compound (6.15 g) as an amorphous substance.

$^1$H-NMR (CDCl$_3$) δ: 1.44 (18H, s), 2.26 (3H, s), 3.77 (3H, s), 3.88 (2H, s), 5.50 (2H, s), 6.68 (1H, s), 6.83 (2H, d, J=8.8 Hz), 7.31 (2H, d, J=8.8 Hz).

ESI-MS m/z: 584 (M+H)+.

(9) Di-tert-butyl[2-(4-methoxybenzyl)-8-oxo-2,7,8,9-tetrahydro-6-thia-1,2,3,5-tetraazabenzo[cd]azulen-4-yl]imide dicarbonate

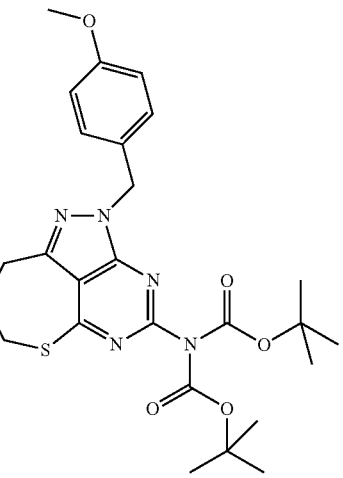

A mixture composed of the above 4-[bis(tert-butoxycarbonyl)amino]-2-(4-methoxybenzyl)-2,7-dihydro-6-thia-1,2,3,5-tetraazabenzo[cd]azulen-8-yl acetate (6.15 g), methanol (200 ml), and potassium carbonate (0.73 g) was stirred for 1.5 hours under cooling in an ice bath. After the disappearance of the materials had been confirmed, a saturated ammonium chloride aqueous solution was added to the reaction mixture, followed by extraction with ethyl acetate. The organic layer was washed with a saturated saline, and it was then dried over anhydrous sodium sulfate, followed by concentration under reduced pressure, so as to obtain the title compound (5.70 g) as an amorphous substance.

$^1$H-NMR (CDCl$_3$) δ: 1.46 (18H, s), 3.84 (2H, s), 3.77 (3H, s), 4.23 (2H, s), 5.48 (2H, s), 6.83 (2H, d, J=8.6 Hz), 7.32 (2H, d, J=8.6 Hz).

ESI-MS m/z: 542 (M+H)+.

(10) Ethyl {4-[bis(tert-butoxycarbonyl)amino]-2-(4-methoxybenzyl)-2,7-dihydro-6-thia-1,2,3,5-tetraazabenzo[cd]azulen-8-yl}acetate

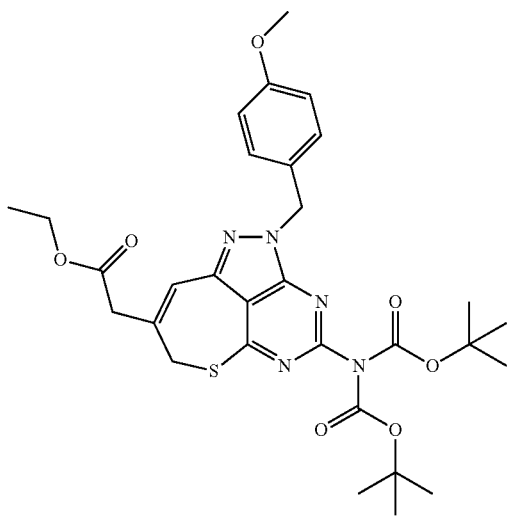 [SMILES: CCOC(=O)CC1=Cc2nn(Cc3ccc(OC)cc3)c3nc(N(C(=O)OC(C)(C)C)C(=O)OC(C)(C)C)nc(c23)SC1]

A mixture composed of the above di-tert-butyl[2-(4-methoxybenzyl)-8-oxo-2,7,8,9-tetrahydro-6-thia-1,2,3,5-tetraazabenzo[cd]azulen-4-yl]imide dicarbonate (5.19 g), ethyl (triphenylphosphanylidene)acetate (3.51 g), and toluene (300 ml) was stirred at 65° C. for 13 hours. Thereafter, the reaction mixture was concentrated under reduced pressure, and the residue was then purified by silica gel column chromatography (ethyl acetate-hexane), so as to obtain the title compound (3.78 g) as an amorphous substance.

1H-NMR (CDCl3) δ: 1.29 (3H, t, J=7.1 Hz), 1.69-1.77 (1H, m), 2.37-2.40 (1H, m), 2.46-2.52 (1H, m), 2.68-2.71 (2H, m), 4.20 (2H, q, J=7.1 Hz), 5.10-5.13 (1H, m), 5.20 (2H, brs).
ESI-MS m/z: 612 (M+H)+

(11) 2-(4-amino-2,7-dihydro-6-thia-1,2,3,5-tetraazabenzo[cd]azulen-8-yl)-N-methylacetamide trifluoroacetate

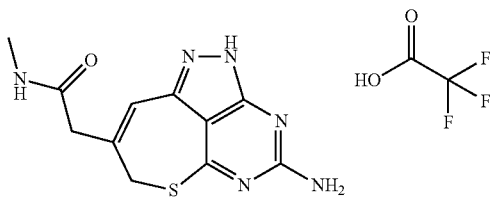 [SMILES: CNC(=O)CC1=Cc2n[nH]c3nc(N)nc(c23)SC1 ; O=C(O)C(F)(F)F]

The above ethyl {4-[bis(tert-butoxycarbonyl)amino]-2-(4-methoxybenzyl)-2,7-dihydro-6-thia-1,2,3,5-tetraazabenzo[cd]azulen-8-yl}acetate (2.2 g) was dissolved in a 40% methylamine/methanol solution (40 ml), and the mixed solution was then stirred at room temperature for 2 hours. The completion of the reaction was confirmed by LC-MS, and the solvent was then distilled away under reduced pressure. Thereafter, anisole (2 ml) and trifluoroacetic acid (40 ml) were added to the resulting residue, and the resulting mixture was then stirred at 65° C. for 15 hours. Thereafter, the reaction solution was concentrated under reduced pressure, and an isopropyl ether-ether mixed solution was then added to the residue. The precipitate was collected by filtration, so as to obtain the title compound (1.53 g) as a solid.

ESI-MS m/z: 277 (M+H)+.

(12) 5-Chloro-4-hydroxy-6-methylnicotinic acid

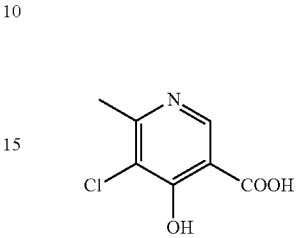

Commercially available 4-hydroxy-6-methyl-nicotinic acid (300 mg) was suspended in 3 ml of acetonitrile, and N-chlorosuccinimide (380 mg) was then added to the suspension. The resulting mixture was stirred at room temperature for 30 minutes. Thereafter, the reaction solution was heated under reflux for 45 minutes. After the disappearance of the materials had been confirmed, the reaction solution was cooled on ice, and the precipitate was then collected by filtration, so as to obtain the title compound (324 mg) as a solid.

1H-NMR (CD3OD) δ: 2.56 (3H, s), 8.50 (1H, s).
ESI-MS m/z: 188 (M+H)+

(13) Methyl 4,5-dichloro-6-methylnicotinate

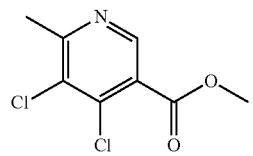

Phosphorus oxychloride (1.13 ml) was added to the above 5-chloro-4-hydroxy-6-methylnicotinic acid (320 mg), and the resulting mixture was then heated under reflux for 2 hours. Thereafter, the reaction solution was concentrated under reduced pressure, and methanol (3 ml) was then added dropwise to the residue under cooling on ice. The resulting mixture was stirred at room temperature for 30 minutes, followed by concentration under reduced pressure. A saturated sodium bicarbonate solution was added to the residue under cooling on ice, followed by extraction with ethyl acetate. The organic layer was dried over anhydrous sodium sulfate, and the solvent was then distilled away, so as to obtain a crude product of the title compound (436 mg) as a solid.

(14) Methyl 5-chloro-4-methoxy-6-methylnicotinate

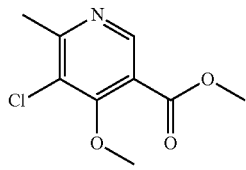

Crude methyl 4,5-dichloro-6-methylnicotinate (380 mg) was dissolved in 3 ml of methanol and, in a nitrogen stream, sodium methoxide (120 mg) was then added to the solution under cooling on ice. The temperature of the reaction solution was gradually raised to room temperature, and it was stirred for 18 hours. After the disappearance of the materials had been confirmed, a saturated ammonium chloride aqueous solution was added to the reaction solution under cooling on ice, followed by extraction with chloroform. The organic layer was dried over anhydrous sodium sulfate, and the solvent was then distilled away. The residue was purified by silica gel chromatography (ethyl acetate-hexane), so as to obtain the title compound (210 mg) as a solid.

1H-NMR (CDCl$_3$) δ: 2.67 (3H, s), 3.95 (4H, s), 4.00 (3H, s), 8.76 (1H, s).

ESI-MS m/z: 216 (M+H)+

(15) (5-Chloro-4-methoxy-6-methylpyridin-3-yl)methanol

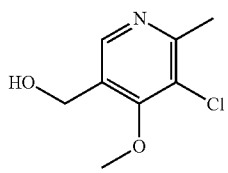

The above methyl 5-chloro-4-methoxy-6-methylnicotinate (1.0 g) was dissolved in 30 ml of methanol, and sodium borohydride (1.75 g) was then added to the solution. The resulting mixture was heated under reflux for 1 hour. Thereafter, a saturated ammonium chloride aqueous solution was added to the reaction solution under cooling on ice, followed by extraction with chloroform three times. The organic layer was dried over anhydrous sodium sulfate, and the solvent was then distilled away, so as to obtain the title compound (0.92 g) as an oily substance.

1H-NMR (CDCl$_3$) δ: 2.63 (3H, s), 4.00 (3H, s), 4.71 (2H, brs), 8.33 (1H, s)

ESI-MS m/z: 220 (M+H)+

(16) 3-Chloro-5-(chloromethyl)-4-methoxy-2-methylpyridine

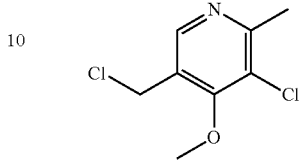

The above (5-chloro-4-methoxy-6-methylpyridin-3-yl)methanol (520 mg) was dissolved in 20 ml of chloroform, and thionyl chloride (0.38 ml) was then added to the solution under cooling on ice. The resulting mixture was stirred at the same temperature as above for 3 hours. Thereafter, the reaction solution was concentrated, and ethyl acetate was then added to the concentrate. The resulting mixture was washed with saturated sodium bicarbonate solution, water, and saturated saline in this order. The organic layer was dried over anhydrous sodium sulfate, and the solvent was then distilled away. The residue was purified by silica gel chromatography (ethyl acetate-hexane), so as to obtain the title compound (550 mg) as an oily substance.

1H-NMR (CDCl$_3$) δ: 2.64 (3H, s), 4.05 (3H, s), 4.61 (2H, s), 8.35 (1H, s).

ESI-MS m/z: 206 (M+H)+

(17) 3-Chloro-4-methoxy-2,5-dimethylpyridine

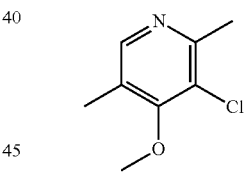

The above 3-chloro-5-(chloromethyl)-4-methoxy-2-methylpyridine (550 mg) was dissolved in 10 ml of methanol, and 10% Pd carbon (50 mg) was then added to the solution. Normal-pressure contact hydrogenation was performed on the mixture under cooling on ice for 3 hours. Thereafter, the catalyst was removed by filtration, and methanol was then distilled away under reduced pressure. The residue was extracted with chloroform. The organic layer was washed with a saturated sodium bicarbonate solution, and it was then dried over anhydrous sodium sulfate. The solvent was distilled away, and the residue was purified by silica gel chromatography (ethyl acetate-hexane), so as to obtain the title compound (365 mg) as an oily substance.

1H-NMR (CDCl$_3$) δ: 2.25 (3H, s), 2.59 (3H, s), 3.89 (3H, s), 8.16 (1H, s).

ESI-MS m/z: 172 (M+H)+

(18) 3-Chloro-4-methoxy-2,5-dimethylpyridine 1-oxide

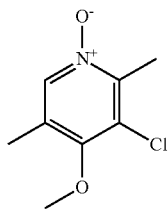

The above 3-chloro-4-methoxy-2,5-dimethylpyridine (181 mg) was dissolved in 5 ml of dichloromethane, and urea peroxide (169 mg) and phthalic anhydride (219 mg) were then added to the solution. The resulting mixture was stirred at room temperature for 2.5 hours. Thereafter, a saturated aqueous sodium thiosulfate solution was added to the reaction solution under cooling on ice, and the resulting mixture was then diluted with chloroform. The water layer was extracted with chloroform two times. The organic layer was dried over anhydrous sodium sulfate, and the solvent was then distilled away, so as to obtain the title compound (181 mg) as a solid.

1H-NMR (CDCl$_3$) δ: 2.24 (3H, s), 2.62 (3H, s), 3.87 (3H, s), 8.07 (1H, s).

ESI-MS m/z: 188 (M+H)+

(19) (3-Chloro-4-methoxy-5-methylpyridin-2-yl)methanol

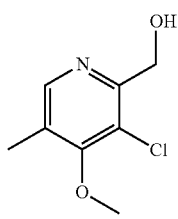

The above 3-chloro-4-methoxy-2,5-dimethylpyridine 1-oxide (530 mg) was suspended in 15 ml of dichloromethane, and trifluoroacetic anhydride (0.39 ml) was then added to the suspension under cooling on ice. The resulting mixture was stirred at room temperature for 3 hours. The reaction solution was diluted with chloroform, and was then washed with a saturated sodium bicarbonate solution. The water layer was extracted with chloroform. The organic layer was dried over anhydrous sodium sulfate, and the solvent was then distilled away, so as to obtain the title compound (521 mg) as an oily substance.

1H-NMR (CDCl$_3$) δ: 2.29 (3H, s), 3.93 (3H, s), 4.29 (1H, brs), 4.72-4.74 (2H, m), 8.26 (1H, s).

ESI-MS m/z: 188 (M+H)+

(20) 3-Chloro-2-(chloromethyl)-4-methoxy-5-methylpyridine hydrochloride

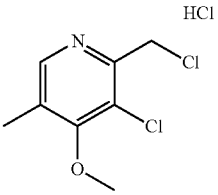

The above (3-chloro-4-methoxy-5-methylpyridin-2-yl)methanol (530 mg) was dissolved in 20 ml of chloroform, and thionyl chloride (1.03 ml) was then added dropwise to the solution under cooling on ice. The resulting mixture was stirred at room temperature for 3 hours. Thereafter, the reaction solution was concentrated, and it was then washed with a mixed solvent of ether-hexane, so as to obtain the title compound (410 mg) as a solid.

1H-NMR (CDCl$_3$) δ: 2.47 (3H, s), 4.32 (3H, s), 5.09 (2H, s), 8.54 (1H, s).

ESI-MS m/z: 206 (M+H)+

(21) 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide

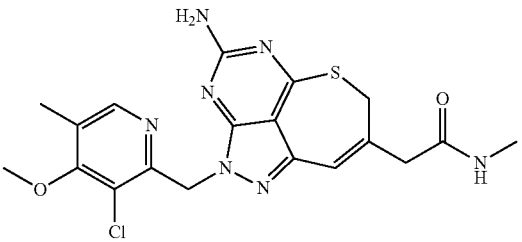

Dimethylformamide (1 ml) was added to 2-(4-amino-2,7-dihydro-6-thia-1,2,3,5-tetraazabenzo[cd]azulen-8-yl)-N-methylacetamide trifluoroacetate (28 mg), 3-chloro-2-(chloromethyl)-4-methoxy-5-methylpyridine hydrochloride (36 mg), and potassium carbonate (69 mg). The resulting mixture was stirred at 60° C. for 2.5 hours. Thereafter, the insoluble matter was removed by filtration, and the solvent was then distilled away in a nitrogen stream. The resulting residue was dissolved in dimethyl sulfoxide (1 ml), and it was then purified by preparatory reverse-phase HPLC. The solvent was distilled away under reduced pressure, so as to obtain the title compound (27.0 mg) as a solid (amorphous substance).

$^1$H-NMR (CDCl$_3$) δ: 2.24 (4H, s), 2.82 (3H, d, J=4.9 Hz), 3.27 (2H, s), 3.80 (2H, s), 3.91 (3H, s), 5.21 (2H, s), 5.65 (2H, s), 5.87 (1H, s), 6.70 (1H, s), 8.16 (1H, s).

ESI-MS m/z: 446 (M+H)$^+$.

Reference Example 2

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride 3 M Hydrochloric acid (0.786 ml, 2.358 mmol) was added to an ethanol (30 ml) suspension of 2-{4-amino-2-[(3-chloro- 4-methoxy-5-methylpyridin-2-yl)methyl]-2,7-dihydro-6-thia-1,2,3,5-tetraazabenzo[cd]azulen-8-yl}-N-methylacetamide (527.52 mg, 1.183 mmol) while stirring at 25° C., and the mixture was then stirred for 1 hour. Thereafter, the precipitated solid was filtered, was then washed with ethanol (6 ml), and was then dried under reduced pressure at 40° C. for 30 minutes, so as to obtain the above title compound (531.09 g, 1.101 mmol).

Elemental analysis values for $C_{19}H_{21}Cl_2N_7O_2S$

Calculated: C, 47.31; H, 4.39; N, 20.33; O, 6.63; Cl, 14.70; S, 6.65.

Found: C, 47.29; H, 4.40; N, 20.02; O, 6.87; Cl, 14.99; S, 6.83.

Examples will be described below. The X-ray powder diffraction was always measured using a reflective X-ray powder diffraction device (RINT-TTRIII) manufactured by Rigaku Corporation (wavelength: CuKα, λ=1.54 angstroms), with a sample filled into a non-reflective sample holder (tube voltage: 50 kV; tube current: 300 mA; scanning rate: 2° or 20°/min; each of divergence slit, scattering slit and light receiving slit: 0.5 mm; divergence longitudinal restriction slit: 5 mm; sampling width of 0.02°; incident monochromator).

As a moisture sorption/desorption measurement device, Surface Measurement System manufactured by DVS Advantage was used. Temperature was set at 25° C., and humidity was set at 0, 10, 20, 30, 40, 50, 60, 65, 70, 75, 80, 85, 90, 95, 90, 85, 80, 75, 70, 65, 60, 50, 40, 30, 25, 20, 10 and 0, or 10, 20, 30, 40, 50, 60, 65, 70, 75, 80, 85, 90, 95, 90, 85, 80, 75, 70, 65, 60, 50, 40, 30, 25, 20 and 10. The step transition condition was set within 0.006 wt. %. The minimum exposure time and the maximum exposure time were set at 15 min and 120 min, respectively.

As a differential scanning calorimeter (DSC device), DSC6220 from EXSTAR 6000 series manufactured by SII NanoTechnology Inc. was used, and the measurement was carried out at a temperature increasing rate of 10° C./min. It is to be noted that the flow rate of nitrogen gas was set at 100 mL/min.

As an infrared spectrometer (IR device), Fourier Transform Infrared Spectrometer FT/IR-6300 type A, manufactured by JASCO Corporation, was used and was equipped with a DuraScope manufactured by SensIR Technologies LLC, and the measurement was carried out by an ATR method. The measurement was carried out at a number of scanning processes of 32, at a resolving power of 4 cm$^{-1}$, and with sensitivity and interferometer speed that were set at automatic.

Example 1

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide dihydrochloride crystal A 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (crystal B obtained by the same operations as those in the method described in the following Example 2) (10.0 g, 22.43 mmol) was suspended in acetone (750 ml), and the resulting mixture was then stirred at room temperature for 4 days. A precipitate was collected by filtration, and was washed with water (50 ml). The resultant was then dried at 60° C. overnight under reduced pressure, so as to obtain the above title compound as crystal A (8.1 g, 18.16 mmol). Yield: 81%.

The elemental analysis measurement values (theoretical values) of the obtained crystal are shown below.

For 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide, C, 49.55%; (51.18%), H, 4.38%; (4.52%), O; 7.78%; (7.18%), N, 21.09%; (21.99%), Cl, 7.75%; (7.95%), and S, 7.03%; (7.19%).

A diffraction pattern from the X-ray powder diffraction (CuKα, λ=1.54 angstroms) of the obtained crystal is shown in FIG. 1, and peaks with a relative intensity of 10 or greater, when the maximum peak intensity is set at 100 in FIG. 1, are shown in Table 2.

Figure 17:
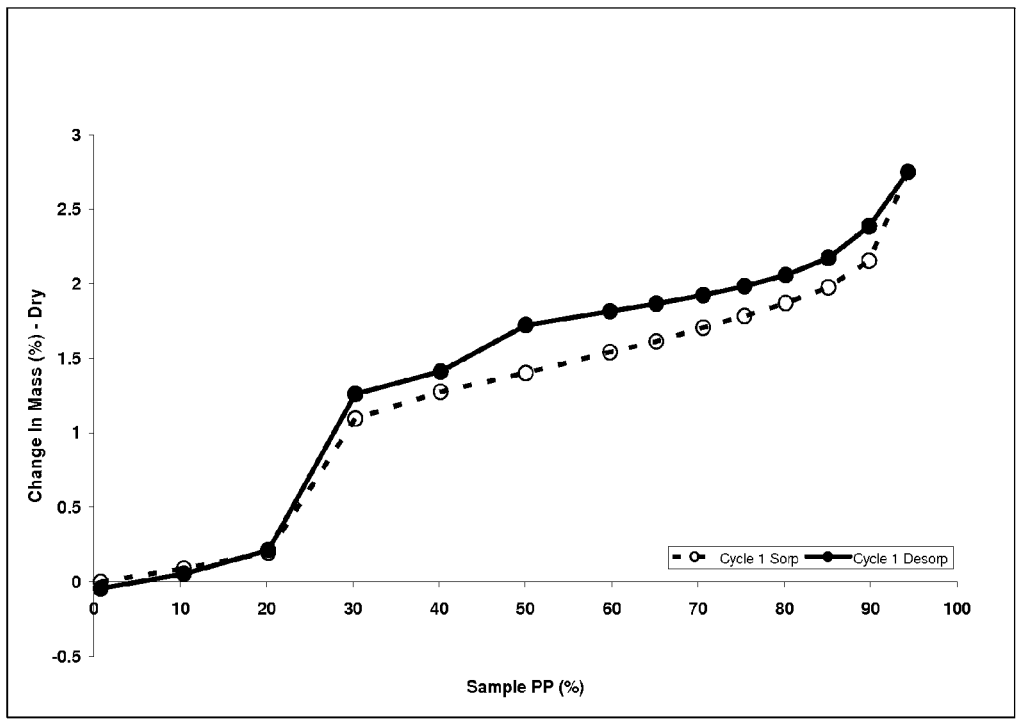
FIG. 17 shows a moisture sorption/desorption isotherm of the crystal obtained in Example 1 (crystal A). The longitudinal axis of the figure shows a change (%) in the mass of the compound, and the horizontal axis shows relative humidity (% RH). The broken line with open circles shows a moisture sorption curve, and the solid line with filled circles shows a moisture desorption curve.
Figure 26:
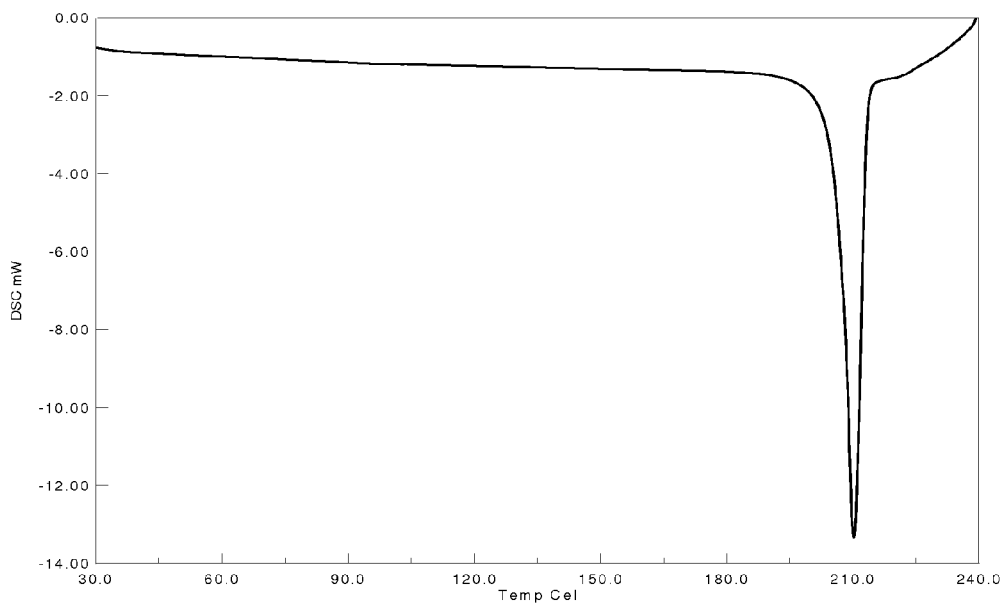
FIG. 26 shows a DSC curve of the crystal obtained in Example 1 (crystal A). The longitudinal axis of the figure shows heat flow (mW), and the horizontal axis shows temperature (° C.).
Figure 35:
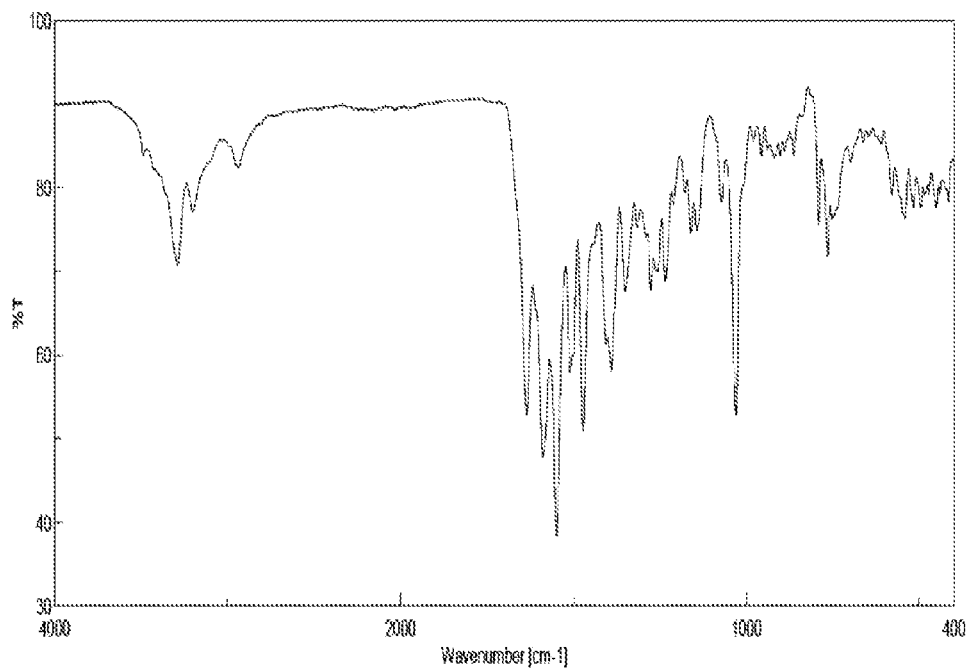
FIG. 35 shows an infrared absorption spectrum of the crystal obtained in Example 1 (crystal A). The longitudinal axis of the figure shows transmittance (% T), and the horizontal axis shows the wave number (cm$^{-1}$) of the infrared radiation applied.

A moisture sorption/desorption isotherm obtained by automatic measurement of the amount of water vapor adsorbed onto the obtained crystal is shown in FIG. 17, a DSC curve obtained by differential scanning calorimetry is shown in FIG. 26, and an infrared absorption spectrum thereof is shown in FIG. 35.

TABLE 2

| Peak No. | 2θ | d value | Relative intensity |
|---|---|---|---|
| 1 | 3.10 | 28.48 | 32 |
| 2 | 4.02 | 21.96 | 39 |
| 3 | 6.22 | 14.20 | 100 |
| 4 | 8.54 | 10.35 | 12 |
| 5 | 9.62 | 9.19 | 19 |
| 6 | 11.58 | 7.64 | 26 |
| 7 | 11.84 | 7.47 | 22 |
| 8 | 12.16 | 7.27 | 13 |
| 9 | 12.56 | 7.04 | 14 |
| 10 | 14.46 | 6.12 | 54 |
| 11 | 15.02 | 5.89 | 24 |
| 12 | 15.26 | 5.80 | 26 |
| 13 | 17.86 | 4.96 | 13 |
| 14 | 22.14 | 4.01 | 21 |
| 15 | 22.96 | 3.87 | 12 |
| 16 | 23.10 | 3.85 | 13 |
| 17 | 23.82 | 3.73 | 11 |
| 18 | 24.26 | 3.67 | 13 |
| 19 | 26.82 | 3.32 | 10 |

Example 2

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide crystal B 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (an amorphous solid obtained by the same operations as those in the method described in the above Reference Example 1) (24.4 g, 50.23 mmol) was suspended in ethanol (2500 ml), and the resulting mixture was then stirred at room temperature for 3 hours. A precipitate was collected by filtration, and was successively washed with ethanol (500 ml), water (250 ml), ethanol (500 ml), ethyl acetate (500 ml) and n-hexane (500 ml) in this order. The resultant was then dried at 60° C. overnight under reduced pressure, so as to obtain the above title compound as crystal B (18.3 g, 41.04 mmol). Yield: 75%.

The elemental analysis measurement values (theoretical values) of the obtained crystal are shown below.

For 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide, C, 50.59% (51.18%), H, 4.63%; (4.52%), O; 8.99%; (7.18%), N, 21.47%; (21.99%), Cl, 7.63%; (7.95%), and S, 6.90%; (7.19%).

A diffraction pattern from the X-ray powder diffraction (CuKα, λ=1.54 angstroms) of the obtained crystal is shown in FIG. 2, and peaks with a relative intensity of 3 or greater, when the maximum peak intensity is set at 100 in FIG. 2, are shown in Table 3.

Figure 18:
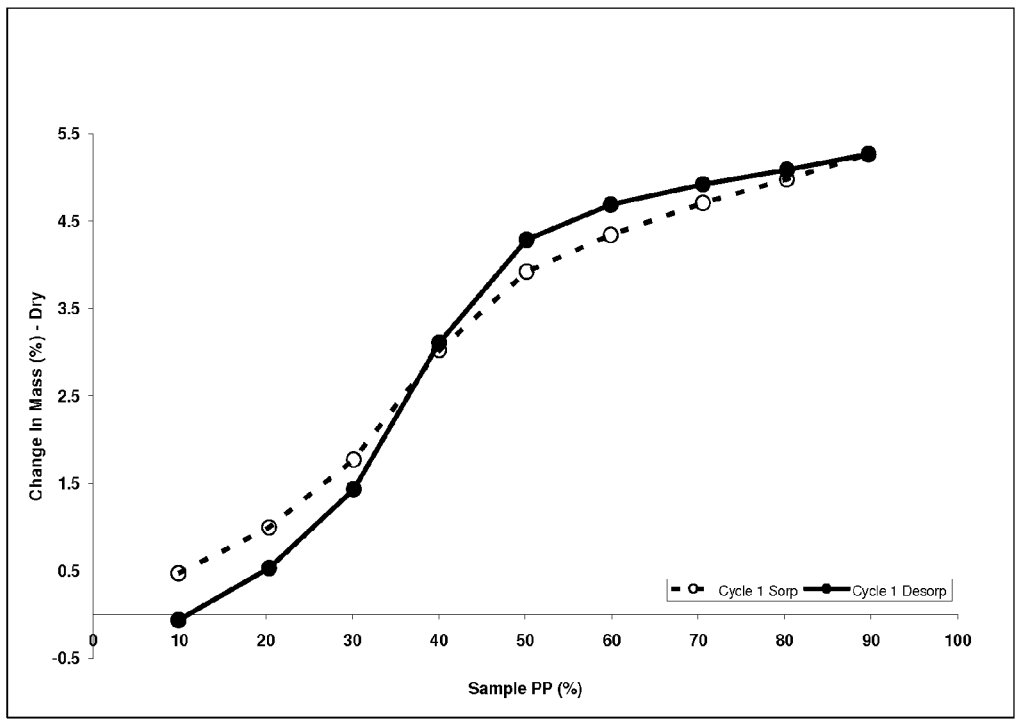
FIG. 18 shows a moisture sorption/desorption isotherm of the crystal obtained in Example 2 (crystal B). The longitudinal axis of the figure shows a change (%) in the mass of the compound, and the horizontal axis shows relative humidity (% RH). The broken line with open circles shows a moisture sorption curve, and the solid line with filled circles shows a moisture desorption curve.
Figure 27:
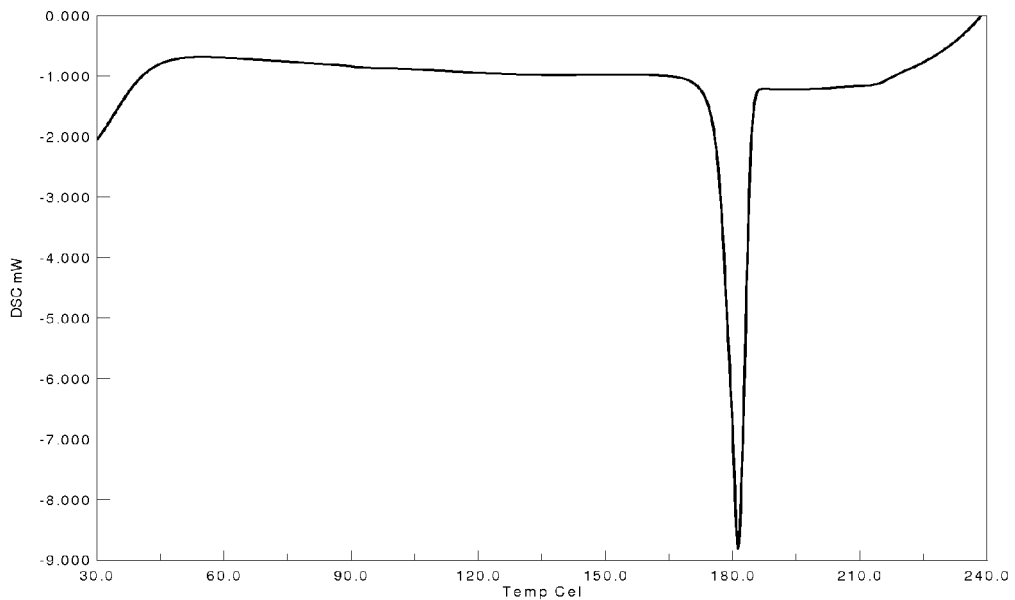
FIG. 27 shows a DSC curve of the crystal obtained in Example 2 (crystal B). The longitudinal axis of the figure shows heat flow (mW), and the horizontal axis shows temperature (° C.).
Figure 36:
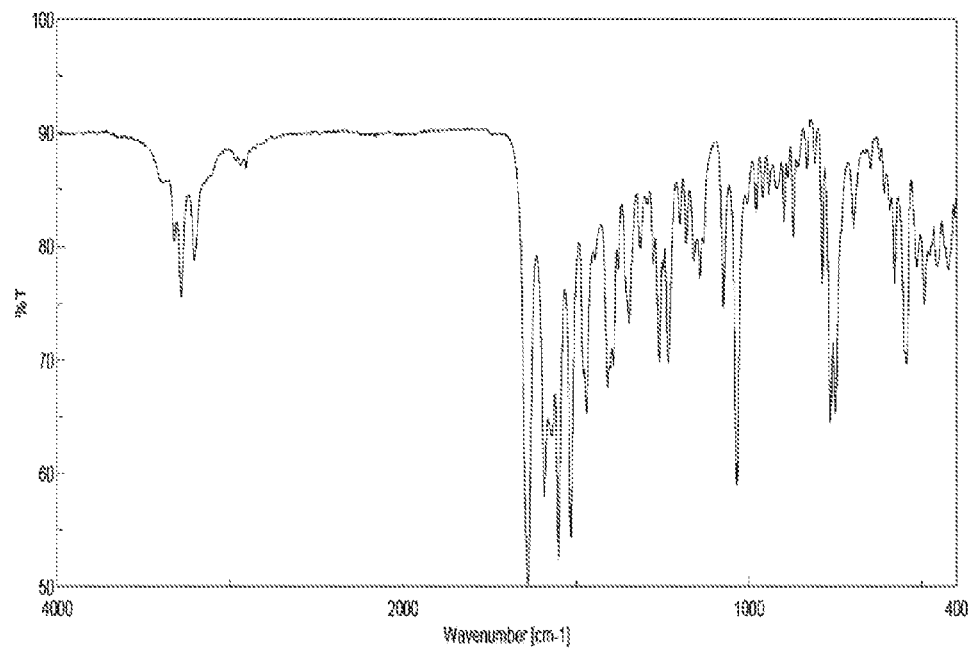
FIG. 36 shows an infrared absorption spectrum of the crystal obtained in Example 2 (crystal B). The longitudinal axis of the figure shows transmittance (% T), and the horizontal axis shows the wave number (cm$^{-1}$) of the infrared radiation applied.

A moisture sorption/desorption isotherm obtained by automatic measurement of the amount of water vapor adsorbed onto the obtained crystal is shown in FIG. 18, a DSC curve obtained by differential scanning calorimetry is shown in FIG. 27, and an infrared absorption spectrum thereof is shown in FIG. 36.

TABLE 3

| Peak No. | 2θ | d value | Relative intensity |
| --- | --- | --- | --- |
| 1 | 5.04 | 17.52 | 5 |
| 2 | 6.78 | 13.03 | 25 |
| 3 | 7.72 | 11.44 | 4 |
| 4 | 10.14 | 8.72 | 100 |
| 5 | 11.16 | 7.92 | 9 |
| 6 | 13.24 | 6.68 | 4 |
| 7 | 13.66 | 6.48 | 4 |
| 8 | 15.32 | 5.78 | 16 |
| 9 | 18.50 | 4.79 | 3 |
| 10 | 20.40 | 4.35 | 3 |
| 11 | 22.36 | 3.97 | 16 |
| 12 | 22.90 | 3.88 | 3 |
| 13 | 25.16 | 3.54 | 4 |
| 14 | 26.66 | 3.34 | 4 |
| 15 | 27.92 | 3.19 | 4 |
| 16 | 30.92 | 2.89 | 4 |
| 17 | 31.78 | 2.81 | 4 |

FIG. 3, and peaks with a relative intensity of 5 or greater, when the maximum peak intensity is set at 100 in FIG. 3, are shown in Table 4.

Figure 19:
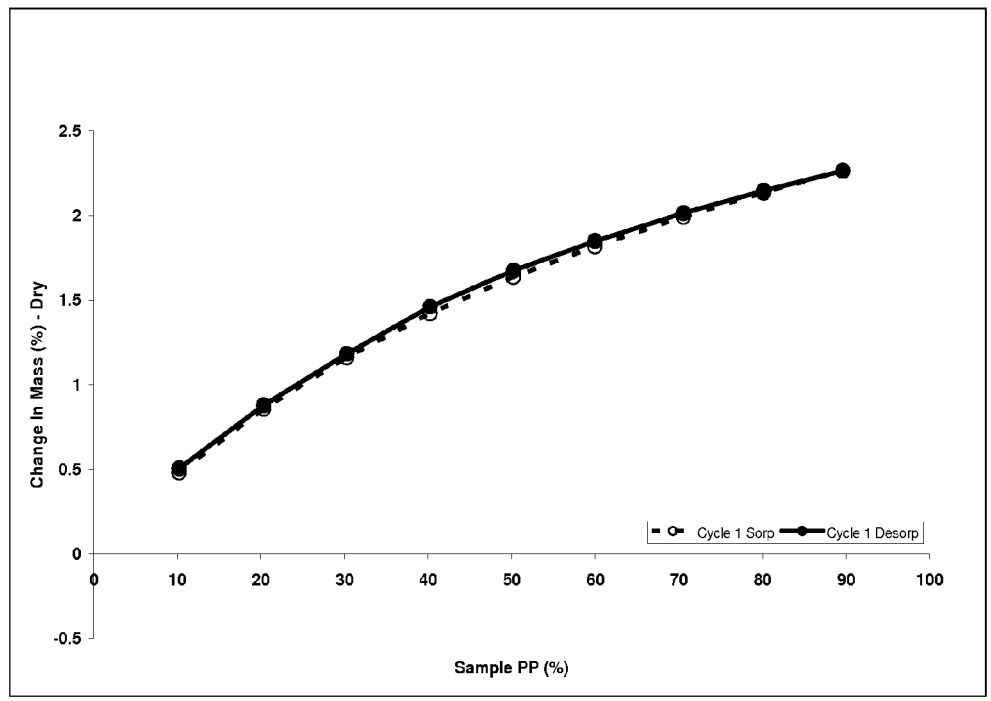
FIG. 19 shows a moisture sorption/desorption isotherm of the crystal obtained in Example 3 (crystal C). The longitudinal axis of the figure shows a change (%) in the mass of the compound, and the horizontal axis shows relative humidity (% RH). The broken line with open circles shows a moisture sorption curve, and the solid line with filled circles shows a moisture desorption curve.
Figure 28:
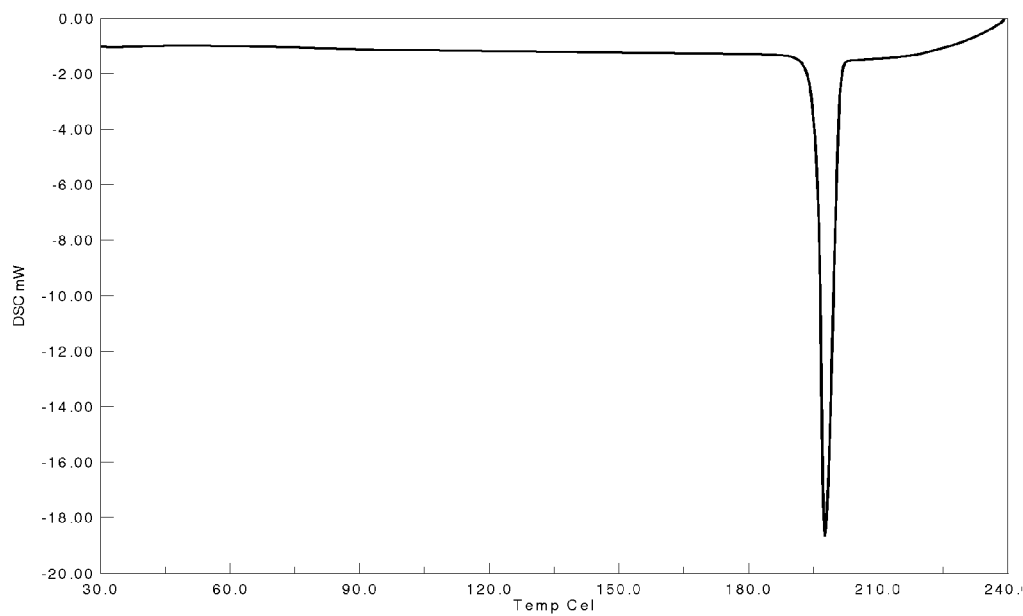
FIG. 28 shows a DSC curve of the crystal obtained in Example 3 (crystal C). The longitudinal axis of the figure shows heat flow (mW), and the horizontal axis shows temperature (° C.).
Figure 37:
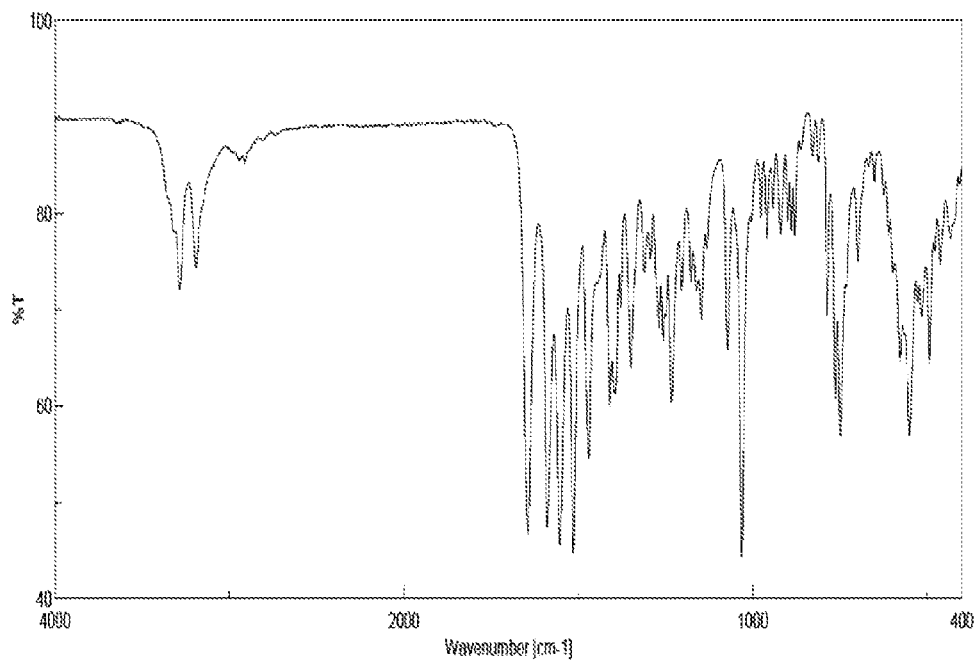
FIG. 37 shows an infrared absorption spectrum of the crystal obtained in Example 3 (crystal C). The longitudinal axis of the figure shows transmittance (% T), and the horizontal axis shows the wave number (cm$^{-1}$) of the infrared radiation applied.

A moisture sorption/desorption isotherm obtained by automatic measurement of the amount of water vapor adsorbed onto the obtained crystal is shown in FIG. 19, a DSC curve obtained by differential scanning calorimetry is shown in FIG. 28, and an infrared absorption spectrum thereof is shown in FIG. 37.

TABLE 4

| Peak No. | 2θ | d value | Relative intensity |
| --- | --- | --- | --- |
| 1 | 6.36 | 13.89 | 16 |
| 2 | 6.80 | 12.99 | 100 |
| 3 | 10.78 | 8.20 | 34 |
| 4 | 11.30 | 7.82 | 11 |
| 5 | 11.56 | 7.65 | 5 |
| 6 | 12.76 | 6.93 | 12 |
| 7 | 13.66 | 6.48 | 13 |
| 8 | 14.68 | 6.03 | 35 |
| 9 | 16.58 | 5.34 | 15 |
| 10 | 17.44 | 5.08 | 16 |
| 11 | 17.96 | 4.93 | 7 |
| 12 | 20.58 | 4.31 | 11 |
| 13 | 21.30 | 4.17 | 8 |
| 14 | 23.70 | 3.75 | 13 |
| 15 | 26.34 | 3.38 | 11 |
| 16 | 27.58 | 3.23 | 7 |
| 17 | 28.12 | 3.17 | 7 |
| 18 | 29.14 | 3.06 | 5 |
| 19 | 34.68 | 2.58 | 6 |

Example 3

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide crystal C Acetonitrile (300 mL) was added to 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (crystal A obtained by the same operations as those in the method described in the above Example 1) (308 mg, 0.691 mmol), and the aforementioned compound was dissolved therein by heating. Acetonitrile (150 mL) was removed from the resulting mixture under reflux under ordinary pressure, and water (150 ml) was then added to the mixture. Then, a mixed solution (150 ml) of acetonitrile and water was removed from the resulting mixture under reflux under ordinary pressure again. This operation of adding water (150 ml) was repeated four times, and the reaction mixture was then stirred at ordinary temperature for 4 days. Thereafter, a crystal was collected by filtration. The obtained crystal was dried under reduced pressure at room temperature for 2 days, so as to obtain the above title compound as crystal C (301 mg, 0.675 mmol). Yield: 98%.

The elemental analysis measurement values (theoretical values) of the obtained crystal are shown below.

For 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide, C, 50.00%; (51.18%), H, 4.50%; (4.52%), O, 8.97%; (7.18%), N, 21.54% (21.99%), Cl, 7.82%; (7.95%), and S, 7.10%; (7.19%).

A diffraction pattern from the X-ray powder diffraction (CuKα, λ=1.54 angstroms) of the obtained crystal is shown in Example 4

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide crystal D 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (crystal A obtained by the same operations as those in the method described in the above Example 1) (502 mg, 1.126 mmol) was dissolved in acetonitrile (500 mL) by heating, and the resulting solution was then filtered. Acetonitrile was removed from the filtrate under reflux under ordinary pressure, until a crystal was precipitated, and the resultant was then stirred at room temperature for 3 days. Thereafter, a crystal was collected by filtration. The obtained crystal was dried under reduced pressure at room temperature for 1 day, so as to obtain the above title compound as crystal D (469 mg, 1.052 mmol). Yield: 93%.

The elemental analysis measurement values (theoretical values) of the obtained crystal are shown below.

For 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide, C, 49.60%; (51.18%), H, 4.54%; (4.52%), O, 9.47%; (7.18%), N, 21.48%; (21.99%), Cl, 7.66%; (7.95%), and S, 6.91%; (7.19%).

A diffraction pattern from the X-ray powder diffraction (CuKα, λ=1.54 angstroms) of the obtained crystal is shown in FIG. 4, and peaks with a relative intensity of 3 or greater, when the maximum peak intensity is set at 100 in FIG. 4, are shown in Table 5.

Figure 20:
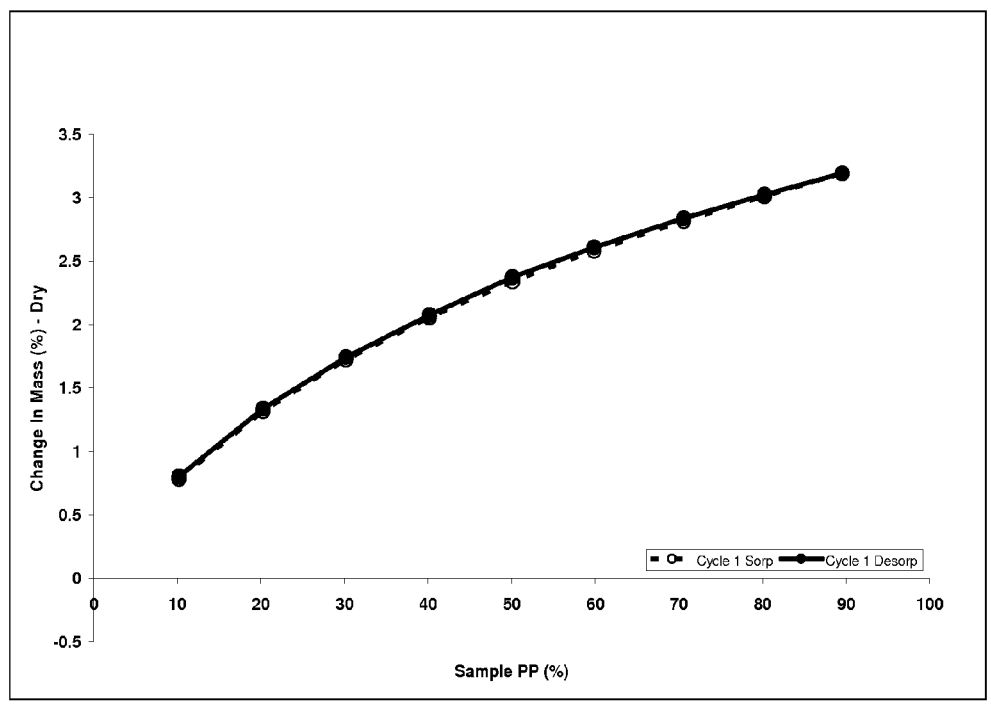
FIG. 20 shows a moisture sorption/desorption isotherm of the crystal obtained in Example 4 (crystal D). The longitudinal axis of the figure shows a change (%) in the mass of the compound, and the horizontal axis shows relative humidity (% RH). The broken line with open circles shows a moisture sorption curve, and the solid line with filled circles shows a moisture desorption curve.
Figure 29:
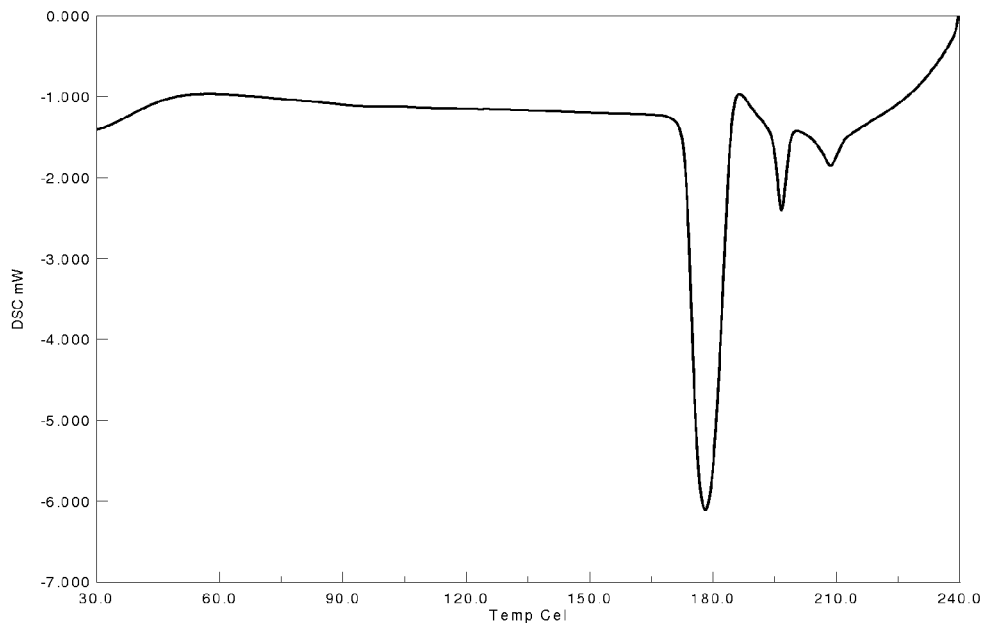
FIG. 29 shows a DSC curve of the crystal obtained in Example 4 (crystal D). The longitudinal axis of the figure shows heat flow (mW), and the horizontal axis shows temperature (° C.).
Figure 38:
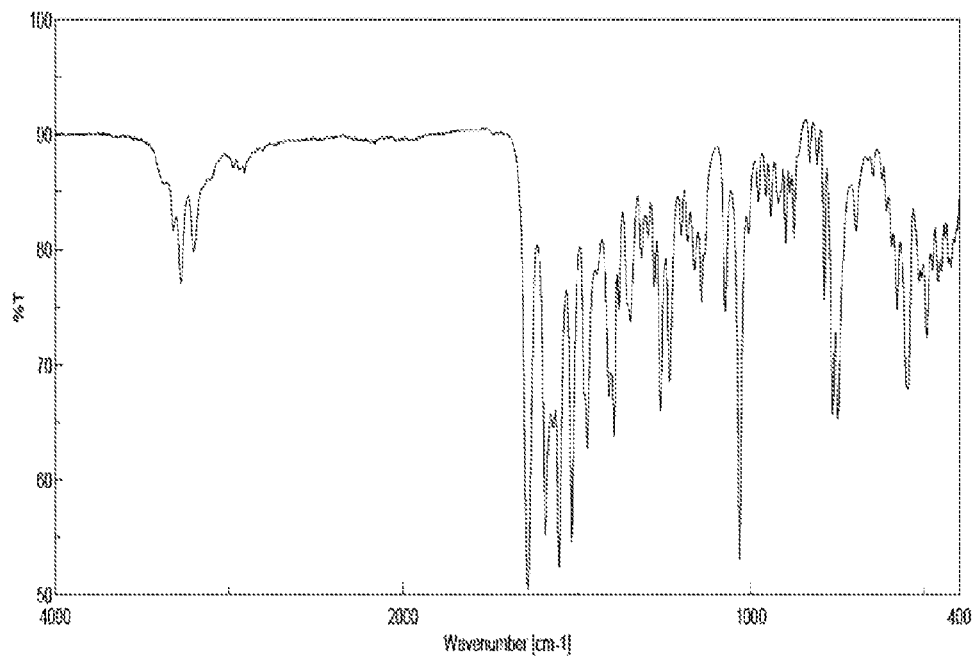
FIG. 38 shows an infrared absorption spectrum of the crystal obtained in Example 4 (crystal D). The longitudinal axis of the figure shows transmittance (% T), and the horizontal axis shows the wave number (cm$^{-1}$) of the infrared radiation applied.

A moisture sorption/desorption isotherm obtained by automatic measurement of the amount of water vapor adsorbed onto the obtained crystal is shown in FIG. 20, a DSC curve obtained by differential scanning calorimetry is shown in FIG. 29, and an infrared absorption spectrum thereof is shown in FIG. 38.

TABLE 5

| Peak No. | 2θ | d value | Relative intensity |
|---|---|---|---|
| 1 | 6.08 | 14.52 | 5 |
| 2 | 6.72 | 13.14 | 100 |
| 3 | 8.42 | 10.49 | 3 |
| 4 | 10.16 | 8.70 | 15 |
| 5 | 10.72 | 8.25 | 7 |
| 6 | 11.32 | 7.81 | 3 |
| 7 | 12.22 | 7.24 | 4 |
| 8 | 13.50 | 6.55 | 8 |
| 9 | 14.44 | 6.13 | 35 |
| 10 | 15.68 | 5.65 | 5 |
| 11 | 16.96 | 5.22 | 7 |
| 12 | 17.68 | 5.01 | 6 |
| 13 | 20.36 | 4.36 | 7 |
| 14 | 22.92 | 3.88 | 6 |
| 15 | 25.58 | 3.48 | 7 |
| 16 | 27.26 | 3.27 | 4 |
| 17 | 27.76 | 3.21 | 8 |
| 18 | 34.30 | 2.61 | 3 |
| 19 | 35.88 | 2.50 | 3 |

Example 5

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide crystal E 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride (which had been obtained by the same operations as those in the method described in the above Reference Example 2) (208 mg, 0.431 mmol) was suspended in the second dissolution test medium (100 ml) of the Japanese Pharmacopoeia, and the resulting mixture was then stirred at 40° C. overnight. Thereafter, a precipitate was collected by filtration, and was then dried under reduced pressure at room temperature overnight, so as to obtain the above title compound as crystal E (160 mg, 0.359 mmol). Yield: 83%.

The elemental analysis measurement values (theoretical values) of the obtained crystal are shown below. For 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide, C, 50.14%; (51.18%), H, 4.49%; (4.52%), O, 8.68%; (7.18%), N, 21.42%; (21.99%), Cl, 8.07%; (7.95%), and S, 7.07%; (7.19%).

A diffraction pattern from the X-ray powder diffraction (CuKα, λ=1.54 angstroms) of the obtained crystal is shown in FIG. 5, and peaks with a relative intensity of 5 or greater, when the maximum peak intensity is set at 100 in FIG. 5, are shown in Table 6.

TABLE 6

| Peak No. | 2θ | d value | Relative intensity |
|---|---|---|---|
| 1 | 6.24 | 14.15 | 20 |
| 2 | 6.84 | 12.91 | 100 |
| 3 | 8.30 | 10.64 | 16 |
| 4 | 11.80 | 7.49 | 7 |
| 5 | 12.58 | 7.03 | 10 |
| 6 | 13.74 | 6.44 | 11 |
| 7 | 14.62 | 6.05 | 35 |
| 8 | 19.36 | 4.58 | 14 |
| 9 | 19.94 | 4.45 | 6 |
| 10 | 20.74 | 4.28 | 32 |
| 11 | 23.86 | 3.73 | 30 |
| 12 | 24.26 | 3.67 | 11 |
| 13 | 25.38 | 3.51 | 5 |
| 14 | 26.00 | 3.42 | 9 |
| 15 | 27.40 | 3.25 | 12 |
| 16 | 27.78 | 3.21 | 7 |
| 17 | 29.38 | 3.04 | 8 |
| 18 | 29.54 | 3.02 | 7 |
| 19 | 30.66 | 2.91 | 8 |

Example 6

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide crystal F 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (crystal A obtained by the same operations as those in the method described in the above Example 1) (200 mg, 0.449 mmol) was dissolved in 2-propanol (180 mL) by heating, and thereafter, 2-propanol (171 mL) was removed from the resulting mixture under reflux under ordinary pressure. The resultant was stirred at room temperature for 3 days, and a precipitate was then collected by filtration. To this precipitate, 2-propanol (1.5 mL) was added, and the resulting mixture was then stirred at 40° C. for 2 days. Thereafter, a precipitate was collected by filtration, so as to obtain the above title compound as crystal F (140 mg, 0.314 mmol). Yield: 70%.

The elemental analysis measurement values (theoretical values) of the obtained crystal are shown below. For 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide, C, 49.95%; (51.18%), H, 4.71%; (4.52%), O, 7.74%; (7.18%), N, 20.99%; (21.99%), Cl, 7.69%; (7.95%), and S, 6.85%; (7.19%).

A diffraction pattern from the X-ray powder diffraction (CuKα, λ=1.54 angstroms) of the obtained crystal is shown in FIG. 6, and peaks with a relative intensity of 12 or greater, when the maximum peak intensity is set at 100 in FIG. 6, are shown in Table 7.

Figure 21:
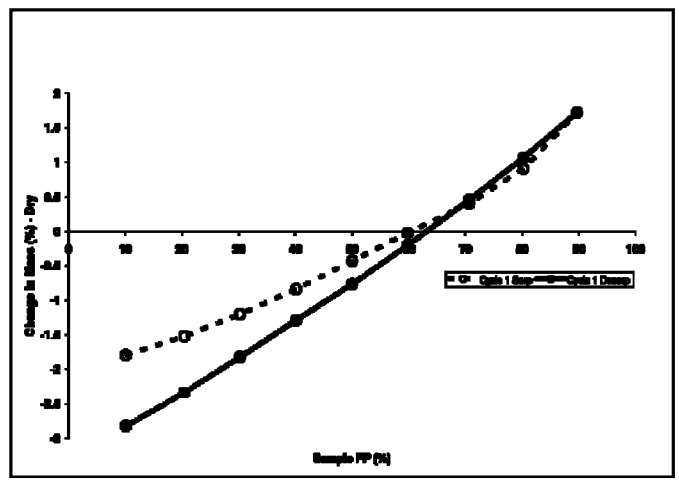
FIG. 21 shows a moisture sorption/desorption isotherm of the crystal obtained in Example 6 (crystal F). The longitudinal axis of the figure shows a change (%) in the mass of the compound, and the horizontal axis shows relative humidity (% RH). The broken line with open circles shows a moisture sorption curve, and the solid line with filled circles shows a moisture desorption curve.
Figure 30:
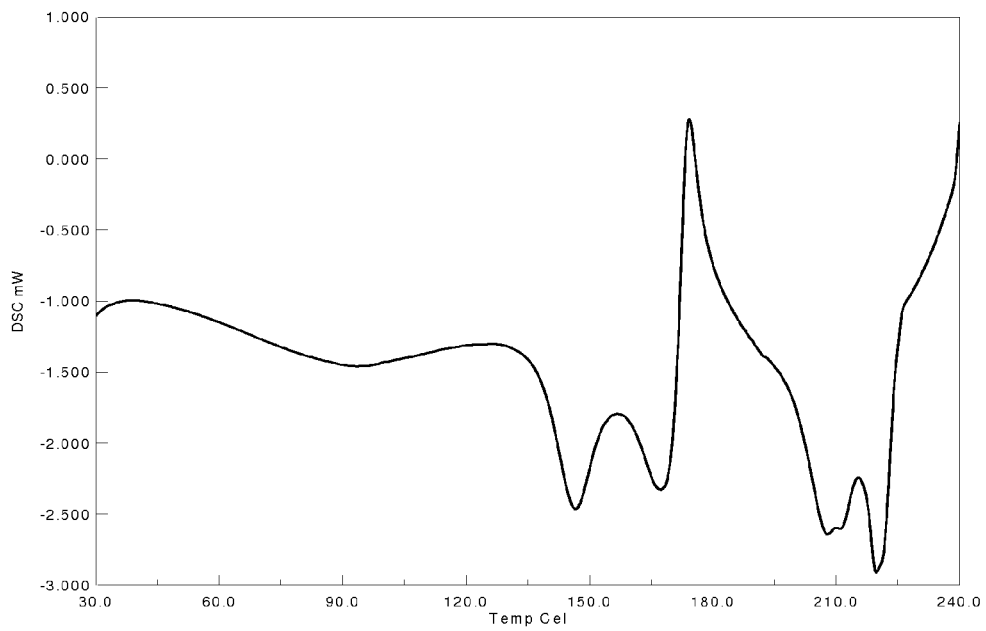
FIG. 30 shows a DSC curve of the crystal obtained in Example 6 (crystal F). The longitudinal axis of the figure shows heat flow (mW), and the horizontal axis shows temperature (° C.).
Figure 39:
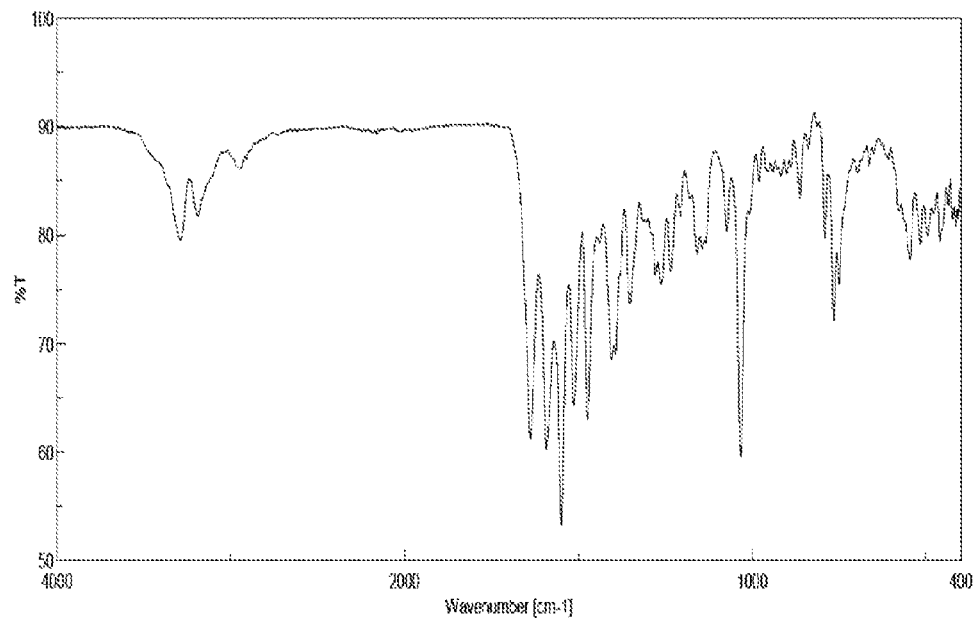
FIG. 39 shows an infrared absorption spectrum of the crystal obtained in Example 6 (crystal F). The longitudinal axis of the figure shows transmittance (% T), and the horizontal axis shows the wave number (cm$^{-1}$) of the infrared radiation applied.

A moisture sorption/desorption isotherm obtained by automatic measurement of the amount of water vapor adsorbed onto the obtained crystal is shown in FIG. 21, a DSC curve obtained by differential scanning calorimetry is shown in FIG. 30, and an infrared absorption spectrum thereof is shown in FIG. 39.

TABLE 7

| Peak No. | 2θ | d value | Relative intensity |
|---|---|---|---|
| 1 | 3.26 | 27.08 | 76 |
| 2 | 4.64 | 19.03 | 100 |
| 3 | 5.30 | 16.66 | 58 |
| 4 | 6.06 | 14.57 | 98 |
| 5 | 6.54 | 13.50 | 29 |
| 6 | 9.82 | 9.00 | 27 |
| 7 | 11.48 | 7.70 | 18 |

TABLE 7-continued

| Peak No. | 2θ | d value | Relative intensity |
|---|---|---|---|
| 8 | 13.14 | 6.73 | 12 |
| 9 | 13.98 | 6.33 | 72 |
| 10 | 14.54 | 6.09 | 78 |
| 11 | 15.04 | 5.89 | 19 |
| 12 | 18.30 | 4.84 | 13 |
| 13 | 20.62 | 4.30 | 15 |
| 14 | 22.46 | 3.96 | 28 |
| 15 | 23.24 | 3.82 | 13 |
| 16 | 23.60 | 3.77 | 15 |
| 17 | 24.48 | 3.63 | 13 |
| 18 | 25.34 | 3.51 | 15 |
| 19 | 26.82 | 3.32 | 14 |
| 20 | 28.12 | 3.17 | 13 |

Example 7

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide crystal G 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (crystal A obtained by the same operations as those in the method described in the above Example 1) (200 mg, 0.449 mmol) was dissolved in 2-methyl-1-propanol (40 mL) by heating, and thereafter, 2-methyl-1-propanol (32 mL) was removed from the resulting mixture under reflux under ordinary pressure. The resultant was stirred at room temperature for 5 days, and a precipitate was then collected by filtration, so as to obtain the above title compound as crystal G (190 mg, 0.426 mmol). Yield: 95%.

The elemental analysis measurement values (theoretical values) of the obtained crystal are shown below. For 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide, C, 50.65%; (51.18%), H, 4.82%; (4.52%), O, 7.74%; (7.18%), N, 20.97%; (21.99%), Cl, 7.71%; (7.95%), and S, 6.87%; (7.19%).

A diffraction pattern from the X-ray powder diffraction (CuKα, λ=1.54 angstroms) of the obtained crystal is shown in FIG. 7, and peaks with a relative intensity of 5 or greater, when the maximum peak intensity is set at 100 in FIG. 7, are shown in Table 8.

Figure 22:
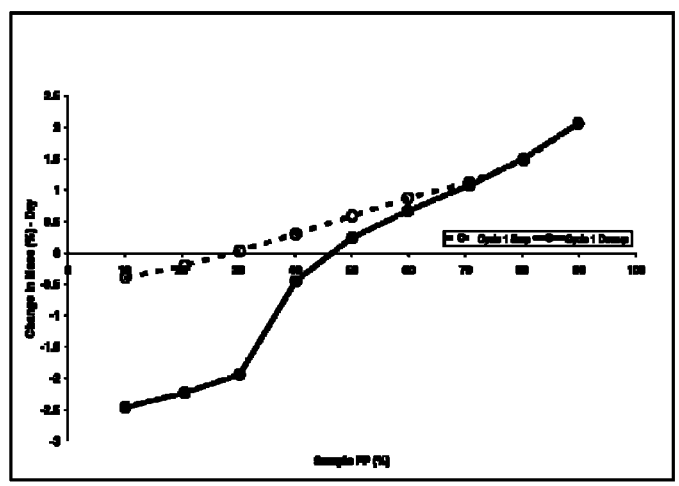
FIG. 22 shows a moisture sorption/desorption isotherm of the crystal obtained in Example 7 (crystal G). The longitudinal axis of the figure shows a change (%) in the mass of the compound, and the horizontal axis shows relative humidity (% RH). The broken line with open circles shows a moisture sorption curve, and the solid line with filled circles shows a moisture desorption curve.
Figure 31:
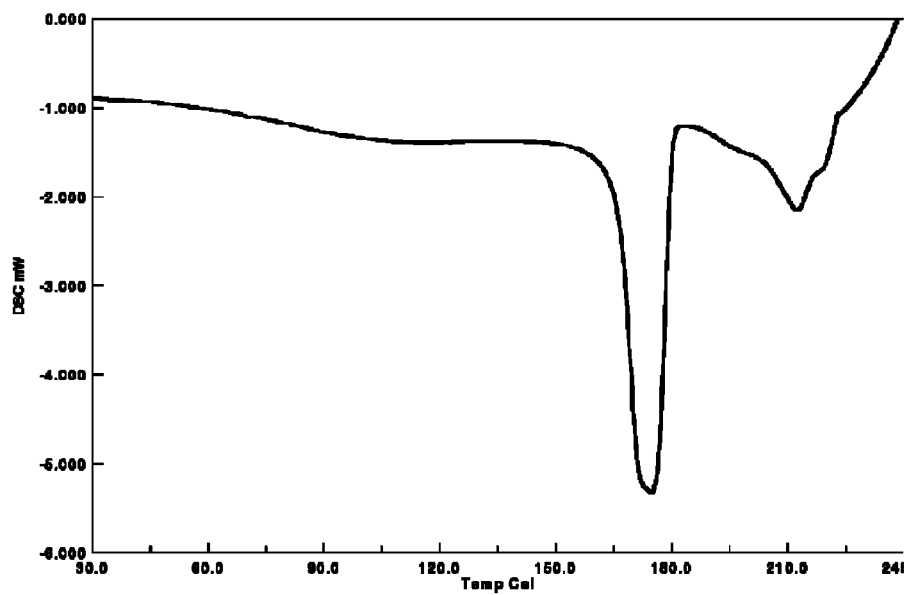
FIG. 31 shows a DSC curve of the crystal obtained in Example 7 (crystal G). The longitudinal axis of the figure shows heat flow (mW), and the horizontal axis shows temperature (° C.).
Figure 40:
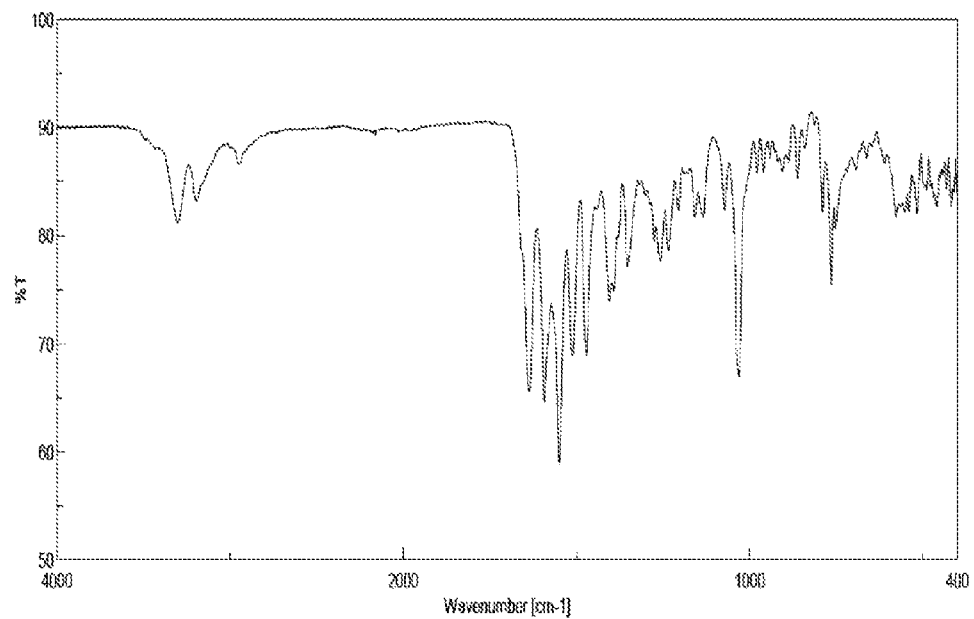
FIG. 40 shows an infrared absorption spectrum of the crystal obtained in Example 7 (crystal G). The longitudinal axis of the figure shows transmittance (% T), and the horizontal axis shows the wave number (cm$^{-1}$) of the infrared radiation applied.

A moisture sorption/desorption isotherm obtained by automatic measurement of the amount of water vapor adsorbed onto the obtained crystal is shown in FIG. 22, a DSC curve obtained by differential scanning calorimetry is shown in FIG. 31, and an infrared absorption spectrum thereof is shown in FIG. 40.

TABLE 8

| Peak No. | 2θ | d value | Relative intensity |
|---|---|---|---|
| 1 | 4.72 | 18.71 | 26 |
| 2 | 5.52 | 16.00 | 100 |
| 3 | 6.18 | 14.29 | 5 |
| 4 | 9.46 | 9.34 | 11 |
| 5 | 10.44 | 8.47 | 14 |
| 6 | 12.38 | 7.14 | 11 |
| 7 | 14.22 | 6.22 | 71 |
| 8 | 15.22 | 5.82 | 8 |
| 9 | 15.90 | 5.57 | 14 |
| 10 | 19.48 | 4.55 | 8 |
| 11 | 19.74 | 4.49 | 5 |

TABLE 8-continued

| Peak No. | 2θ | d value | Relative intensity |
|---|---|---|---|
| 12 | 20.62 | 4.30 | 22 |
| 13 | 21.00 | 4.23 | 6 |
| 14 | 22.00 | 4.04 | 5 |
| 15 | 22.28 | 3.99 | 9 |
| 16 | 25.24 | 3.53 | 6 |
| 17 | 26.22 | 3.40 | 7 |
| 18 | 27.34 | 3.26 | 5 |

Example 8

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide crystal H 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (an amorphous solid obtained by the same operations as those in the method described in the above Reference Example 1) (15 mg) was dissolved in N,N-dimethylacetamide (50 μL) at room temperature, and a precipitate was then collected by filtration, so as to obtain the above title compound as crystal H.

A diffraction pattern from the X-ray powder diffraction (CuKα, λ=1.54 angstroms) of the obtained crystal is shown in FIG. 8, and peaks with a relative intensity of 8 or greater, when the maximum peak intensity is set at 100 in FIG. 8, are shown in Table 9.

TABLE 9

| Peak No. | 2θ | d value | Relative intensity |
|---|---|---|---|
| 1 | 7.92 | 11.15 | 61 |
| 2 | 10.10 | 8.75 | 37 |
| 3 | 12.50 | 7.08 | 25 |
| 4 | 13.94 | 6.35 | 100 |
| 5 | 14.84 | 5.96 | 54 |
| 6 | 15.36 | 5.76 | 8 |
| 7 | 15.50 | 5.71 | 8 |
| 8 | 17.70 | 5.01 | 15 |
| 9 | 18.56 | 4.78 | 19 |
| 10 | 18.84 | 4.71 | 26 |
| 11 | 21.26 | 4.18 | 13 |
| 12 | 22.02 | 4.03 | 22 |
| 13 | 22.70 | 3.91 | 9 |
| 14 | 23.56 | 3.77 | 49 |
| 15 | 23.88 | 3.72 | 18 |
| 16 | 24.80 | 3.59 | 39 |
| 17 | 25.40 | 3.50 | 37 |
| 18 | 28.14 | 3.17 | 17 |
| 19 | 28.58 | 3.12 | 10 |

Example 9

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide crystal I Nitromethane (200 μL) was added to 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (an amorphous solid obtained by the same operations as those in the method described in the above Reference Example 1) (5 mg) at room temperature. The resulting slurry was stirred for 4 days, while repeating an operation of increasing and decreasing the temperature from 5° C. to 60° C. six times. Thereafter, a precipitate was collected by filtration, so as to obtain the above title compound as crystal I.

A diffraction pattern from the X-ray powder diffraction (CuKα, λ=1.54 angstroms) of the obtained crystal is shown in FIG. 9, and peaks with a relative intensity of 17 or greater, when the maximum peak intensity is set at 100 in FIG. 9, are shown in Table 10.

TABLE 10

| Peak No. | 2θ | d value | Relative intensity |
| --- | --- | --- | --- |
| 1 | 5.00 | 17.66 | 47 |
| 2 | 6.70 | 13.18 | 100 |
| 3 | 7.70 | 11.47 | 35 |
| 4 | 10.08 | 8.77 | 73 |
| 5 | 10.72 | 8.25 | 24 |
| 6 | 14.42 | 6.14 | 34 |
| 7 | 15.60 | 5.68 | 21 |
| 8 | 18.96 | 4.68 | 19 |
| 9 | 20.44 | 4.34 | 27 |
| 10 | 22.34 | 3.98 | 50 |
| 11 | 23.16 | 3.84 | 41 |
| 12 | 23.30 | 3.82 | 32 |
| 13 | 25.10 | 3.54 | 20 |
| 14 | 25.48 | 3.49 | 17 |
| 15 | 28.12 | 3.17 | 21 |

Example 10

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide crystal J t-Butyl methyl ether (1000 μL) was added to 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (an amorphous solid obtained by the same operations as those in the method described in the above Reference Example 1) (5 mg) at room temperature. The resulting slurry was stirred for 4 days, while repeating an operation of increasing and decreasing the temperature from 5° C. to 60° C. six times. Thereafter, a precipitate was collected by filtration, so as to obtain the above title compound as crystal J.

A diffraction pattern from the X-ray powder diffraction (CuKα, λ=1.54 angstroms) of the obtained crystal is shown in FIG. 10, and peaks with a relative intensity of 7 or greater, when the maximum peak intensity is set at 100 in FIG. 10, are shown in Table 11.

TABLE 11

| Peak No. | 2θ | d value | Relative intensity |
| --- | --- | --- | --- |
| 1 | 4.70 | 18.79 | 23 |
| 2 | 5.50 | 16.05 | 100 |
| 3 | 9.38 | 9.42 | 12 |
| 4 | 10.40 | 8.50 | 17 |
| 5 | 12.36 | 7.16 | 12 |
| 6 | 14.18 | 6.24 | 51 |
| 7 | 15.22 | 5.82 | 11 |
| 8 | 15.92 | 5.56 | 12 |
| 9 | 19.78 | 4.48 | 12 |
| 10 | 20.60 | 4.31 | 10 |
| 11 | 21.00 | 4.23 | 9 |
| 12 | 24.30 | 3.66 | 9 |

TABLE 11-continued

| Peak No. | 2θ | d value | Relative intensity |
| --- | --- | --- | --- |
| 13 | 25.56 | 3.48 | 13 |
| 14 | 26.24 | 3.39 | 8 |
| 15 | 26.80 | 3.32 | 7 |
| 16 | 27.30 | 3.26 | 8 |

Example 11

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide crystal K Dimethyl sulfoxide (50 μL) was added to 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (an amorphous solid obtained by the same operations as those in the method described in the above Reference Example 1) (15 mg) at room temperature. The resulting slurry was stirred for 4 days, while repeating an operation of increasing and decreasing the temperature from 5° C. to 60° C. six times. Thereafter, a precipitate was collected by filtration, so as to obtain the above title compound as crystal K.

A diffraction pattern from the X-ray powder diffraction (CuKα, λ=1.54 angstroms) of the obtained crystal is shown in FIG. 11, and peaks with a relative intensity of 21 or greater, when the maximum peak intensity is set at 100 in FIG. 11, are shown in Table 12.

TABLE 12

| Peak No. | 2θ | d value | Relative intensity |
| --- | --- | --- | --- |
| 1 | 6.88 | 12.84 | 22 |
| 2 | 10.04 | 8.80 | 57 |
| 3 | 13.84 | 6.39 | 27 |
| 4 | 15.40 | 5.75 | 65 |
| 5 | 15.58 | 5.68 | 80 |
| 6 | 18.50 | 4.79 | 46 |
| 7 | 19.60 | 4.53 | 24 |
| 8 | 20.16 | 4.40 | 21 |
| 9 | 20.80 | 4.27 | 38 |
| 10 | 21.58 | 4.11 | 23 |
| 11 | 21.94 | 4.05 | 23 |
| 12 | 22.36 | 3.97 | 100 |
| 13 | 22.68 | 3.92 | 49 |
| 14 | 23.22 | 3.83 | 22 |
| 15 | 23.42 | 3.80 | 38 |
| 16 | 24.84 | 3.58 | 33 |
| 17 | 25.34 | 3.51 | 31 |
| 18 | 26.20 | 3.40 | 23 |
| 19 | 27.16 | 3.28 | 27 |
| 20 | 27.42 | 3.25 | 23 |
| 21 | 28.04 | 3.18 | 48 |
| 22 | 31.80 | 2.81 | 24 |

Example 12

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide crystal L Diethyl ether (200 μL) was added to 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (an amorphous solid obtained by the same operations as those in the method described in the above Reference Example 1) (5 mg) at room temperature. The resulting slurry was stirred for 4 days, while repeating an operation of increasing and decreasing the temperature from 5° C. to 60° C. six times. Thereafter, a precipitate was collected by filtration, so as to obtain the above title compound as crystal L.

A diffraction pattern from the X-ray powder diffraction (CuKα, λ=1.54 angstroms) of the obtained crystal is shown in FIG. 12, and peaks with a relative intensity of 38 or greater, when the maximum peak intensity is set at 100 in FIG. 12, are shown in Table 13.

TABLE 13

| Peak No. | 2θ | d value | Relative intensity |
|---|---|---|---|
| 1 | 7.46 | 11.84 | 100 |
| 2 | 10.18 | 8.68 | 84 |
| 3 | 12.68 | 6.98 | 70 |
| 4 | 14.30 | 6.19 | 42 |
| 5 | 14.96 | 5.92 | 93 |
| 6 | 15.10 | 5.86 | 82 |
| 7 | 16.34 | 5.42 | 57 |
| 8 | 20.26 | 4.38 | 45 |
| 9 | 21.94 | 4.05 | 42 |
| 10 | 22.52 | 3.94 | 38 |
| 11 | 22.70 | 3.91 | 53 |
| 12 | 24.28 | 3.66 | 56 |
| 13 | 24.48 | 3.63 | 43 |
| 14 | 24.78 | 3.59 | 45 |
| 15 | 25.48 | 3.49 | 53 |

Example 13

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide crystal M Isopropyl acetate (200 μL) was added to 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (an amorphous solid obtained by the same operations as those in the method described in the above Reference Example 1) (5 mg) at room temperature. The resulting slurry was stirred for 4 days, while repeating an operation of increasing and decreasing the temperature from 5° C. to 60° C. six times. Thereafter, a precipitate was collected by filtration, so as to obtain the above title compound as crystal M.

A diffraction pattern from the X-ray powder diffraction (CuKα, λ=1.54 angstroms) of the obtained crystal is shown in FIG. 13, and peaks with a relative intensity of 15 or greater, when the maximum peak intensity is set at 100 in FIG. 13, are shown in Table 14.

TABLE 14

| Peak No. | 2θ | d value | Relative intensity |
|---|---|---|---|
| 1 | 8.12 | 10.88 | 80 |
| 2 | 9.78 | 9.04 | 15 |
| 3 | 10.86 | 8.14 | 62 |
| 4 | 13.60 | 6.51 | 73 |
| 5 | 13.94 | 6.35 | 47 |
| 6 | 15.86 | 5.58 | 27 |
| 7 | 16.32 | 5.43 | 70 |
| 8 | 17.10 | 5.18 | 59 |
| 9 | 18.48 | 4.80 | 17 |

TABLE 14-continued

| Peak No. | 2θ | d value | Relative intensity |
|---|---|---|---|
| 10 | 19.54 | 5.34 | 41 |
| 11 | 20.04 | 4.43 | 24 |
| 12 | 20.36 | 4.36 | 27 |
| 13 | 20.62 | 4.30 | 18 |
| 14 | 23.10 | 3.85 | 100 |
| 15 | 24.26 | 3.67 | 27 |
| 16 | 24.60 | 3.62 | 52 |
| 17 | 24.96 | 3.56 | 18 |
| 18 | 25.32 | 3.51 | 30 |
| 19 | 25.64 | 3.47 | 100 |
| 20 | 26.76 | 3.33 | 25 |

Example 14

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide crystal N 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (crystal A obtained by the same operations as those in the method described in the above Example 1) (540 mg, 1.211 mmol) was suspended in 2-butanone (20 ml), and a solvent trap containing molecular sieves 4A in an upper portion thereof was then set therein. Then, the resulting mixture was heated to reflux under a nitrogen atmosphere for 14 hours. Thereafter, a precipitate was collected by filtration, and was washed with hot 2-butanone (10 ml) and then with acetone (5 ml). The resultant was dried under reduced pressure at 80° C. overnight, so as to obtain the above title compound as crystal N (225 mg, 0.505 mmol). Yield: 42%.

The elemental analysis measurement values (theoretical values) of the obtained crystal are shown below.

For 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide, C, 50.34%; (51.18%), H, 4.55%; (4.52%), O, 8.73%; (7.18%), N, 21.19%; (21.99%), Cl, 7.64%; (7.95%), and S, 6.96%; (7.19%).

A diffraction pattern from the X-ray powder diffraction (CuKα, λ=1.54 angstroms) of the obtained crystal is shown in FIG. 14, and peaks with a relative intensity of 8 or greater, when the maximum peak intensity is set at 100 in FIG. 14, are shown in Table 15.

Figure 23:
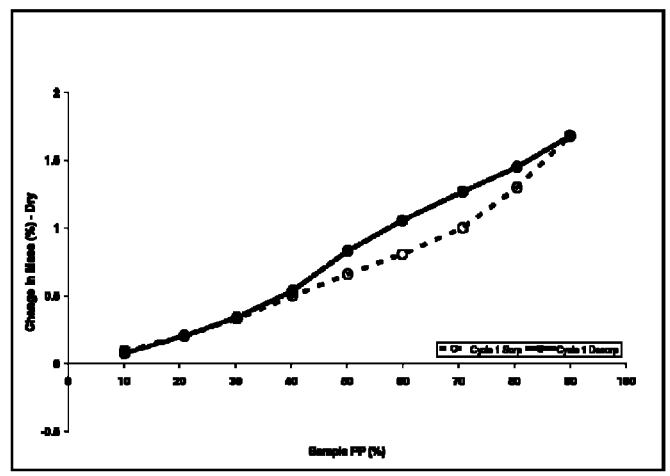
FIG. 23 shows a moisture sorption/desorption isotherm of the crystal obtained in Example 14 (crystal N). The longitudinal axis of the figure shows a change (%) in the mass of the compound, and the horizontal axis shows relative humidity (% RH). The broken line with open circles shows a moisture sorption curve, and the solid line with filled circles shows a moisture desorption curve.
Figure 32:
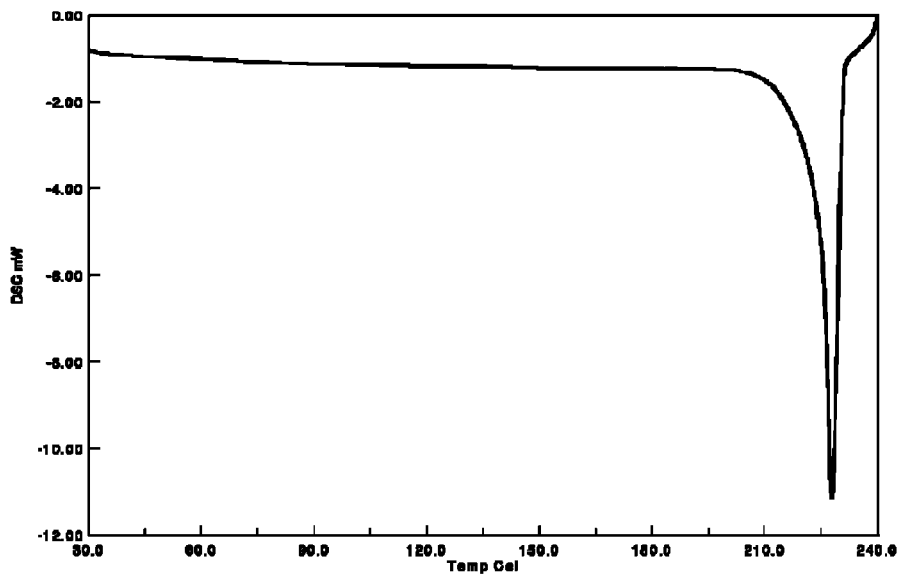
FIG. 32 shows a DSC curve of the crystal obtained in Example 14 (crystal N). The longitudinal axis of the figure shows heat flow (mW), and the horizontal axis shows temperature (° C.).
Figure 41:
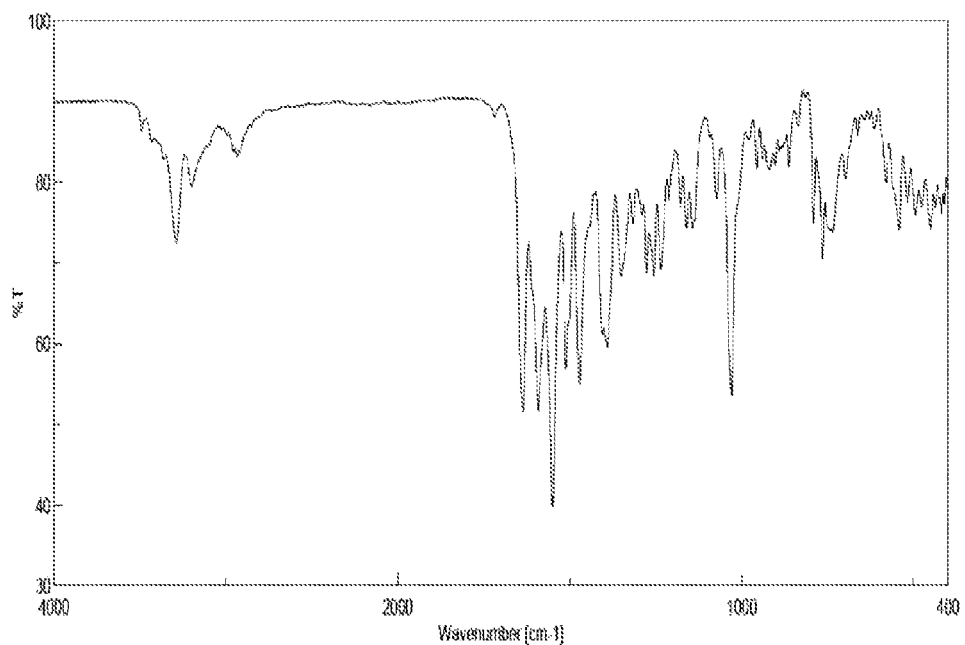
FIG. 41 shows an infrared absorption spectrum of the crystal obtained in Example 14 (crystal N). The longitudinal axis of the figure shows transmittance (% T), and the horizontal axis shows the wave number (cm$^{-1}$) of the infrared radiation applied.

A moisture sorption/desorption isotherm obtained by automatic measurement of the amount of water vapor adsorbed onto the obtained crystal is shown in FIG. 23, a DSC curve obtained by differential scanning calorimetry is shown in FIG. 32, and an infrared absorption spectrum thereof is shown in FIG. 41.

TABLE 15

| Peak No. | 2θ | d value | Relative intensity |
|---|---|---|---|
| 1 | 3.10 | 28.48 | 16 |
| 2 | 4.00 | 22.07 | 23 |
| 3 | 6.24 | 14.15 | 72 |
| 4 | 8.54 | 10.35 | 32 |
| 5 | 9.62 | 9.19 | 36 |
| 6 | 11.50 | 7.69 | 10 |
| 7 | 11.82 | 7.48 | 25 |
| 8 | 12.14 | 7.28 | 8 |
| 9 | 13.56 | 6.52 | 10 |

TABLE 15-continued

| Peak No. | 2θ | d value | Relative intensity |
|---|---|---|---|
| 10 | 14.44 | 6.13 | 100 |
| 11 | 14.98 | 5.91 | 13 |
| 12 | 15.22 | 5.82 | 10 |
| 13 | 17.18 | 5.16 | 10 |
| 14 | 17.60 | 5.04 | 11 |
| 15 | 17.82 | 4.97 | 16 |
| 16 | 20.72 | 4.28 | 9 |
| 17 | 22.12 | 4.02 | 26 |
| 18 | 24.18 | 3.68 | 10 |

Example 15

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide crystal O 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (crystal A obtained by the same operations as those in the method described in the above Example 1) (405 mg, 0.908 mmol) was dissolved in acetone (700 mL) by heating, and thereafter, acetone (481 mL) was removed from the resulting mixture under reflux under ordinary pressure. The resultant was left at rest at −20° C. for 1 day. Thereafter, a precipitate was collected by filtration, and was then dried under reduced pressure for 1 hour, so as to obtain the above title compound as crystal O (200 mg, 0.449 mmol). Yield: 49%.

The elemental analysis measurement values (theoretical values) of the obtained crystal are shown below.

For 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide, C, 50.65%; (51.18%), H, 4.49%; (4.52%), O, 8.87%; (7.18%), N, 21.86%; (21.99%), Cl, 7.88%; (7.95%), and S, 7.15%; (7.19%).

A diffraction pattern from the X-ray powder diffraction (CuKα, λ=1.54 angstroms) of the obtained crystal is shown in FIG. 15, and peaks with a relative intensity of 5 or greater, when the maximum peak intensity is set at 100 in FIG. 15, are shown in Table 16.

Figure 24:
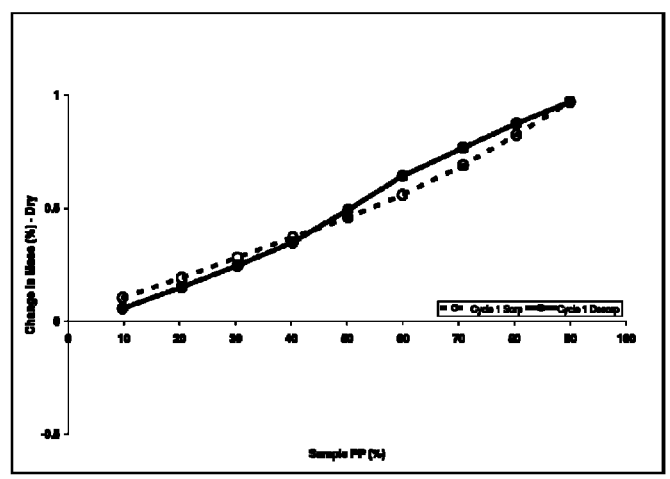
FIG. 24 shows a moisture sorption/desorption isotherm of the crystal obtained in Example 15 (crystal O). The longitudinal axis of the figure shows a change (%) in the mass of the compound, and the horizontal axis shows relative humidity (% RH). The broken line with open circles shows a moisture sorption curve, and the solid line with filled circles shows a moisture desorption curve.
Figure 33:
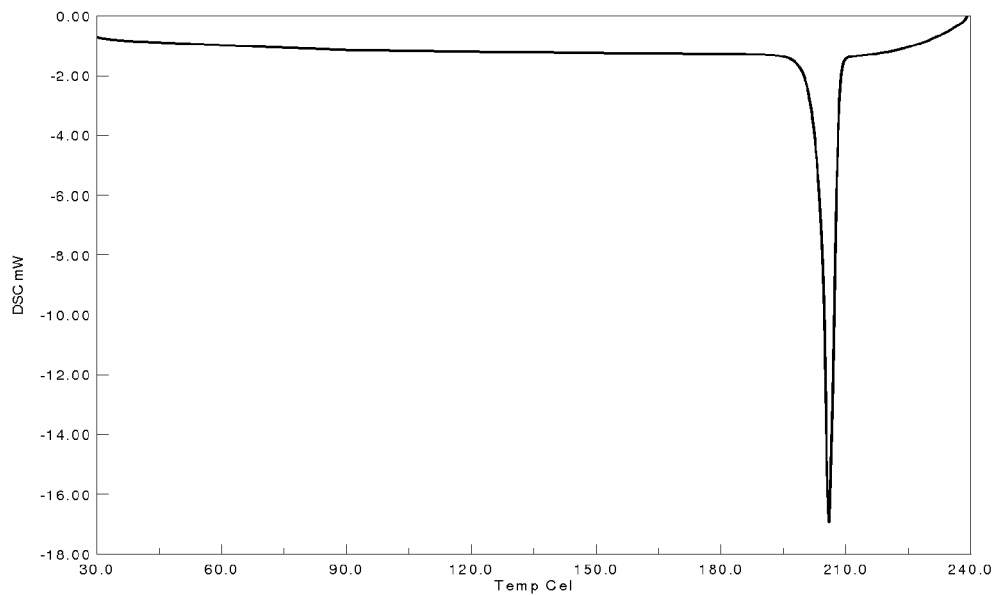
FIG. 33 shows a DSC curve of the crystal obtained in Example 15 (crystal O). The longitudinal axis of the figure shows heat flow (mW), and the horizontal axis shows temperature (° C.).
Figure 42:
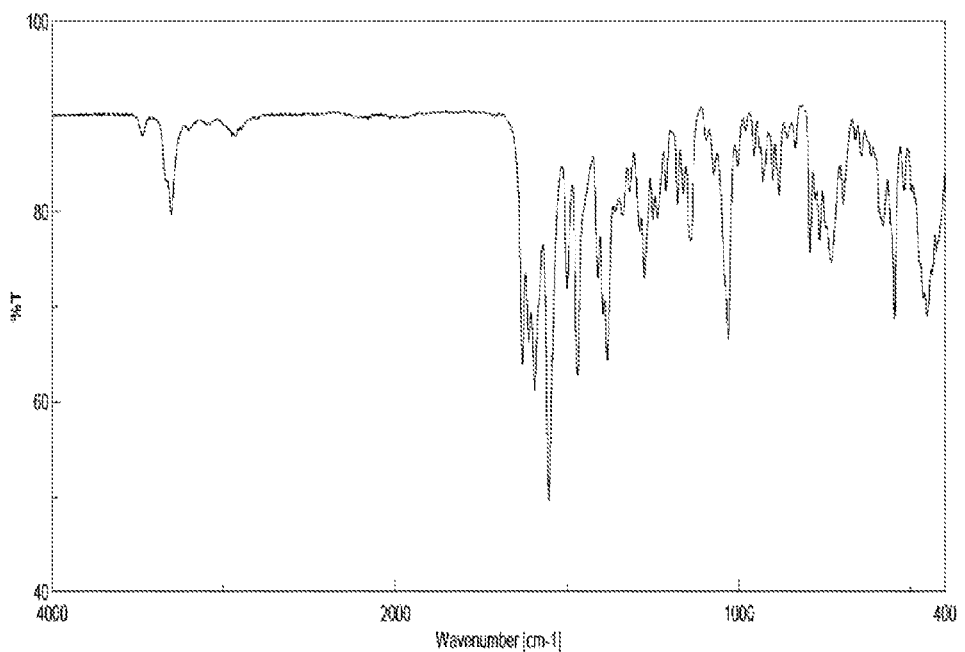
FIG. 42 shows an infrared absorption spectrum of the crystal obtained in Example 15 (crystal O). The longitudinal axis of the figure shows transmittance (% T), and the horizontal axis shows the wave number (cm$^{-1}$) of the infrared radiation applied.

A moisture sorption/desorption isotherm obtained by automatic measurement of the amount of water vapor adsorbed onto the obtained crystal is shown in FIG. 24, a DSC curve obtained by differential scanning calorimetry is shown in FIG. 33, and an infrared absorption spectrum thereof is shown in FIG. 42.

TABLE 16

| Peak No. | 2θ | d value | Relative intensity |
|---|---|---|---|
| 1 | 5.02 | 17.59 | 24 |
| 2 | 7.70 | 11.47 | 56 |
| 3 | 8.22 | 10.75 | 8 |
| 4 | 10.12 | 8.73 | 100 |
| 5 | 14.06 | 6.29 | 26 |
| 6 | 15.24 | 5.81 | 37 |
| 7 | 15.50 | 5.71 | 22 |
| 8 | 16.54 | 5.36 | 16 |
| 9 | 17.36 | 5.10 | 35 |
| 10 | 20.38 | 4.35 | 9 |
| 11 | 22.36 | 3.97 | 6 |
| 12 | 22.76 | 3.90 | 24 |
| 13 | 23.32 | 3.81 | 29 |
| 14 | 25.02 | 3.56 | 5 |
| 15 | 25.60 | 3.48 | 7 |
| 16 | 26.90 | 3.31 | 5 |
| 17 | 27.54 | 3.24 | 6 |
| 18 | 28.04 | 3.18 | 7 |
| 19 | 30.72 | 2.91 | 7 |

Example 16

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide crystal P Water (20 mL) was added to 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride (which had been obtained by the same operations as those in the method described in the above Reference Example 2) (505 mg, 1.047 mmol), and the resulting mixture was then stirred at room temperature for 3 hours. Thereafter, a precipitate was collected by filtration, and was then air-dried at room temperature for 3 days, so as to obtain the above title compound as crystal P (426 mg, 0.883 mmol). Yield: 84%.

The elemental analysis measurement values (theoretical values) of the obtained crystal are shown below.

For 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide, C, 46.35%; (51.18%), H, 5.00%; (4.52%), O, 14.49%; (7.18%), N, 20.00%; (21.99%), Cl, 7.41%; (7.95%), and S, 6.68%; (7.19%).

A diffraction pattern from the X-ray powder diffraction (CuKα, λ=1.54 angstroms) of the obtained crystal is shown in FIG. 16, and peaks with a relative intensity of 7 or greater, when the maximum peak intensity is set at 100 in FIG. 16, are shown in Table 17.

Figure 25:
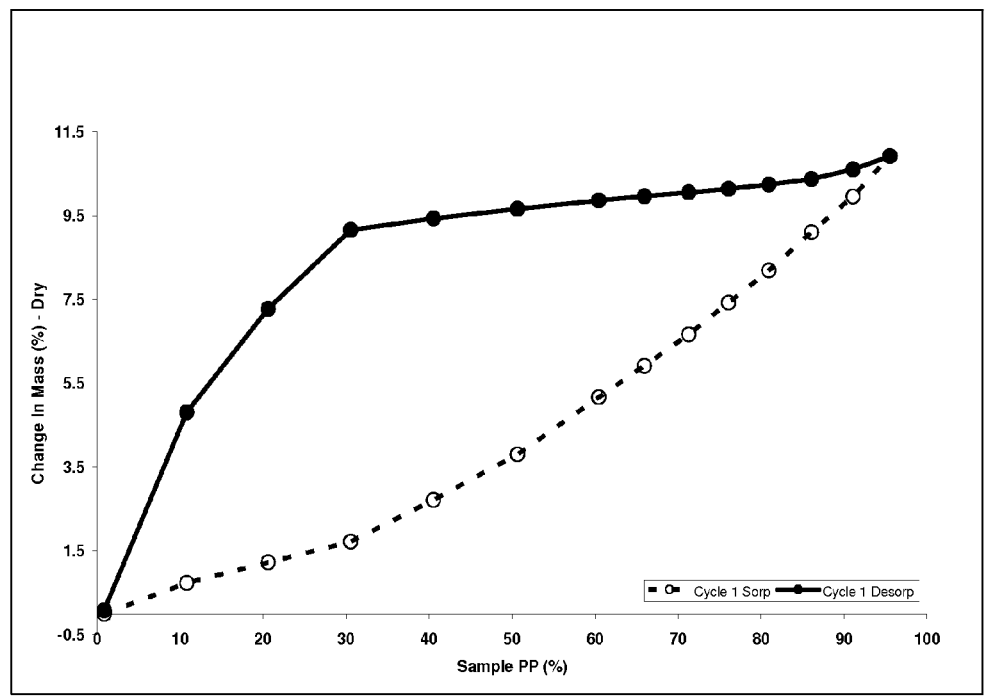
FIG. 25 shows a moisture sorption/desorption isotherm of the crystal obtained in Example 16 (crystal P). The longitudinal axis of the figure shows a change (%) in the mass of the compound, and the horizontal axis shows relative humidity (% RH). The broken line with open circles shows a moisture sorption curve, and the solid line with filled circles shows a moisture desorption curve.
Figure 34:
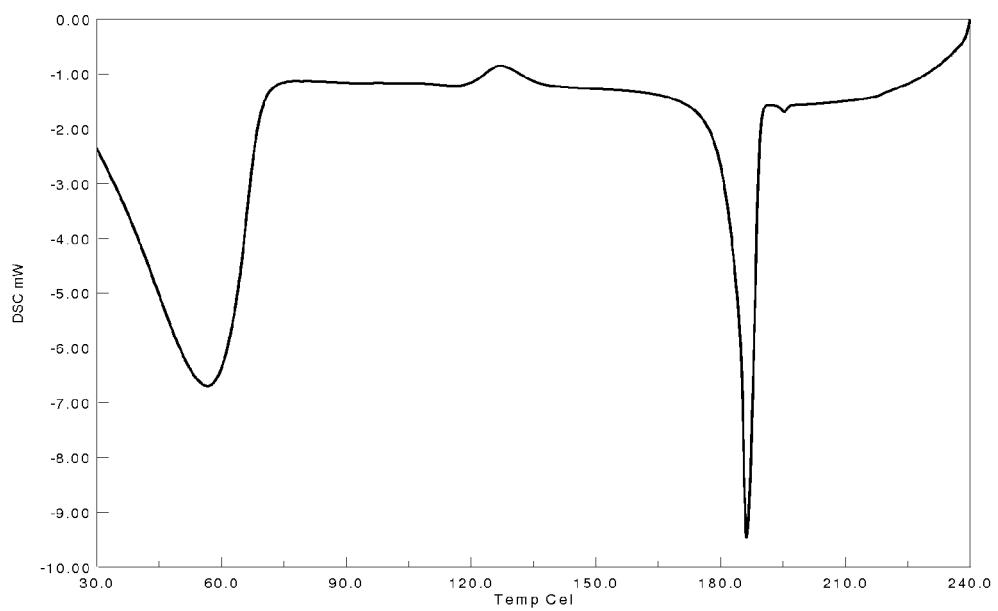
FIG. 34 shows a DSC curve of the crystal obtained in Example 16 (crystal P). The longitudinal axis of the figure shows heat flow (mW), and the horizontal axis shows temperature (° C.).
Figure 43:
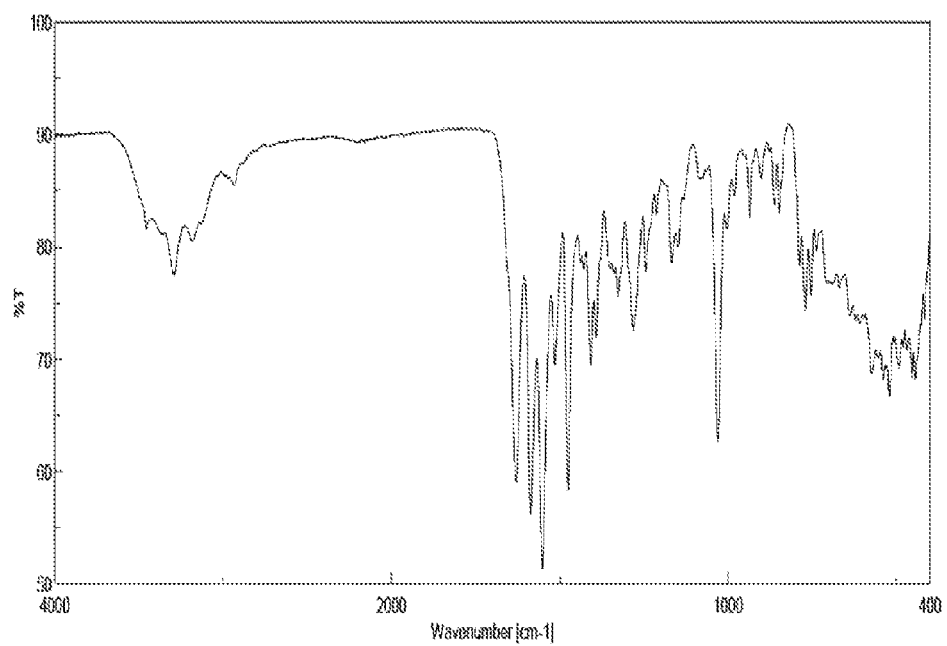
FIG. 43 shows an infrared absorption spectrum of the crystal obtained in Example 16 (crystal P). The longitudinal axis of the figure shows transmittance (% T), and the horizontal axis shows the wave number (cm$^{-1}$) of the infrared radiation applied.

A moisture sorption/desorption isotherm obtained by automatic measurement of the amount of water vapor adsorbed onto the obtained crystal is shown in FIG. 25, a DSC curve obtained by differential scanning calorimetry is shown in FIG. 34, and an infrared absorption spectrum thereof is shown in FIG. 43.

TABLE 17

| Peak No. | 2θ | d value | Relative intensity |
|---|---|---|---|
| 1 | 5.08 | 17.38 | 100 |
| 2 | 6.56 | 13.46 | 14 |
| 3 | 7.90 | 11.18 | 10 |
| 4 | 8.72 | 10.13 | 32 |
| 5 | 11.58 | 7.64 | 18 |
| 6 | 13.18 | 6.71 | 26 |
| 7 | 13.64 | 6.49 | 8 |
| 8 | 14.64 | 6.05 | 20 |
| 9 | 15.86 | 5.58 | 8 |
| 10 | 17.34 | 5.11 | 12 |
| 11 | 18.20 | 4.87 | 7 |
| 12 | 19.94 | 4.45 | 10 |
| 13 | 20.72 | 4.28 | 9 |
| 14 | 22.24 | 3.99 | 12 |
| 15 | 23.32 | 3.81 | 8 |
| 16 | 24.78 | 3.59 | 15 |
| 17 | 25.76 | 3.46 | 10 |
| 18 | 26.48 | 3.36 | 21 |

TABLE 17-continued

| Peak No. | 2θ | d value | Relative intensity |
|---|---|---|---|
| 19 | 27.64 | 3.22 | 10 |
| 20 | 28.34 | 3.15 | 8 |

Test Example 1

Cell Growth Inhibition Assay

A cell growth inhibition assay was performed using two types of cells (human breast cancer cell line SK-BR-3 and human lung cancer cell line NCI-H460).

Cells of each type were suspended in a medium and seeded into a 96-well multi-well plate at 2000 cells/150 μL/well in the case of SK-BR-3 and at 500 cells/150 μL/well in the case of NCI-H460. Compound (I) was dissolved in DMSO, and this was diluted with medium to prepare a sample solution (DMSO concentration: 0.5% or less). On the day following the seeding, 50 μL of DMSO-containing medium to which the test compound was not added (hereinafter called DMSO diluted solution; DMSO concentration: 0.5% or less) or 50 μL of the sample solution was further added to the cells. An MTT assay was performed immediately after and 72 hours after adding the sample solution or the DMSO diluted solution to the cells. The MTT assay was performed as follows.

5 mg/mL of an MTT (3-(4,5-dimethylthiazol-2-yl)-2,5-diphenyltetrazolium bromide) solution was added at 20 μL per well. Thereafter, the plate was incubated at 37° C. in 5% $CO_2$ for four hours. The plate was centrifuged at 1200 rpm for five minutes, and then the culture supernatant was removed by suction using a dispenser. DMSO was added at 150 μL per well, and the generated formazan was dissolved. The plate was stirred using a plate mixer to uniformly color the respective wells. The absorbance of each well was measured using a plate reader at an OD of 540 nm with a reference of 660 nm.

T/C (%) for each concentration was determined by the following calculation formula and a dose-response curve was drawn to calculate the 50% growth inhibitory concentration ($GI_{50}$ value), based on the assumption that the OD value measured immediately after adding the sample solution was S, the OD value measured 72 hours after adding the sample solution was T, and the OD value measured 72 hours after adding the DMSO diluted solution was C.

$T/C(\%)=(T-S)/(C-S)\times 100$

Compound (1) exhibited a $GI_{50}$ value of 13 (nM) with respect to SK-BR-3 cells, and a $GI_{50}$ value of 26 (nM) with respect to NCI-H460 cells.

Formulation Example 1

Capsule 5 g of the crystal obtained in Example 1, 115 g of lactose, 58 g of corn starch, and 2 g of magnesium stearate were mixed using a V-shape rotating mixer, and the resulting mixture was then filled in an amount of 180 mg each into capsule No. 3, so as to obtain a capsule.

Formulation Example 2

Tablet 5 g of the crystal obtained in Example 1, 90 g of lactose, 34 g of corn starch, 20 g of crystalline cellulose, and 1 g of magnesium stearate were mixed using a V-shape rotating mixer, and the resulting mixture was then subjected to a tablet-making machine at a mass of 150 mg per tablet, so as to obtain a tablet.

Formulation Example 3

Suspension

Methyl cellulose was dispersed and dissolved in purified water to prepare a dispersion medium. The crystal obtained in Example 1 was weighed in a mortar. The aforementioned dispersion medium was added by small amounts thereto, until they were fully blended. Purified water was added to the mixture to prepare 100 g of a suspension.

The invention claimed is:

1. A crystal of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide represented by the following formula (1):

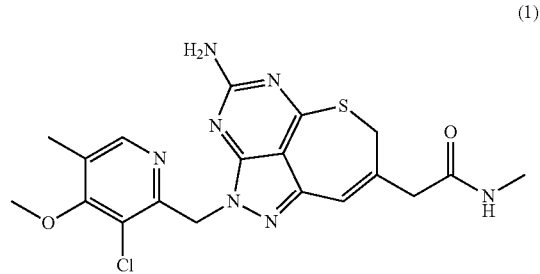

(1)

wherein the crystal has the X-ray diffraction pattern shown in FIG. 1, in an X-ray powder diffraction pattern obtained by irradiation with copper Kα radiation (wavelength λ=1.54 angstroms).

2. The crystal of claim 1 which shows principal peaks at angles of diffraction 2θ of 3.10, 4.02, 6.22, 8.54, 9.62, 11.58, 11.84, 12.16, 12.56, 14.46, 15.02, 15.26, 17.86, 22.14, 22.96, 23.10, 23.82, 24.26 and 26.82, in an X-ray powder diffraction pattern obtained by irradiation with copper Kα radiation (wavelength λ=1.54 angstroms).

3. A pharmaceutical composition comprising a crystal according to claim 1 and a pharmacologically acceptable carrier.

* * * * *